US011751882B2

(12) United States Patent
Gregan et al.

(10) Patent No.: US 11,751,882 B2
(45) Date of Patent: Sep. 12, 2023

(54) CLIP AND CLIP ASSEMBLY

(71) Applicant: UNITED STATES ENDOSCOPY GROUP, INC., Mentor, OH (US)

(72) Inventors: Darren Gregan, Auburn Township, OH (US); Scott Haack, Chardon, OH (US); Sven Huijs, Madison, OH (US); Sarah Insull, Painesville, OH (US); Keith R. John, Chardon, OH (US); Christopher J. Kaye, Middleburg Heights, OH (US); Gary E. Mann, Painesville, OH (US); Tony Martella, Painesville, OH (US); Joseph Michelini, Spring Lake, MI (US); Reza Mohammadpour, Willoughby Hills, OH (US); Eric Roush, Redwood City, CA (US); Jessica Russo, Sagamore Hills, OH (US); Alex Uspenski, Chardon, OH (US); John P. Winstanley, Madison, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 227 days.

(21) Appl. No.: 16/192,202

(22) Filed: Nov. 15, 2018

(65) Prior Publication Data

US 2019/0150929 A1 May 23, 2019

Related U.S. Application Data

(60) Provisional application No. 62/767,353, filed on Nov. 14, 2018, provisional application No. 62/586,617, filed on Nov. 15, 2017.

(51) Int. Cl.
*A61B 17/122* (2006.01)
*A61B 17/12* (2006.01)
(Continued)

(52) U.S. Cl.
CPC ............ *A61B 17/122* (2013.01); *A61B 17/12* (2013.01); *A61B 17/1285* (2013.01);
(Continued)

(58) Field of Classification Search
CPC ..... A61B 17/083; A61B 17/12; A61B 17/122; A61B 17/1227; A61B 17/128;
(Continued)

(56) References Cited

U.S. PATENT DOCUMENTS 8,900,254 B2 * 12/2014 Kobayashi ......... A61B 17/1227 606/139
9,386,992 B2 * 7/2016 Terada ................. A61B 17/122
(Continued)

FOREIGN PATENT DOCUMENTS

EP 1829489 A1 9/2007
EP 1993452 A2 11/2008
(Continued)

OTHER PUBLICATIONS

Invitaton to Pay Additional Fees from PCT/US2018/061321 dated Feb. 21, 2019 (13 pages).
(Continued)

*Primary Examiner* — Robert A Lynch
(74) *Attorney, Agent, or Firm* — CALFEE, HALTER & GRISWOLD LLP

(57) ABSTRACT

An endoscopic device, includes a clip assembly and a driving assembly. The clip assembly includes a first jaw, a second jaw, a pivot, a housing having an internal channel, and a release portion connecting to the first and second jaws. At least a portion of the first and second jaws is disposed within the internal channel, the first and second jaws selectively move along with the internal channel. The driving assembly includes an outer sheath, an inner tube, movably disposed within the outer sheath, and a driver, movably
(Continued)

42 31 40 20 10 disposed within the inner tube, and removably received within the release portion. The driver is unbrokenly released from the release portion by a predetermined pull force. The housing and the outer sheath form a releasable handshake engagement. The inner tube extending into the housing prevents the handshake engagement from disengaging.

20 Claims, 57 Drawing Sheets

(51) Int. Cl.
*A61B 17/128* (2006.01)
*A61B 17/00* (2006.01)

(52) U.S. Cl.
CPC .................. *A61B 17/00234* (2013.01); *A61B 2017/00477* (2013.01); *A61B 2017/12004* (2013.01); *A61B 2017/1205* (2013.01)

(58) Field of Classification Search
CPC ...... A61B 17/1285; A61B 2017/00234; A61B 2017/00477; A61B 2017/12004; A61B 2017/1205; A61B 2017/12054; A61B 2017/12095; A61B 2017/2929
See application file for complete search history.

(56) References Cited

U.S. PATENT DOCUMENTS

| | | | | |
|---|---|---|---|---|
| 9,867,624 | B2 * | 1/2018 | Satake | A61B 17/083 |
| 2002/0045909 | A1 | 4/2002 | Kimura et al. | |
| 2002/0133178 | A1 | 9/2002 | Muramatsu et al. | |
| 2002/0151916 | A1 * | 10/2002 | Muramatsu | A61B 17/1227 606/158 |
| 2005/0143767 | A1 * | 6/2005 | Kimura | A61B 50/30 606/158 |
| 2006/0271072 | A1 * | 11/2006 | Hummel | A61B 17/122 606/142 |
| 2008/0306491 | A1 * | 12/2008 | Cohen | A61B 17/122 606/142 |
| 2010/0016873 | A1 * | 1/2010 | Gayzik | A61B 17/1227 606/151 |
| 2011/0245855 | A1 | 10/2011 | Matuoka et al. | |
| 2012/0059394 | A1 * | 3/2012 | Brenner | A61B 17/122 606/142 |
| 2013/0072945 | A1 * | 3/2013 | Terada | A61B 17/1227 606/157 |
| 2013/0226200 | A1 | 8/2013 | Kappel | |

FOREIGN PATENT DOCUMENTS

| | | | |
|---|---|---|---|
| JP | 2010-511483 | A | 4/2010 |
| JP | 2010-525879 | A | 7/2010 |
| WO | 2016/185965 | A1 | 11/2016 |

OTHER PUBLICATIONS

International Search Report from PCT/US2018/061321 dated Apr. 16, 2019 (19 pages).
Office Action from U.S. Appl. No. 16/684,067 dated Apr. 19, 2021.
Office Action from U.S. Appl. No. 16/684,067 dated Oct. 29, 2021.
Office Action from U.S. Appl. No. 16/684,067 dated Apr. 15, 2022.
Office Action from U.S. Appl. No. 16/684,067 dated Aug. 26, 2022.

* cited by examiner

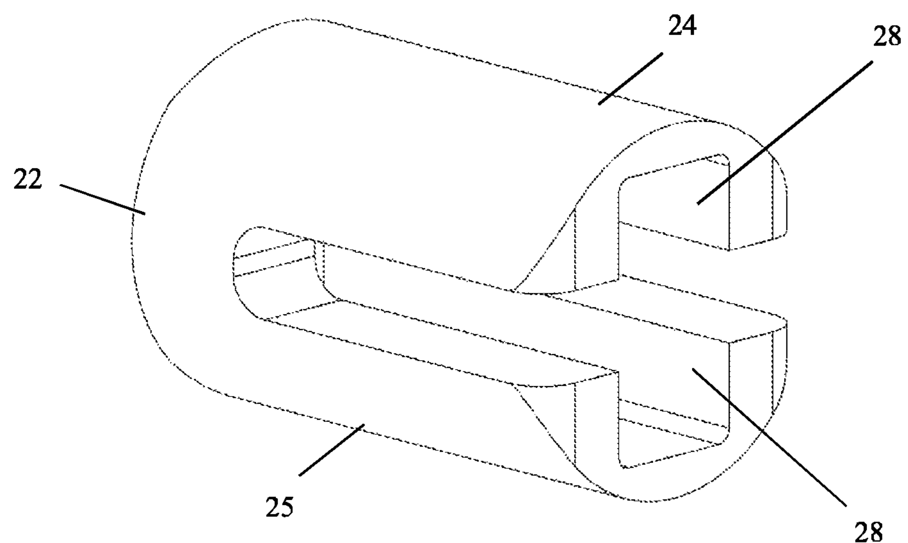
Figure 6a
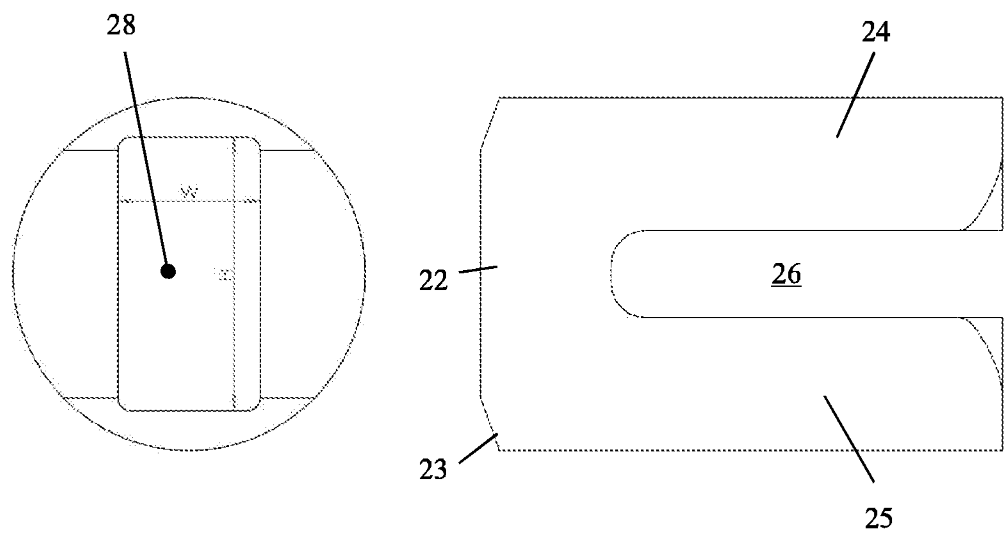
Figure 6b
Figure 6c

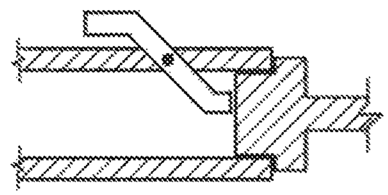
Figure 57a
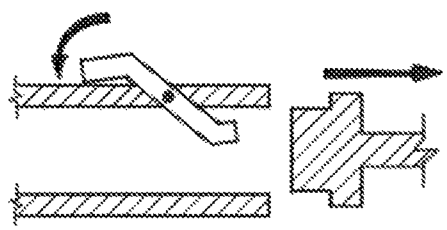
Figure 57b
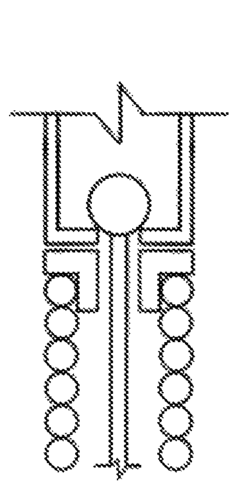
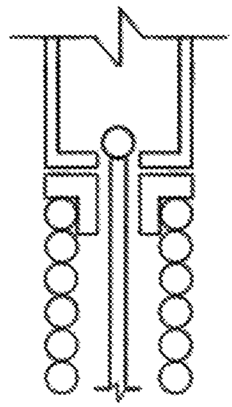
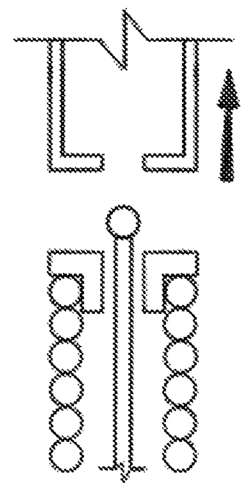
Figure 58a Figure 58b Figure 58c

CLIP AND CLIP ASSEMBLY

CROSS-REFERENCES

The present application claims benefits and priority to U.S. Provisional Patent Application No. 62/586,617, filed on Nov. 15, 2017, and U.S. Provisional Patent Application No. 62/767,353, filed on Nov. 14, 2018, the entire disclosures of which are incorporated herein by reference.

BACKGROUND

Hemostatic clips are used to clamp or close tissue, vessels or ducts. They are generally used to control bleeding of tissue, vessel or ducts instead of suturing or stapling. Hemostatic clips, on the market are deemed "MR Conditional" per ASTM F2503-13, which can lead to clip failure during an MRI procedure. Under FDA guidance and ASTM F2503-13, "MR Safe" means that the item poses no known hazards in all MRI environments. An MR Safe clip will be stable in patients undergoing MRI and poses no known hazards in MRI environments.

SUMMARY

The present application describes a clip, comprising: a grab portion at a distal end of the clip, and a release portion at a proximal end of the clip. The clip is made of electrically nonconductive or non-magnetic material. The novel aspects of this device center around the fact that the clip can grasp and hold the tissue while residing in the body being subjected to a MRI procedure. The other clips on the market react under the induced magnetic field and this reaction (which can include vibration and/or temperature increase) which can compromise the retention ability of the clip. Utilizing materials that are not influenced by the high-energy magnetic field (such as plastics, glass, ceramics or non-ferrous metals), alleviate this concern.

The present application further describes a clip assembly, comprising a clip and a locking mechanism. The clip includes a first arm at a distal end of the clip, a second arm at the distal end of the clip, and a release portion at a proximal end of the clip. At least one of the first and second arms is movable between an open position and a closed position. The distal end of each arm has an engagement portion. The clip is made of electrically nonconductive or non-magnetic material. The locking mechanism is configured to lock the first and second arms in the closed position.

The present application further describes a method for applying a clip to a patient, comprising 1) expose the clip at its open position; 2) adjust the driver to align the engagement portions to a treatment area; 3) clip retracts into outer sheath to close the clip; 4) push the pusher tube to move the collar past the retention mechanism; 5) extend the driver out and retract the pusher tube back; 6) release the driver from the clip.

BRIEF DESCRIPTION OF THE DRAWINGS

Features and advantages of the general inventive concepts will become apparent from the following detailed description made with reference to the accompanying drawings.

FIG. 6*a* is a perspective view of an embodiment of the collar;

FIG. 6*b* is a left view of the collar shown in FIG. 6*a;*

FIG. 6*c* is a front view of the collar shown in FIG. 6*a;*

FIGS. 57*a-b* show various views of another embodiment of engagements;

FIGS. 58*a-c* show various views of another embodiment of engagements;

DETAILED DESCRIPTION

This Detailed Description merely describes exemplary embodiments in accordance with the general inventive concepts and is not intended to limit the scope of the invention or the claims in any way. Indeed, the invention as described by the claims is broader than, and unlimited by, the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers, such as for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

A person skilled in the art should reasonably understand that the clip could be used for placement in the gastrointestinal tract for endoscopic marking; hemostasis for: mucosal/sub-mucosal defects less than about 3 cm, bleeding ulcers, arteries less than about 2 mm, polyps less than about 1.5 cm in diameter, diverticula in the colon; prophylactic clipping to reduce the risk of delayed bleeding post lesion resection; anchoring to affix jejunal feeding tubes to the wall of the small bowel; anchoring to affix fully covered esophageal self-expanding metal stents to the wall of the esophagus; and as a supplemental closure method of luminal perforations less than about 20 mm that can be treated conservatively.

Figure 1A:
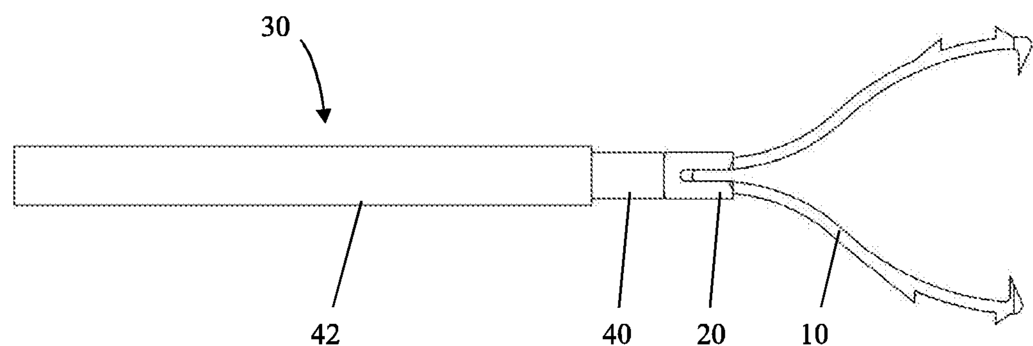
FIG. 1*a* is a front view of an exemplary clip assembly and an exemplary driving assembly of the present subject matter.
Figure 1B:
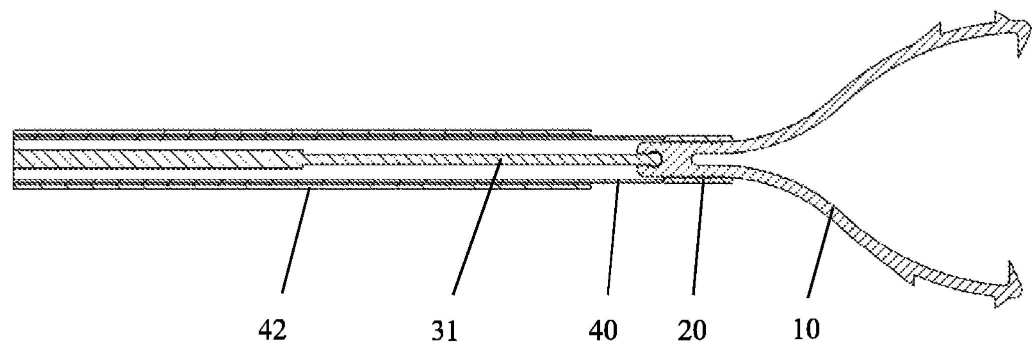
FIG. 1*b* is a cross-sectional view of the embodiments shown in FIG. 1.
Figure 2:
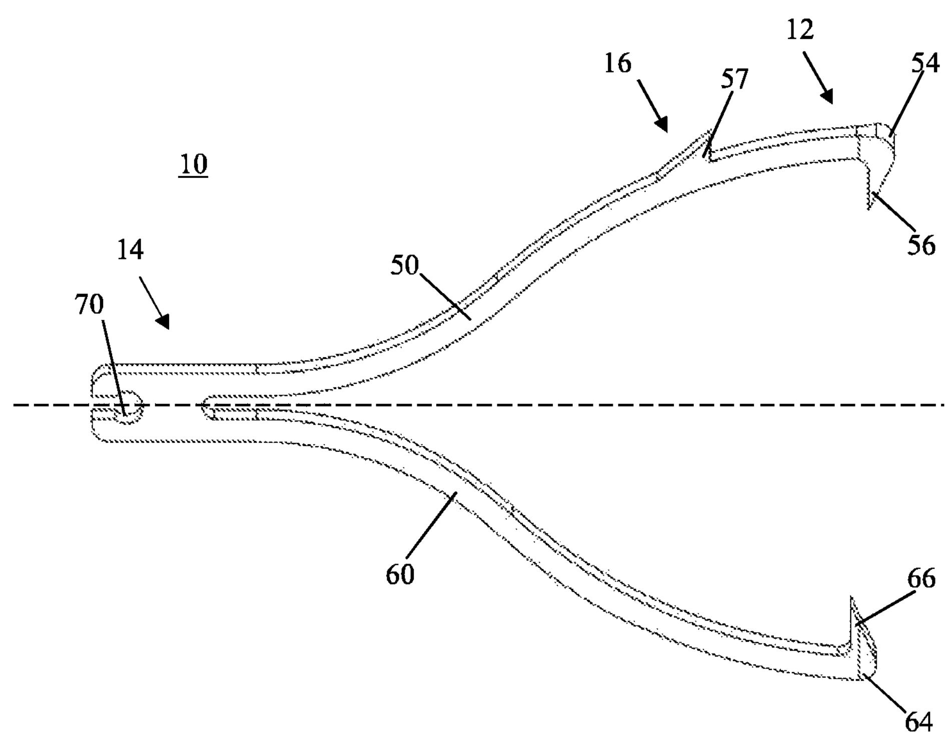
FIG. 2 is a perspective view of an embodiment of the clip.

As shown in FIGS. 1 and 2, the present subject matter describes a clip assembly and its driving assembly. The clip assembly comprises a clip 10 and a locking mechanism, such as a collar 20. The driving assembly (catheter assembly) 30. The driving assembly 30 is configured to operate and release the clip assembly as desired.

As shown in FIG. 2, the exemplary clip 10 comprises a grab portion 12 at a distal end of the clip 10 and a release portion 14 at a proximal end of the clip 10. In an embodiment of the clip, the grab portion 12 comprises a first arm 50 and a second arm 60. In some embodiments, one of the first and second arms 50, 60 is configured to be movable; the other arm is stationary. In some embodiments, both the first and second arms 50, 60 are configured to be movable. In some embodiments, one of the first and second arms 50, 60 is an elastic curved arm. In some embodiments, both the first and second arms 50, 60 are elastic curved arms. A portion of the arm is convex outward from the axis of the clip. In other words, the clip has a wishbone shape, which allows a quick closure around tissue. The curved arms create an entrapment space for gathering tissue. A person skilled in the art should reasonably understand that the clip 10 may comprise more than two arms, such as three arms or four arms. In some embodiments, the clip has even number of arms. The arms could be planar. The arms could also be non-planar. In some embodiments, the clip 10 has at least an 11 mm jaw opening at the open position. In some embodiments, the clip 10 may fit in, rotate and move through a scope with 2.8 mm channel at the closed position.

Figure 7A:
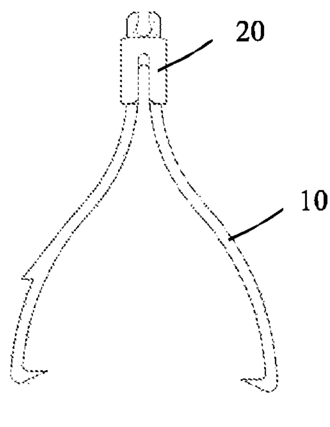
FIGS. 7*a*-7*c* shows perspective views of how the clip and the collar operate.
Figure 7B:
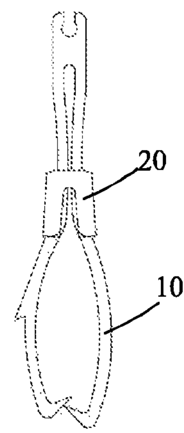
Figure 7C:
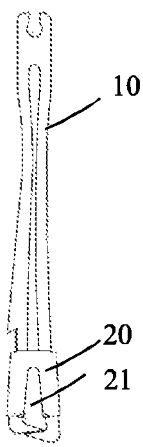

In an embodiment of the clip, a distal end 54 of the first arm 50 comprises a first engagement portion 56. A distal end 64 of the second arm 60 comprises a second engagement portion 66. Referring to FIGS. 7*a*-7*c*, when the clip 10 starts to close, the distal ends 54, 64 of the first and second arms 50, 60 move towards each other and the first and second engagement portions 56, 66 are engaged with each other, which allows for a pre-load on the arms and increases its ability to grip the tissue. When the clip is at its fully closed position, the arms keep stressed in order to achieve a better hemostatic or other desired effect. Meanwhile, a tissue entrapment area 21 is formed near two engagement portions.

Back to FIG. 2, in some embodiments, the first or second engagement portions 56 or 66 is an offset tooth. In some embodiments, the offset teeth have a profile in which the width of the distal engagement portions are wider than the arms of the clip to allow for superior grip on tissue. These engagement portions may be made of alternative materials and attached to the arms. A person skilled in art should reasonably understand that the first and second engagement portions 56, 66 may be multiple offset teeth, or other known structures that may stably engage each other in order to achieve effective hemostatic effects. In an alternative embodiment of the clip, the first and second engagement portions comprise dual offset teeth. The dual teeth structure prevents the offset teeth from overlapping too much and becoming stuck in a closed position.

In the embodiment of the clip shown in FIG. 2, at least one arm comprises a retention mechanism 16. The retention mechanism 16 comprises a retention fin 57 disposed near the distal end 54 of the first arm 50. The retention fin 57 allows the collar 20 to move from the proximal end of the clip 10 towards the distal end of the clip. The retention fin 57 may contain a negative angle or other geometry such that interfacing with geometry of collar 20 prevents the collar 20 from sliding away from the distal end 54 of the first arm 50 so as to keep the clip 10 at the closed position and the first and second engagement portions 56, 66 engaged.

Figure 3:
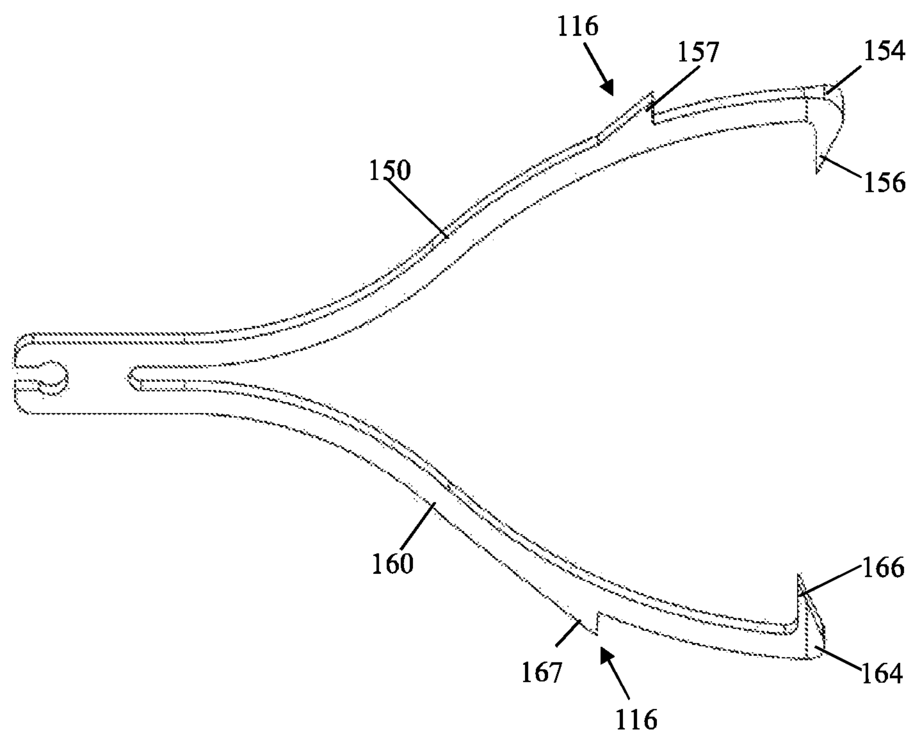
FIG. 3 is a perspective view of another embodiment of the clip.

In another embodiment of the clip shown in FIG. 3, the retention mechanism 116 comprises a first retention fin 157 disposed near the first distal end 154 of the first arm 150 and a second retention fin 167 disposed near the second distal end 164 of the second arm 160. The first and second retention fins 157, 167 have similar function as the retention fin 57 described above.

Figure 4:
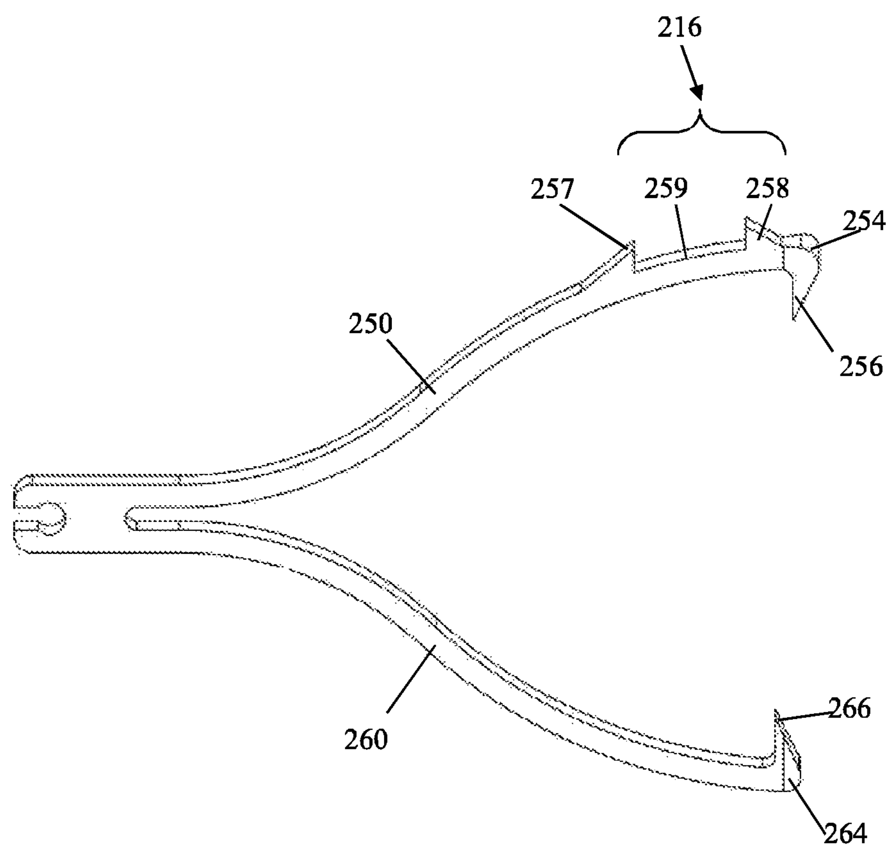
FIG. 4 is a perspective view of another embodiment of the clip.

In another embodiment of the clip shown in FIG. 4, the retention mechanism 216 comprises a retention fin 257, a distal stop 258, and a recess 259 between the retention fin 257 and the distal stop 258. The retention fin 257, the distal stop 258, and the recess 259 are disposed near the distal end 254 of the first arm 250. The retention fin 257 has similar function as the retention fin 57 described above. The length of the recess 259 is configured to receive the collar 20. The distal stop 258 prevents the collar 20 from sliding out of the distal ends 254, 264 of the first and second arms 250, 260.

Figure 5:
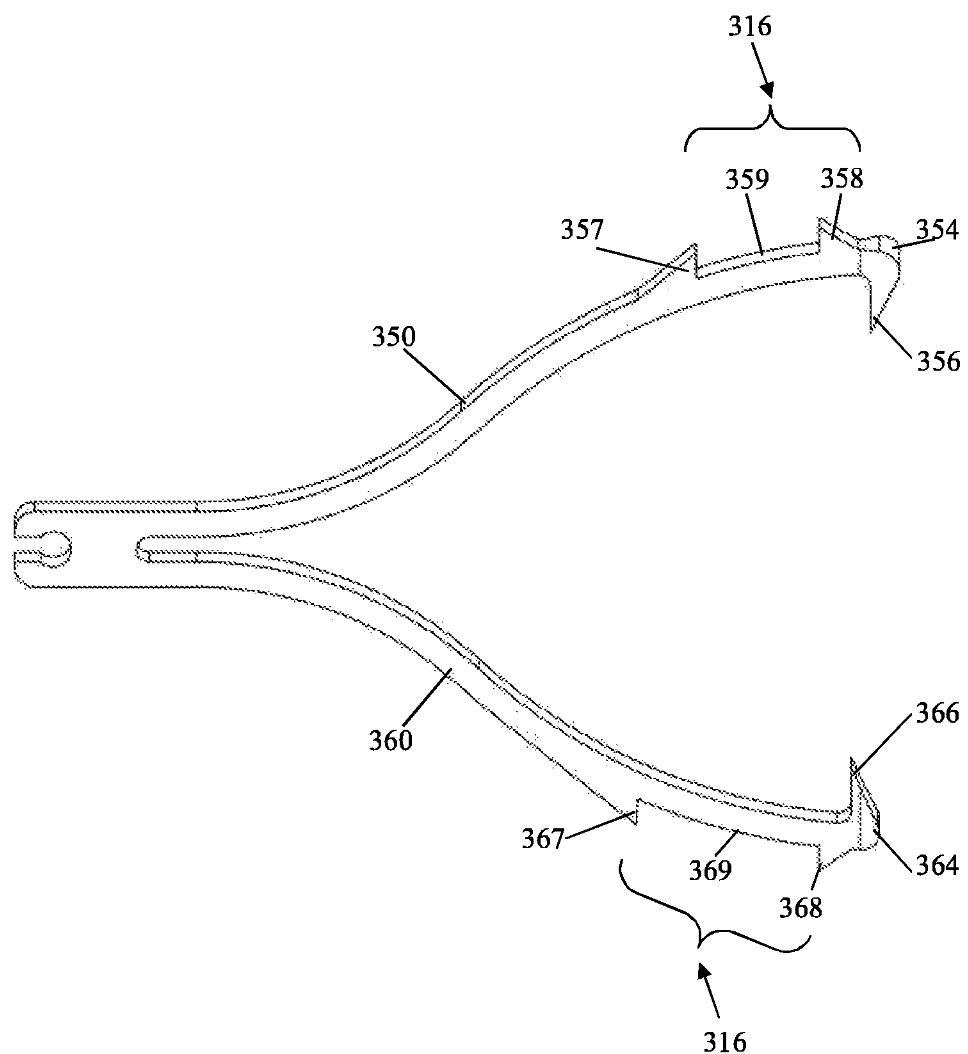
FIG. 5 is a perspective view of another embodiment of the clip.

In another embodiment of the clip shown in FIG. 5, the retention mechanism 316 comprises first and second retention fin 357, 367, first and second distal stops 358, 368, a first recess 359 between the first retention fin 357 and the first distal stop 358, and a second recess 369 between the second retention fin 367 and the second distal stop 368. The length of the first and second recesses 359, 369 are configured to receive the collar 20. The first and second retention fins 357, 367 have similar function as the retention fin 57 described above. The first and second distal stops 358, 368 have similar function as the distal stop 158 described above.

A person skilled in the art should reasonably understand that besides the retention mechanisms described above, other known retention mechanisms may be used here to secure the collar.

Referred to FIGS. 6*a*-6*c* and an exemplary embodiment of the clip 10 of FIG. 2, the collar 20 comprises a sleeve 22 and a guide channel 28 at the center of the sleeve 22. The arms 50, 60 of clip 10 are able to pass through the guide channel 28 so that the collar 20 is able to move along the arms 50, 60 of clip 10. The guide channel 28 has a height H and a width W. In some embodiments, the height H of the guide channel 28 is equal to or slightly higher than a height H' of the retention fin 57 portion of the clip 10 at a closed position. In some embodiments, the width W of the guide channel 28 is equal to or slightly wider than a width W' of the clip 10. The guide channel 28 is configured to enable the collar 20 to pass over and to be retained by the retention fin 57. Meanwhile, the retained collar 20 forces the first and second engagement portions 56, 66 to be closed. The guide channel 28 is also configured to prevent the clip 10 from rotating within the collar 20. In some embodiments, the guide channel 28 is rectangular. A person skilled in the art should reasonably understand that the guide channel could be other shapes as long as the guide channel prevents the clip from rotating within the collar while the arms are movable in the guide channel.

The collar 20 further comprises two support arms 24, 25 extending from a distal end of the sleeve 22. The support arms 24, 25 do not interfere with the guide channel 28. When the collar 20 locks the clip 10 and is retained by the retention fin 57, the support arms 24, 25 are towards the distal ends 54, 64 of the arms 50, 60. In some embodiments, the support arms 24, 25 are configured to cover the arms 50, 60 up to the distal ends 54, 64 in order to provide additional strength during cinching. However, in some embodiments, the support arms 24, 25 do not extend beyond the first and second engagement portions 56, 66 so as to avoid the support arms 24, 25 interfering with tissue entrapments. In some embodiments, the support arms 24, 25 are spaced by openings 26. In some embodiments, the support arms 24, 25 merely cover the arms 50, 60 when the clip 10 is closed. The openings 26 are configured to receive tissue entrapped by the first and second engagement portions 56, 66 when the clip 10 is fully closed and locked. The openings 26 and a gap between the arms 50, 60 create a tissue entrapment area 21 (shown in FIG. 7*c*). In some embodiments, the support arms 24, 25 are elastic and bendable so that the arms 50, 60 are able to maintain a maximum open jaw and are easy to be closed. In some embodiments, the support arms 24, 25 are rigid. In some embodiments, the sleeve 22 comprises chamfers or fillets 23 on the outside of the proximal end of the sleeve 22. The chamfers or fillets 23 help the collar 20 to interlock with the retention fins.

In an alternative embodiment of the clip assembly, the retention mechanism of the arm comprises a retention fin. The support arm of the collar comprises a slot disposed at an internal surface of the support arm. The slot is configured to catch the retention fin. In some embodiments, the slot is a through hole.

Turning back to FIGS. 1*a*-1*b*, as an embodiment of the present subject matter, the driving assembly 30 comprises a driver 31, a pusher tube 40, and an outer sheath 42. The pusher tube 40 is configured to be disposed within the outer sheath 42. The driver 31 is configured to be disposed within the pusher tube 40. The outer sheath 42 is configured to contain the clip 10 and the collar 20. The pusher tube 40 is configured to contain the clip 10 but to not be able to contain the collar 20. In some embodiments, the outer sheath 42 prevents the coupled connector 34 and release portion 14 to be decoupled when they are covered by the pusher tube 40. In some embodiments, the collar 20 prevents the coupled connector 34 and release portion 14 to be decoupled when they are covered by the collar 20.

The driving assembly 30 and the release portion 14 of the clip 10 work together to operate the clip 10. The outer sheath 42 is configured to contain the clip 10 before the clip 10 is disposed. The outer sheath 42 is configured to move towards the proximal end of the clip 10 and to release the grab portion 12 of the clip 10 out of the outer sheath 42. Consequently, the grab portion 12 would become open. The driver 31 is configured to move or rotate the clip 10 so that the clip 10 is able to be disposed as desired. When the clip 10 is at its desired position, the driver 31 is retracted into the outer sheath 42 and closes the grab portion 12 of the clip 10. The pusher tube 40 is configured to push the collar 20 moving towards the distal end of the clip 10, and the collar 20 consequently locks the clip 10.

Figure 8A:
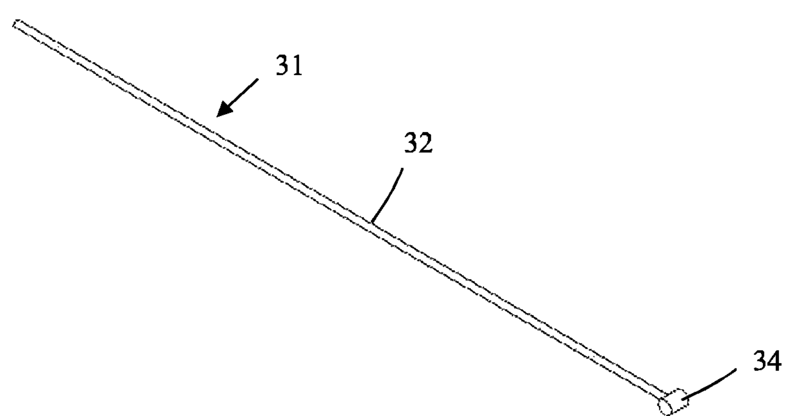
FIG. 8*a* is a perspective view of an embodiment of the driver shown in FIG. 1.
Figure 8B:
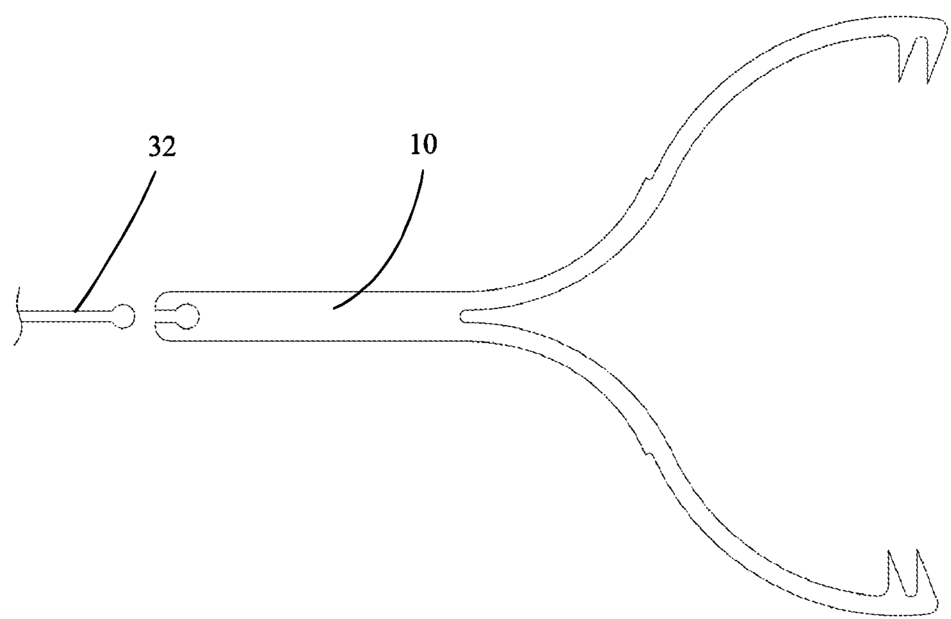
FIG. 8*b* is a front view of the driver and the clip assembly shown in FIG. 1.
Figure 9:
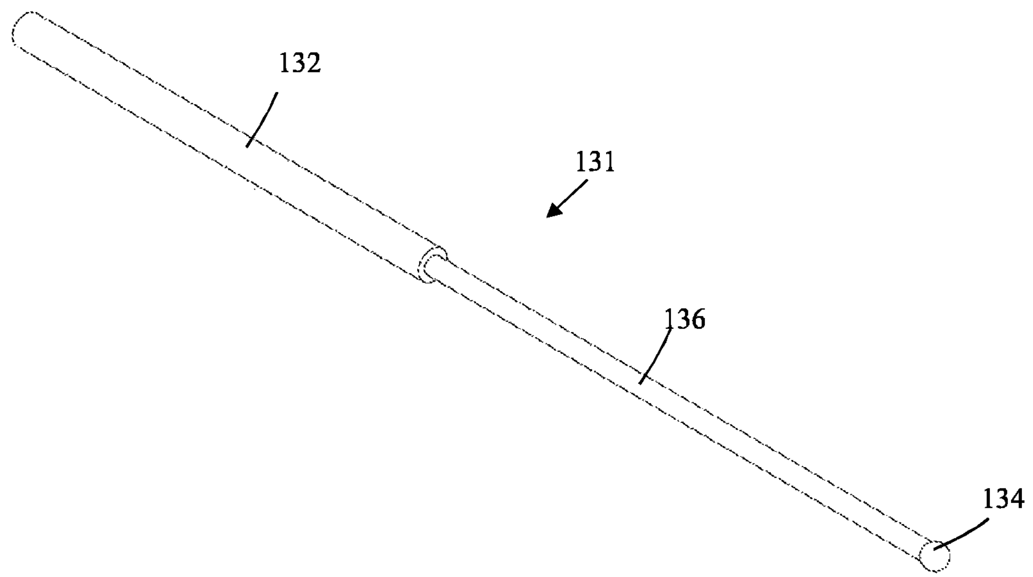
FIG. 9 is a perspective view of another embodiment of the driver.

As shown in FIGS. 8*a* and 8*b*, the driver 31 comprises a cable 32 at a proximal end and a connector 34 at a distal end. In some embodiments shown in FIG. 9, the driver 30 further comprises a wire 136 between the cable 132 and the connector 134. In an embodiment, the diameter of wire 136 is smaller than that of the cable 132 to allow the connector 134 to lock into the release portion 14. The connector 34 is configured to interface with release portion 14 in a manner to have rotational control over the clip 10 so that it may be disposed as desired.

Figure 10:
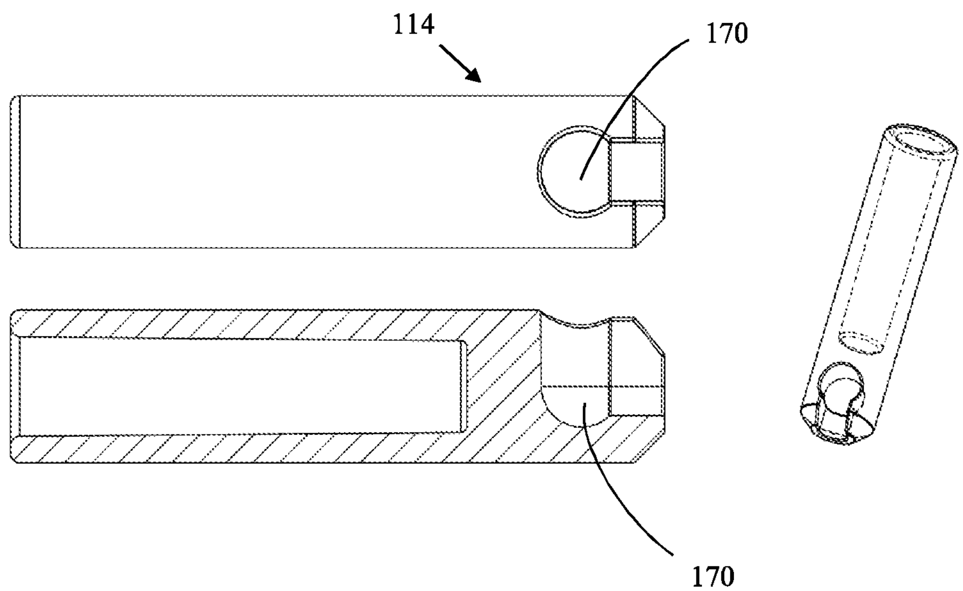
FIG. 10 shows an enlarged perspective view, an enlarged top view and an enlarged front view of the proximal release portion of a clip, which corresponds to the driver in FIG. 9.
Figure 11:
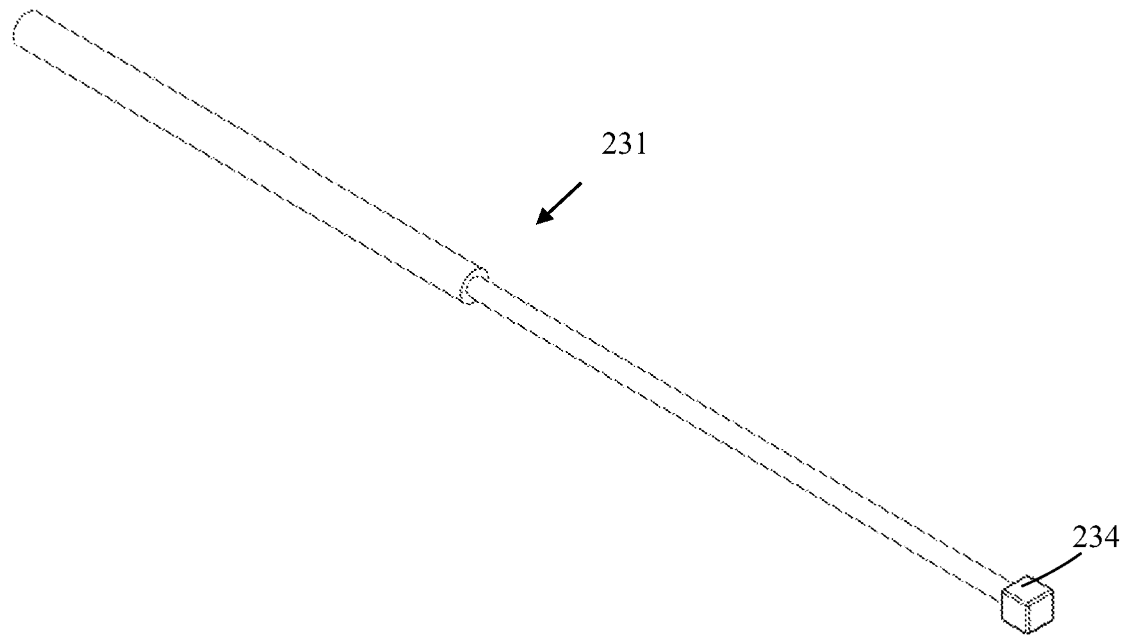
FIG. 11 is a perspective view of another embodiment of the driver.
Figure 12:
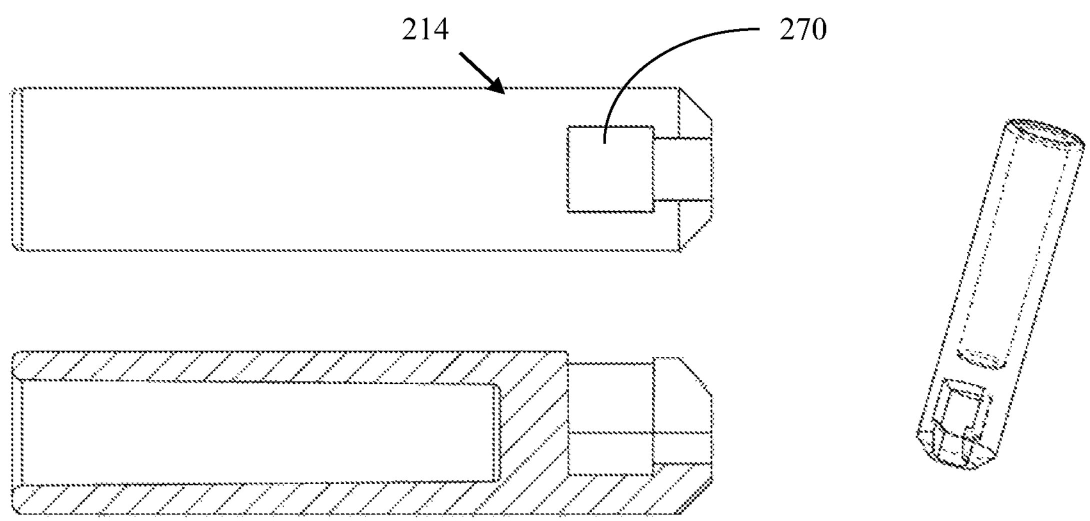
FIG. 12 shows an enlarged perspective view, an enlarged top view and an enlarged front view of another proximal release portion of a clip, which corresponds to the driver in FIG. 11.

Turning back to FIG. 2, the release portion 14 of the clip 10 is removable and coupled with the connector 34 of the driver 30. In some embodiments, the release portion 14 comprises a receiving chamber 70 with at least one side opening from the proximal end of the clip 10. In some embodiments, the connector 34 is a T-like shape cylinder shown in FIGS. 8*a* and 8*b*. The receiving chamber 70 is a T-like shape chamber and is capable to receive the T-like shape connector 34. In some embodiments, the connector 134 is a ball shown in FIG. 9. The receiving chamber 170 is a ball-like shape chamber shown in FIG. 10 and is capable to receive the ball connector 134. In some embodiments, the connector 234 is a cube shown in FIG. 11. The receiving chamber 270 is a cube-like shape chamber shown in FIG. 12 and is capable to receive the cube connector 234.

Figure 13:
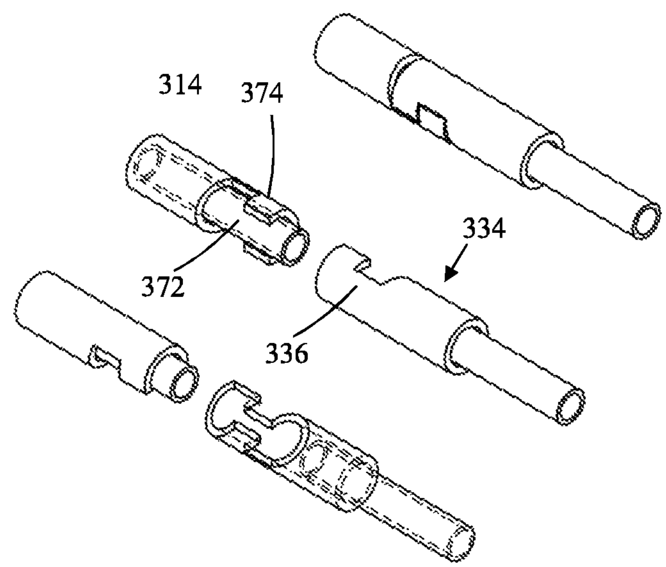
FIG. 13 is enlarged perspective views of the releasing portion of another embodiment of the clip and the connecter of driver.

In some embodiments as shown in FIG. 13, the connector 334 and the release portion 314 can be interlock connectors such as, but not limited to, hand shake connectors. The release portion 314 comprises a stabilizing arm 372 and a tab 374. The connector 334 comprises a pocket 336. The pocket 336 can rest on the stabilizing arm and interlock with the tab 374. The lock can be released when needed. A person skilled in the art should reasonably understand that the configurations of the connectors 334 and the release portion 314 are interchangeable.

A person skilled in the art should reasonably understand that the locking mechanism may be other known designs or configurations besides the above described embodiments.

Figure 14:
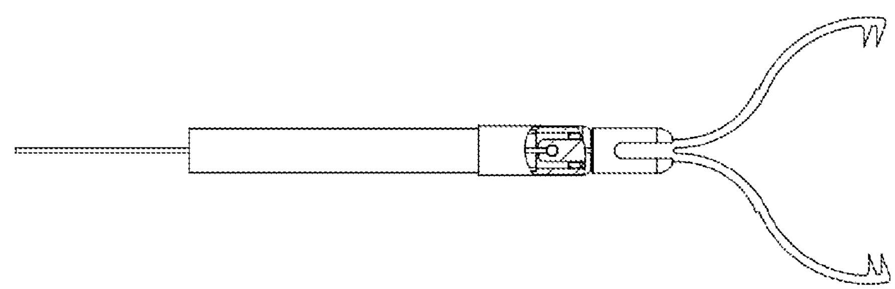
FIG. 14 shows a front view of another embodiment of the clip assembly and the driving assembly of the present subject matter.
Figure 15:
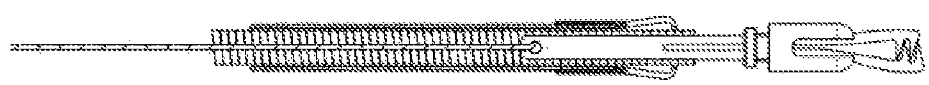
FIG. 15 shows a cross-sectional view of the clip assembly and the driving assembly shown in FIG. 14 in a fully closed position.
Figure 16:
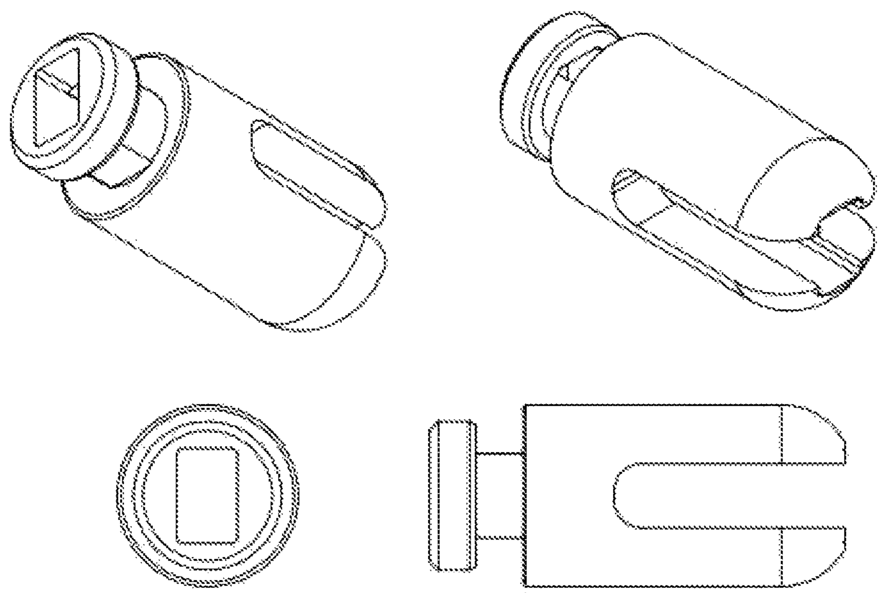
FIG. 16 shows various views of the collar shown in FIG. 14.

In an alternative embodiment of the driving assembly shown in FIGS. 14-16, the driving assembly further comprises a coupler. The coupler is disposed at the distal end of the outer sheath. The coupler is configured to removably couple to the collar. The coupler is configured to retain the collar during multiple open/close cycles while maintaining rotatability of the clip assembly. In some embodiments, a proximal end of the collar comprises a groove. A distal end of the coupler comprises an edge configured to be engageable to the groove. The edge comprises a plurality of petals that can spread apart. When the pusher tube is advanced within the coupler, the pusher tube forces the collar to be disengaged from the coupler. The driving assembly may then be advanced to aid in the detachment of the clip assembly. In this embodiment, the clip 10 is withdrawn into the collar 20 in order to engage the engagement portions 56, 66 and is not utilizing the outer sheath 42 as previous embodiments have described.

A person skilled in the art should reasonably understand that the driving assembly may be other known designs or configurations besides the above described embodiments.

Referring to FIGS. 1*a* and 1*b*, in an embodiment when a medical personnel is applying the clip assembly to a patient, the following steps may apply: 1) expose the clip at its open position; 2) adjust the driver to align the engagement portions to a treatment area; 3) the clip retracts into the outer sheath or collar to close the clip, which allows for a pre-load on the arms and increases its ability to grip the tissue; 4) push the pusher tube to move the collar passed the retention mechanism so that the clip at its fully closed position; 5) pull the outer sheath and the pusher tube back; 6) release the driver from the clip.

Referring to FIGS. 14 and 15, in an embodiment, when a medical personnel is applying the clip assembly to a patient, the following steps may apply: 1) expose the clip at its open position; 2) adjust the driver to align the engagement portions to a treatment area; 3) the clip retracts into the collar to close the clip, which allows for a pre-load on the arms and increases its ability to grip the tissue; 4) push the pusher tube to advance the collar out of the coupler and past the retention fins on the clip to lock the clip closed and allow for release of the clip from the driver.

Figure 17A:
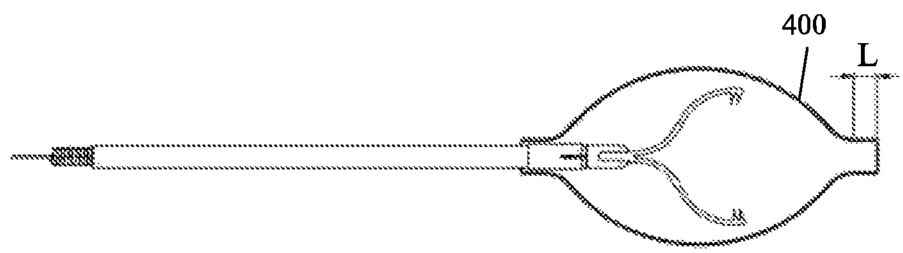
FIGS. 17*a* and 17*b* show front views of an introducer of the present subject matter.
Figure 17B:
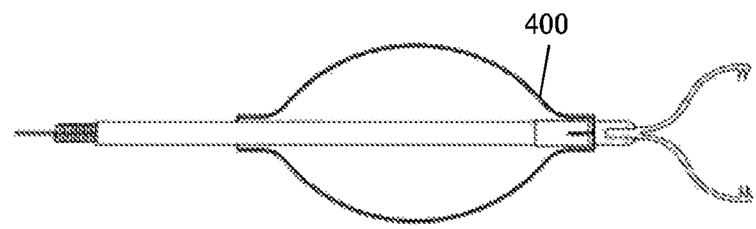

The present subject matter further describes an introducer shown in FIGS. 17*a*-17*b*. The introducer comprises an internal chamber with an opening at a proximal end of the introducer and an opening at a distal end of the introducer. The distal end of the introducer is configured to allow the clip assembly and the distal end of the driving assembly to pass through. The proximal end of the introducer is configured to prevent the clip assembly from passing through. Optionally, the proximal end of the introducer is configured to prevent the driving assembly from passing through. The introducer is configured to protect the clip during shipping and introduction through a biopsy valve on an endoscope. The distal end of the introducer is configured to couple into the biopsy valve. The minimum length L of the distal end of the introducer is about 5 mm. The clip assembly is configured to enter the endoscope working channel through the biopsy valve.

The internal chamber comprises an internal surface 400 adjacent to the proximal end. In some embodiments, the internal chamber is a pod shape. The clip is configured to maintain a full open state within the internal chamber. The internal surface 400 is configured to force the clip to collapse as the catheter assembly is advanced from the proximal end towards the distal end. Once the clip is fully exposed from the distal end of the introducer and out of the working channel, the clip is configured to return to its fully open state. Once the clip assembly has been detached from the drive assembly, the driving assembly can be withdrawn from the endoscope. The clip 10 may have atraumatic geometry to prevent damage to the scope while advancing trough the biopsy channel.

Figure 18:
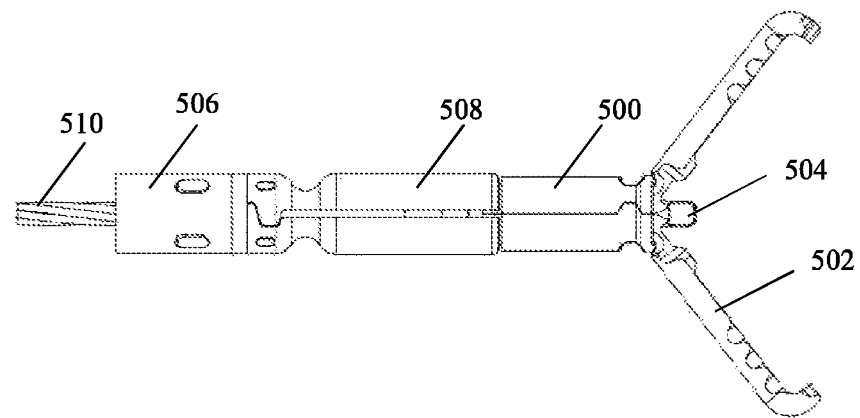
FIG. 18 shows a front view of another embodiment of a clip assembly and its driving assembly of the present subject matter in the open position.
Figure 19:
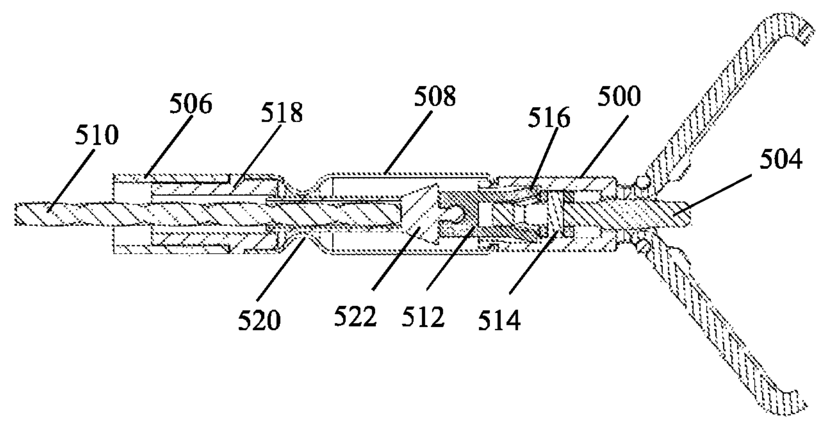
FIG. 19 shows the cross-sectional view of embodiments shown in FIG. 18 in the open position.

Referring to FIGS. 18-19, the present subject matter further discloses an alternative embodiment of the clip assembly and its driving assembly. The clip assembly comprises a base 500, a pair of jaws 502, and a switch 504. The driving assembly comprises an outer sheath 506, a coupler 508, and a driver 510.

Figure 20:
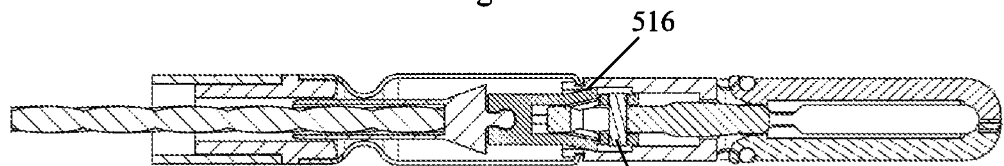
FIG. 20 shows the cross-sectional view of the embodiment shown in FIG. 18 in the closed position.
Figure 21:
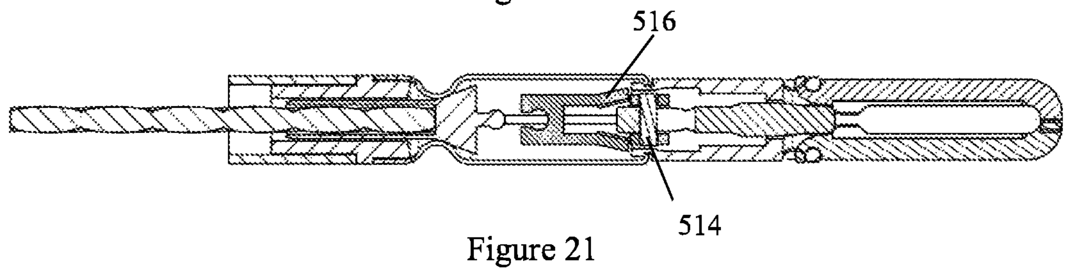
FIG. 21 shows the cross-sectional view of the embodiment shown in FIG. 18 in the stressed position.
Figure 22:
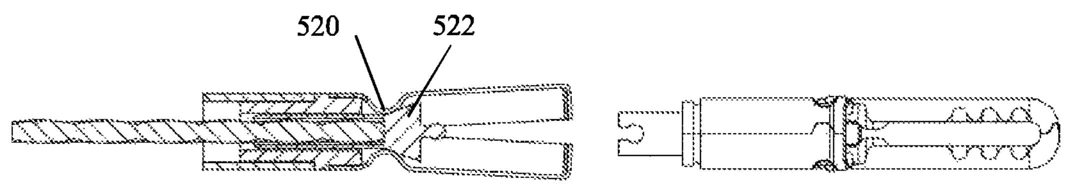
FIG. 22 shows the cross-sectional view of the embodiment shown in FIG. 18 in the released position.
Figure 23:
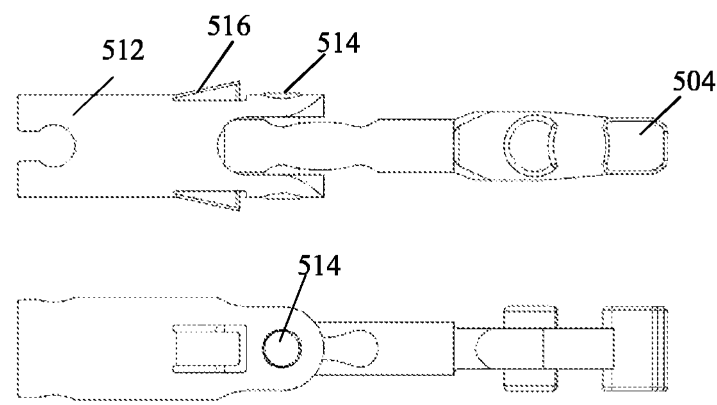
FIG. 23 shows front and top view of the switch shown in FIG. 18.
Figure 24:
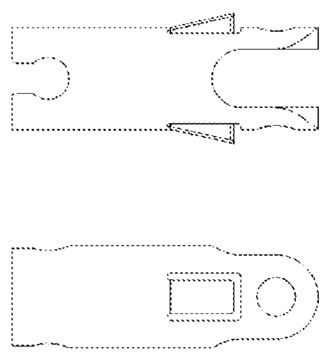
FIG. 24 shows front and top views of the release portion shown in FIG. 18.
Figure 25:
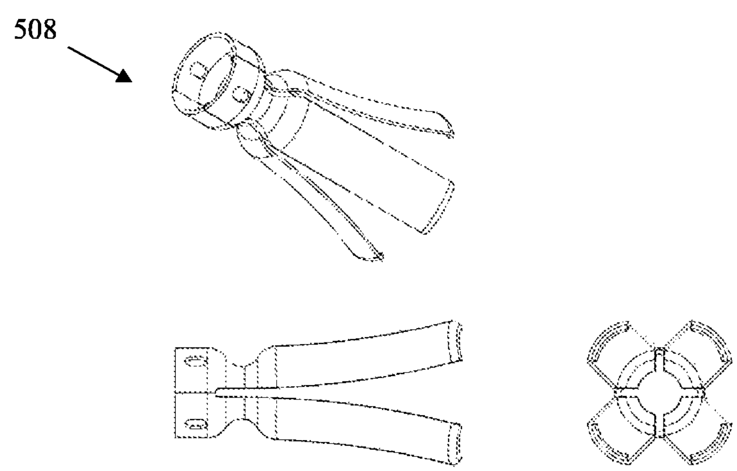
FIG. 25 shows various views of the coupler shown in FIG. 18.
Figure 26:
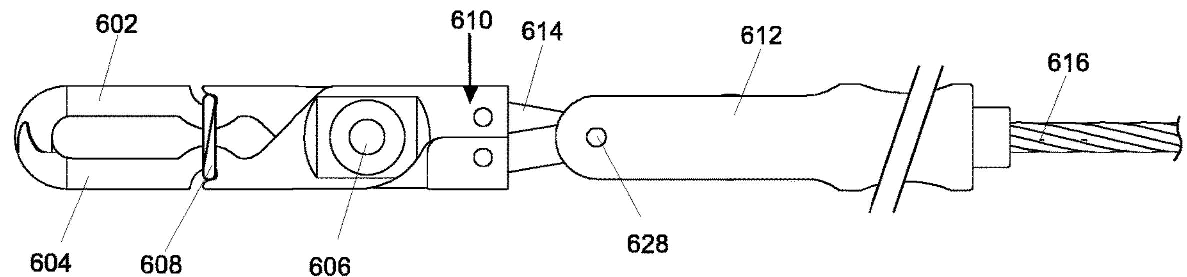
FIG. 26 is a front view of an embodiment of a clip assembly and its driving assembly of the present subject matter.
Figure 27:
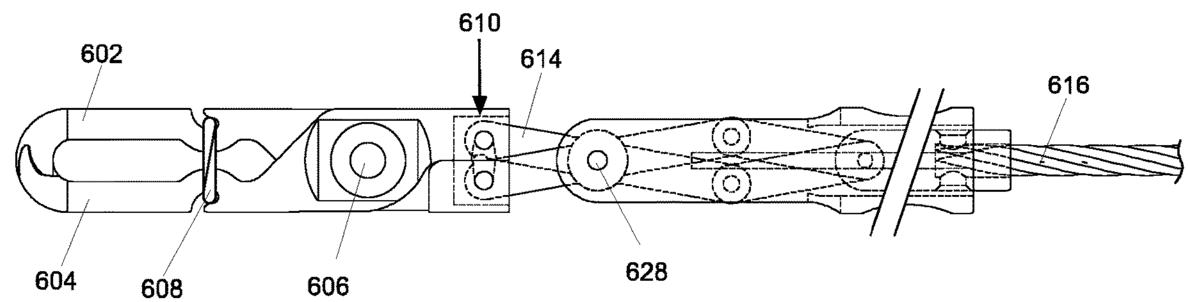
FIG. 27 is a transparent front view of the clip assembly and its driving assembly in FIG. 26.
Figure 28:
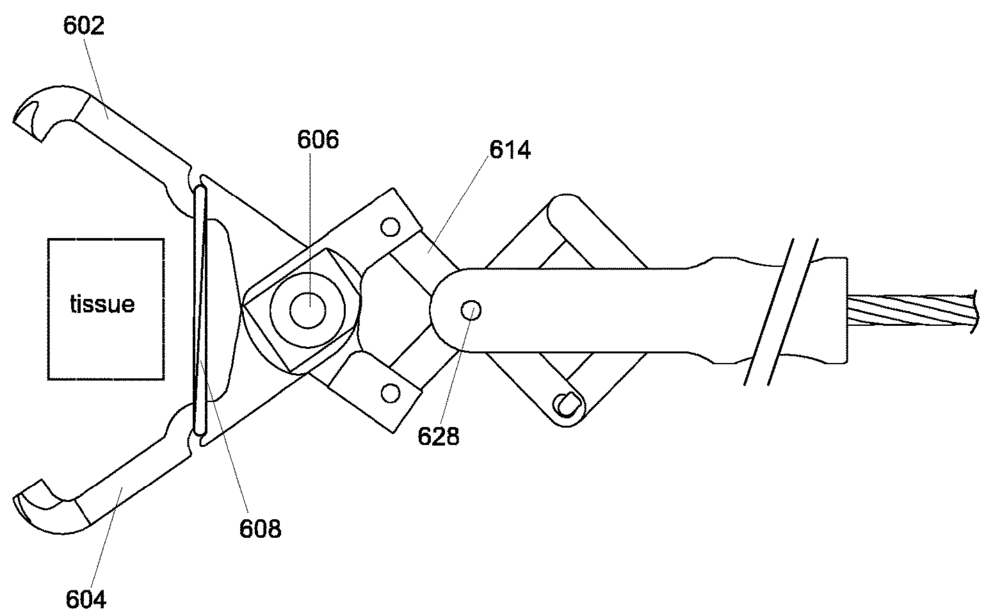
FIG. 28 is a front view of the clip assembly and its driving assembly in FIG. 26, wherein the clip assembly is opened.
Figure 29:
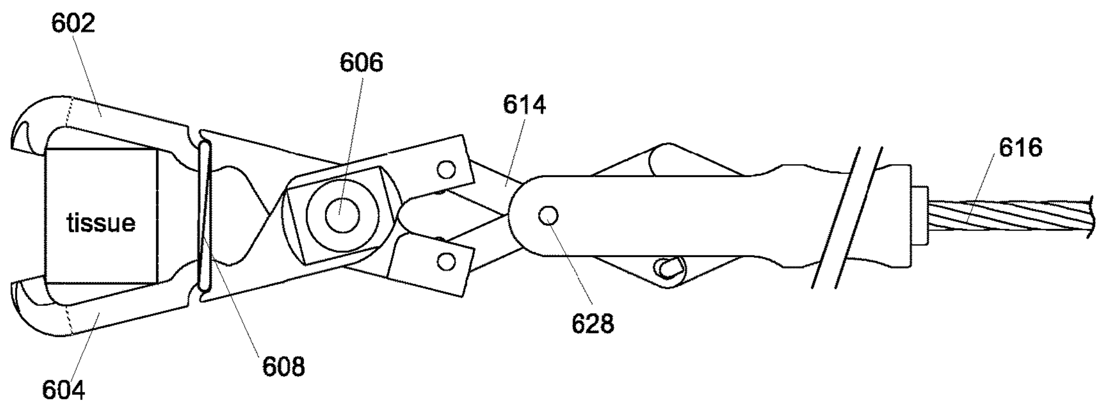
FIG. 29 is a front view of the clip assembly and its driving assembly in FIG. 26, wherein the clip assembly clips on a tissue.
Figure 30:
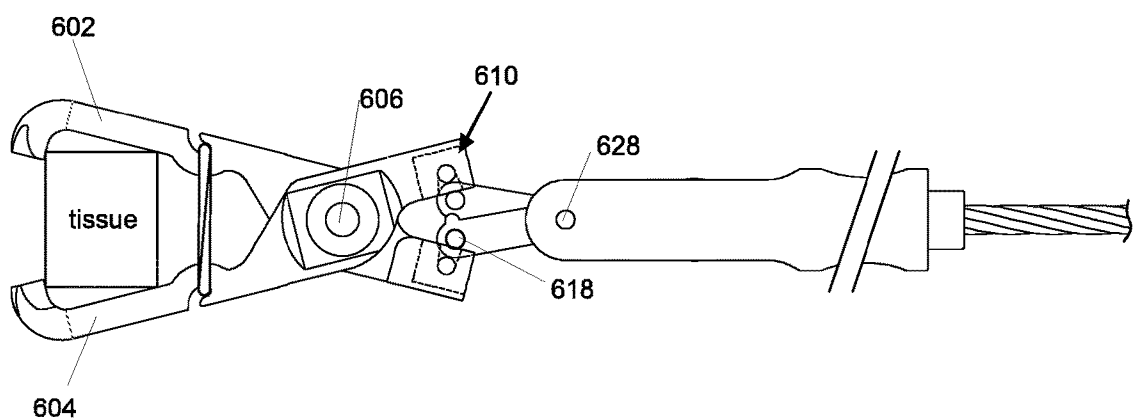
FIG. 30 is a front view of the clip assembly and its driving assembly in FIG. 26, wherein the clip assembly clips on a tissue and the driving assembly is in the process of disengaging the clip assembly.
Figure 31:
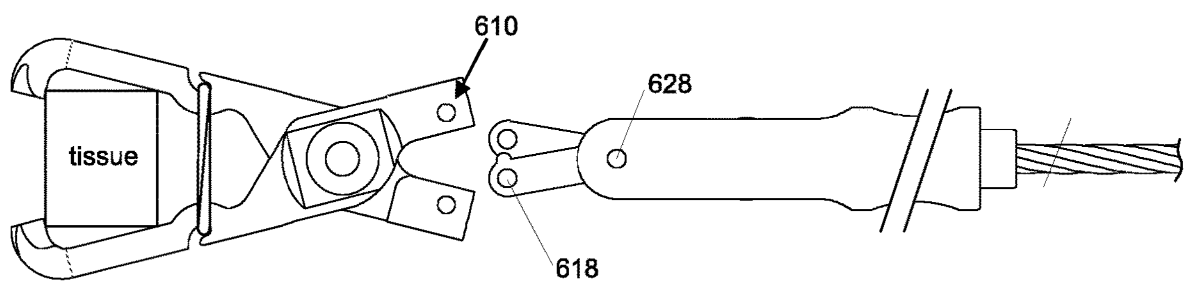
FIG. 31 is a front view of the clip assembly and its driving assembly in FIG. 26, wherein the clip assembly clips on a tissue and the driving assembly disengages the clip assembly.
Figure 32:
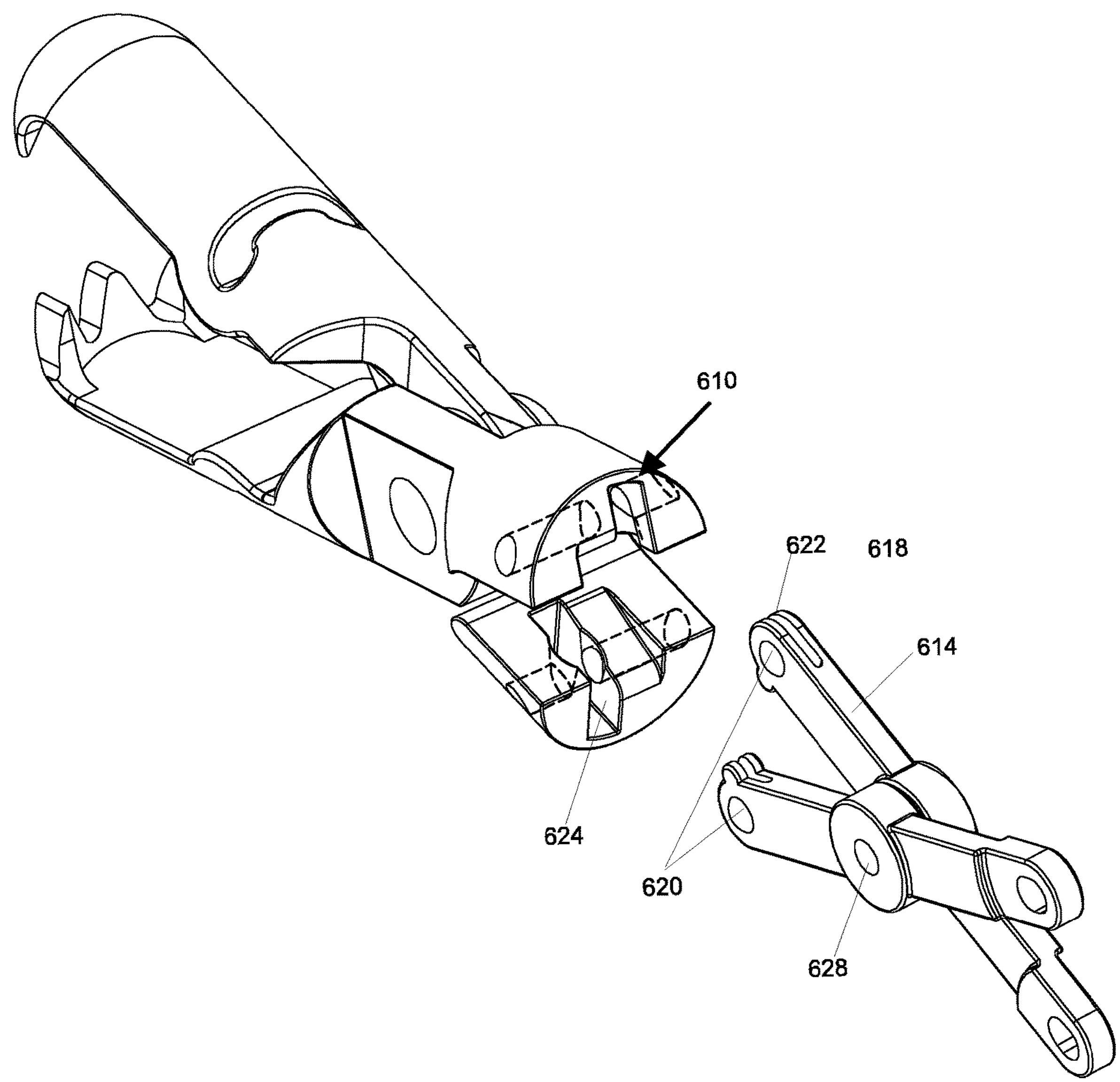
FIG. 32 is a perspective view of FIG. 31.
Figure 33:
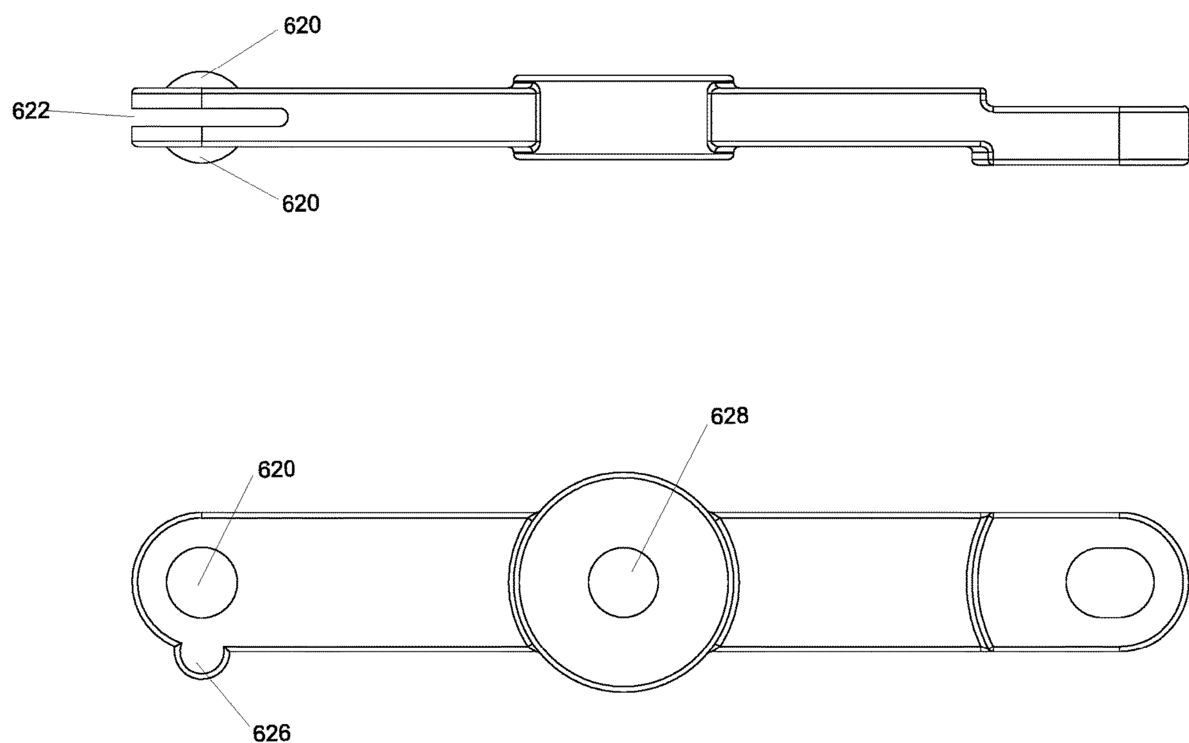
FIG. 33 shows a top view and a front view of a disengaging arm.

FIGS. 18 and 19 show the clip assembly and its driving assembly in the open position. FIGS. 20 shows the clip assembly and its driving assembly in the closed position. FIG. 21 shows the clip assembly and its driving assembly in the stressed/locked position. FIG. 22 shows the clip assembly and its driving assembly in the release/detach position. The clip assembly can freely move by the driving assembly from the open to closed position, and vice versa. Once the clip assembly enters the stressed/locked position, it cannot be opened again. The closed position allows for a pre-load on the arms and increases its ability to grip the tissue. When the clip is at the stressed/locked position, the jaws keep stressed in order to achieve a better hemostatic or other desired effect.

The base 500 is configured to hold and position the jaws 502 and the switch 504. The base 500 is configured to prevent the switch 504 from escaping from the distal end of the base 500. The base 500 comprises two halves. The jaws 502 are configured to collect and retain tissue. The jaws 502 are further configured to operably connect to a distal end of the base 500. A distal portion of the switch 504 is configured to actuate the jaws 502 between an open position and a closed position. A proximal portion of the switch 504 comprises a release portion 512. The release portion 512 is configured to removably couple with a distal end of the driver 510. An exemplary embodiment of connection between the release portion and the driver is a T-bar connection discussed in the previous embodiments. In some embodiments, the release portion 512 and the distal portion of the switch 504 are separate two pieces and are connected by a pin 514. The distal portion of the switch 504 comprises a figure-8 shaped hole. The figure-8 shaped hole comprises a distal portion and a proximal portion. When the pin 514 is deposed in the distal portion of the figure-8 shaped hole, the clip assembly can be moved between the open and closed positions. When the pin 514 is deposed in the proximal portion of the figure-8 shaped hole, the clip assembly can be locked and eventually released. A person skilled in the art should understand the figure-8 shaped hole is not necessarily a through-hole and can be a slot. In some embodiment, the figure-8 shaped hole is deposed at the release portion 512, instead of the distal portion of the switch 504. A person skilled in the art should understand that the mechanism may not be a figure-8 shaped hole and may be a geometry which achieves similar functionality.

The switch 504 further comprises a tab 516. The tab 516 is configured to be movable within the base while the jaws move between the open and closed positions. The tab is further configured to be pulled outside the base and to prevent the switch 504 to move back into the base so as to lock the jaws as stressed.

A person skilled in the art should understand that the release portion 512 and the distal portion of the switch 504 could be made in one piece so that the pin and the figure-8 shaped hole can be eliminated. In some embodiment, the connection portion between the release portion 512 and the distal portion of the switch 504 is made of elastic materials so that it achieves the similar effects of the figure-8 shaped hole, which allows the clip assembly has the opened, closed, stressed/locked, and released positions.

The coupler 508 is configured to couple with the outer sheath 506 by a barb. A person skilled in the art should understand that the coupler 508 and the outer sheath 506 can be one piece. The coupler 508 is configured to removably couple to the base 500. The coupler 508 is configured to retain the base 500 during multiple open/close cycles while maintaining rotatability of the clip assembly. In some embodiments, a proximal end of the base 500 comprises a groove. A distal end of the coupler 508 comprises an edge configured to be engageable to the groove. The edge comprises a plurality of petals that can spread apart. The coupler 508 further comprises a bottleneck 520. The driver 510 comprises a wedge 522. The wedge 522 is configured to push the bottleneck 520 when the driver 510 pulls back and tries to detach the clip assembly from the driving assembly. By pushing the bottleneck 520, the wedge 510 forces the petals of the coupler 508 apart. Then the edge and the groove are disengaged. The clip assembly therefore is detached.

Referring to FIGS. 26-33, the present subject matter further discloses an alternative embodiment of the clip assembly and its driving assembly. The clip assembly comprises a first jaw 602, a second jaw 604, a first pivot 606, and an elastomeric band 608. The first jaw 602 is pivotally connected to the second jaw 604 at the first pivot 606. The first jaw comprises a distal arm and a proximal arm. The second jaw comprises a distal arm and a proximal arm. Although both the first and second jaws are described as moving jaws above, a person skilled in the art should readily understand that the first jaw may be a stationary jaw.

The elastomeric band 608 connects the distal arms of the first and second jaws and allows for normally closed first and second jaws. In some embodiments, the elastomeric band connects between the proximal arms of the first and second jaws. In some other embodiments, one elastomeric band connects between the distal arms of the first and second jaws; another elastomeric band connects between the proximal arms of the first and second jaws. The elastomeric band may be a ring around the first and second jaws, a band between the first and second jaws, or any other connection structures between the first and second jaws. In some embodiments, the elastomeric band is eliminated and the pivot comprises a common elastomeric structure so that the first and second jaws are normally closed.

Each proximal end of the first and second jaws comprises a receiver 610. The receiver 610 is configured to removably receive the driving assembly so that the driving assembly may drive the clip assembly to be opened or closed.

The driving assembly comprises an outer sheath 612, a fork 614, and a driver 616. The fork 614 is disposed within the outer sheath 612. The distal ends of the fork 614 are extended from the distal end of the outer sheath 612. The proximal end of the fork 614 is connected to the driver 616. In one embodiment, the fork 614 is pivotally connected to the outer sheath 612 at a second pivot 628.

Each of two distal ends of the fork 614 comprises an engagement portion 618. The engagement portion 618 is configured to engage with the receiver 610 of the clip assembly. When the driver 616 is pushed towards its distal direction, the distal ends of the forks 614 are opened, and consequently the clip assembly is opened. When the driver 616 is pulled towards its proximal direction, the distal ends of the fork 614 are closed, and consequently the clip assembly is closed. The elastomeric band generates the closing force to achieve the hemostatic effect. In some embodiments, the closing force is about 150 to 400 g.

Figure 34:
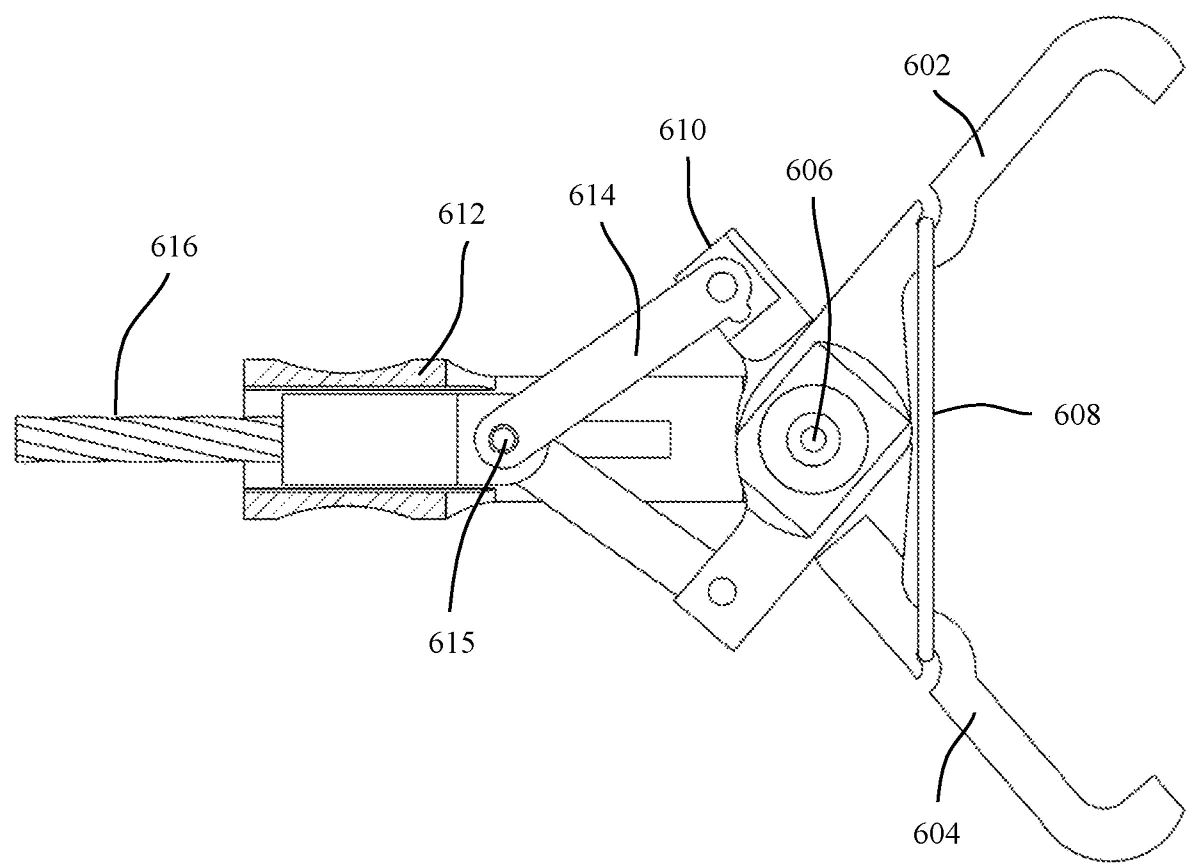
FIG. 34 shows a front view/cross-sectional view of another embodiment in the released position.

Referring to FIG. 34, the present subject matter further discloses an alternative embodiment of the clip assembly and its driving assembly. In this embodiment, a single lever arm in the fork assembly 614 is used to open the clip assembly. The first pivot 606 is connected to the outer sheath 612 until deployment. After deployment, the first pivot 606 remains with the clip assembly. Alternatively, the clip assembly may detach from the fork at a different pivot 615 allowing the linkage arms to remain loosely attached to the clip assembly. A person skilled in the art should reasonably understand that the fork (assembly) can be any known structures of which the distal ends are opened when the drive mechanism is advanced in the distal direction. A person skilled in the art should reasonably understand that detachment of the clip assembly from the fork assembly 614 and/or the receiver 610 can be achieved by various methods such as mechanical detachment or by applying electrical current to sever the joints and that detachment may be achieved at any linkage point in the fork assembly 614. In some embodiments, the driver 616 is metal and the fork assemble 614 is plastic. The driver 616 may be electrically heated and is able to melt at least a part of the fork assembly 614 to detach the fork assembly 614. In some embodiments, the outer sheath 612 is mechanically breakable. In some embodiments, the pivot 615 is mechanically breakable. In some embodiments, the driver 616 is mechanically breakable at a point near the outer sheath 612. A person skilled in the art should understand that the above described detachment may be applied to other embodiments in the present application.

In some embodiments, the fork 612 comprises asymmetrical arms. In some embodiments, the fork 612 comprises the distal arms with different length. In some embodiments, the fork 612 comprises the proximal arms with different length.

The engagement portion 618 of the fork 614 comprises a detent 620. The detent 620 may be hemispherical or any other suitable shape. The receiver 610 comprises a pocket 624 for the detent 620 to engage with. In some embodiments, the engagement portion 618 comprises a slot 622 to help the detent 620 to be compressed and to detach from the receiver 610. In some embodiments, the engagement portion 618 comprises a bump 626 to aide in detaching the receiver 610. When the clip assembly clips on a tissue, the tissue prevents the clip assembly from being fully closed. When the fork is further closed, the bump presses against the edges of the pocket 624 and aides to the disengagement.

Figure 35A:
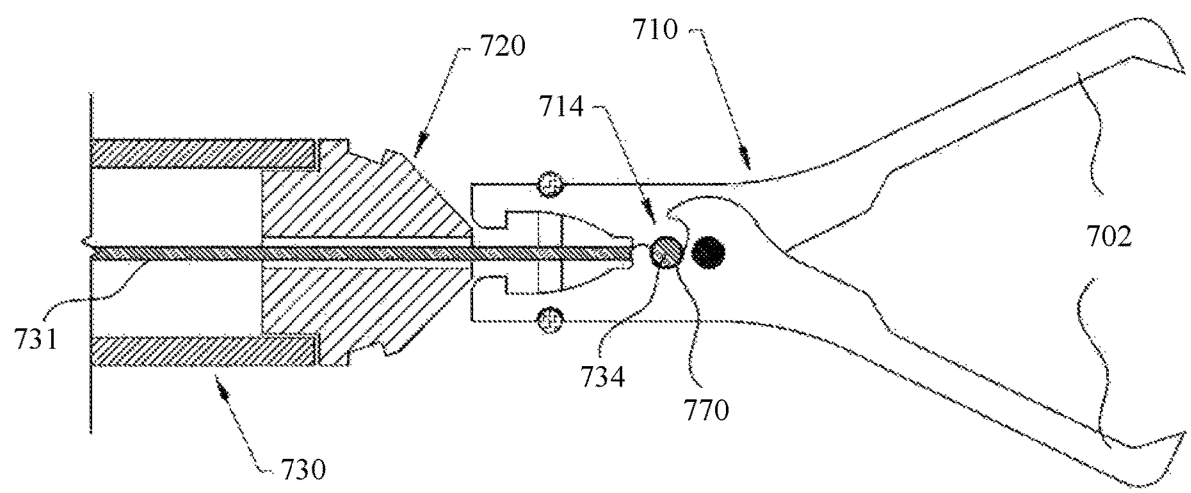
FIG. 35*a* shows a front view/cross sectional view of another embodiment of the clip assembly and the driving assembly of the present subject matter.

Referring to FIGS. 35*a, b & c,* the present subject matter further discloses an alternative embodiment of the clip assembly and its driving assembly. The clip assembly comprises a clip 710 and a locking mechanism 720, driving assembly (catheter assembly) 730, release portion 714, pair of jaws 702.

Figure 35B:
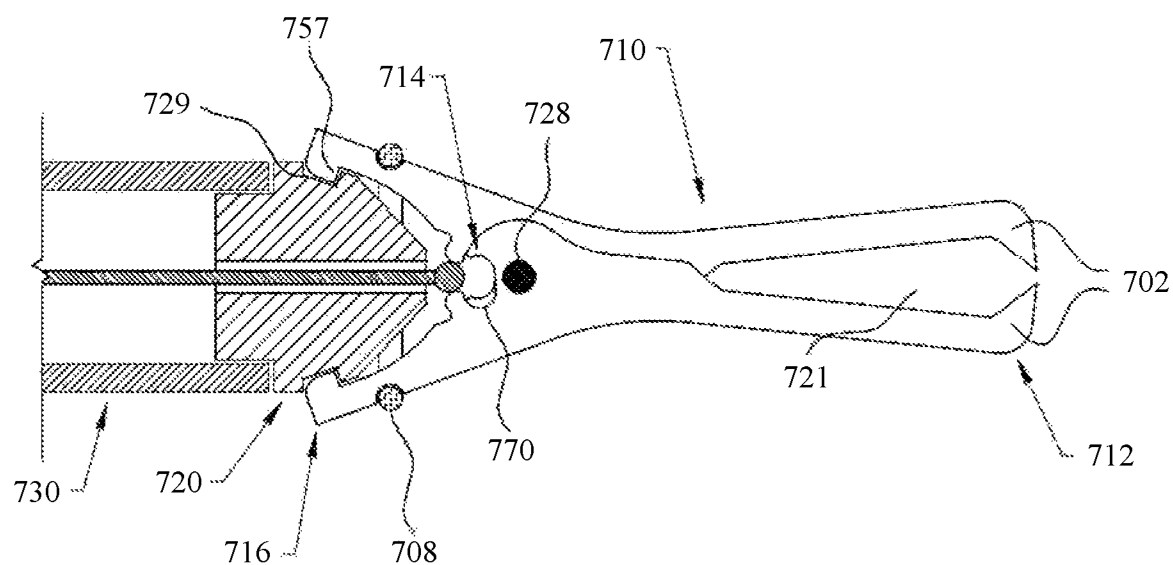
FIG. 35*b* shows a front view/cross-sectional view of the embodiment shown in FIG. 35*a* in the stressed position.
Figure 35C:
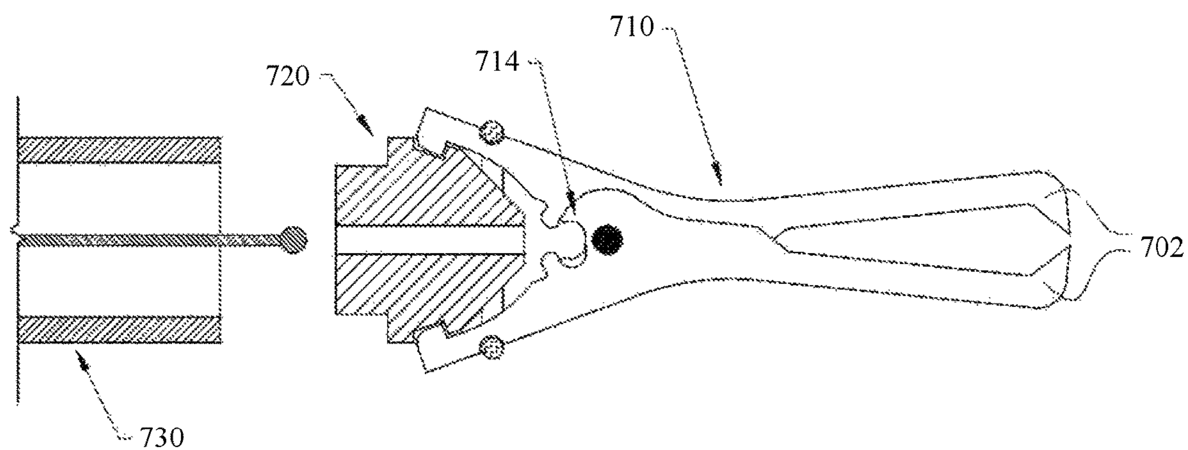
FIG. 35*c* shows a front view/cross-sectional view of the embodiment shown in FIG. 35*a* in the released position.
Figure 36:
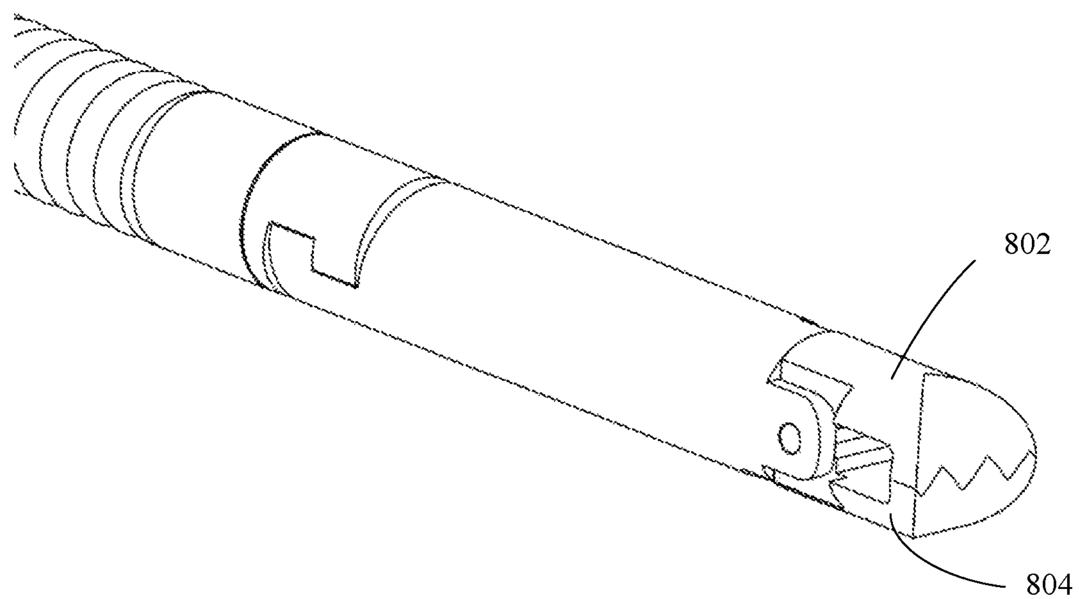
FIG. 36 shows a perspective view of another embodiment of the clip assembly and its driving assembly while the clip assembly is closed.
Figure 37:
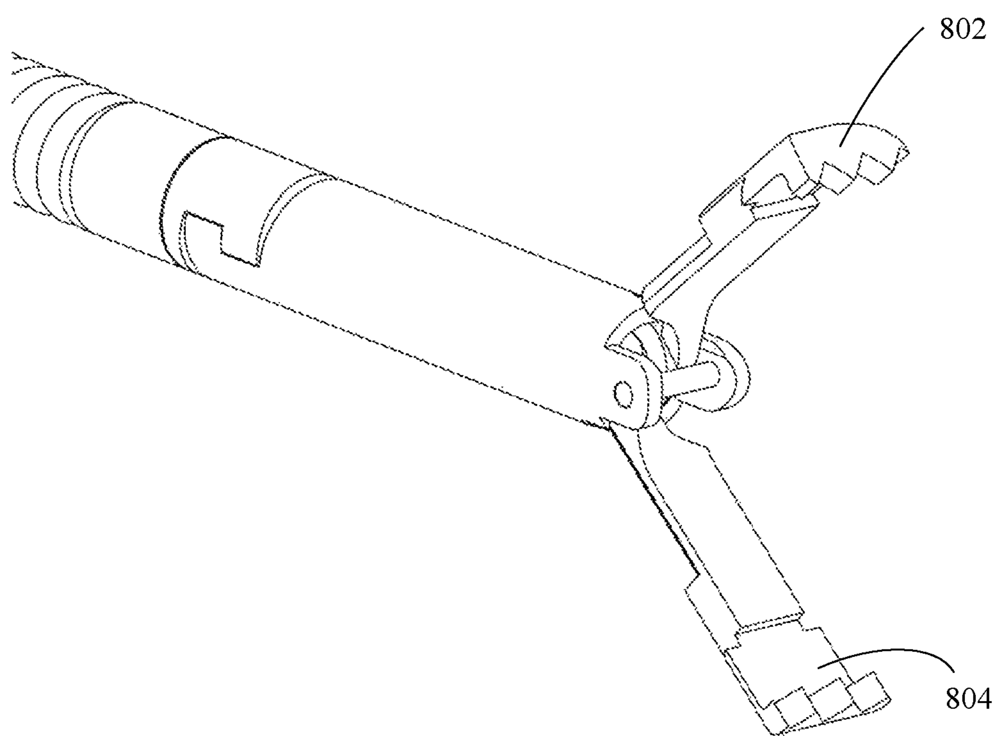
FIG. 37 shows a perspective view of the embodiment shown in the FIG. 36 while the clip assembly is open.
Figure 38:
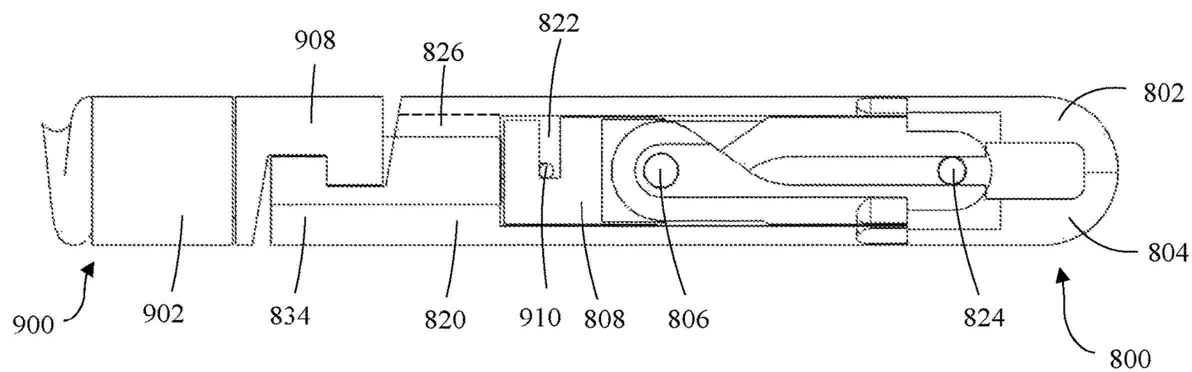
FIG. 38 shows a front view/cross-sectional view of the embodiment shown in FIG. 36.

FIG. 35*a* shows the clip assembly and its driving assembly in the open position. FIG. 35*b* shows the clip assembly and its driving assembly in the closed/stressed/locked position. FIG. 35*c* shows the clip assembly and its driving assembly in the release/detach position. The clip assembly can freely move by the driving assembly from the open to closed position, and vice versa. Once the clip assembly enters the stressed/locked position, it cannot be opened again.

The release portion 714 of the clip 710 is removably coupled with the connector 734 of the driver 731. In some embodiments, the release portion 714 comprises a receiving chamber 770 with at least one side opening from the proximal end of the clip 710. In some embodiments, the connector 734 is a T-like shape cylinder and receiving chamber 770 is a T-like shape chamber and is capable to receive a T-like shape connector. In some embodiments, the connector 734 is a ball and the receiving chamber 770 is a ball-like shape chamber and is capable to receive the ball connector 734. In some embodiments, the connector 734 is a cube shown and the receiving chamber 770 is a cube-like shape chamber and is capable to receive the cube connector 734. Those who are skilled in the art should reasonably understand that the shape of the connector 734 and the receiving chamber 770 can be any geometry which allows for a suitable connection and disengagement.

Referring to FIG. 35*b*, the jaws 702 are connected by a pivot 728. Those skilled in the art should reasonably understand that the pivot may comprise of one or more pivot points and may be a separate piece or comprised of feature within the jaws 702. The pivot 728 may be comprised of any suitable material allowing for the closure of the jaws 702. The Jaws 702 may be comprised of one or more pieces linked via the pivot 728. The pivot 728 may contain additional components necessary for the operation of the assembly.

The elastomeric band 708 connects the proximal arms of the jaws 702 and allows for normally opened positioned jaws. The elastomeric band may be a ring around the first and second jaws, a band between the first and second jaws, or any other connection structures between the first and second jaws. In some embodiments, the elastomeric band is eliminated and the pivot comprises a common elastomeric structure so that the first and second jaws are normally opened. In some embodiments, the elastomeric band is eliminated and the jaws are mechanically connected to the locking mechanism allowing for controlled opening and closing of the jaws.

When closing, the driving assembly 730 causes the locking mechanism 720 to spread the proximal end of the clip assembly 710 thereby bringing the grab portion 712 of the jaws 702 together creating of a tissue entrapment area 721. This is accomplished via the pivot 728 which causes the connector 734 to disengage from the receiving chamber 770 of the release portion 714. This disengagement may be comprised of a break-away feature such that the connector 734 releases from receiving chamber 770 after the clip assembly 710 is in its stressed/locked state. In some embodiments, the locking mechanism 720 comprises of a retention pocket 729 on the outer portion. The retention pocket 729 interlocks with the retention fins 757 of the retention mechanism 716 thus locking the clip 710 in a closed position. A person skilled in the art should reasonably understand that the locking mechanism may be other known designs or configurations besides the above described embodiments which accomplish the task of spreading the proximal arms of the jaws 702.

Referring to FIG. 35*c*, once the clip assembly 710 is in a stressed/locked position, the driving assembly 730 disengages from the locking mechanism 720.

Referring to FIGS. 36-40, the present subject matter further discloses an alternative embodiment of the clip assembly 800 and its driving assembly 900. The clip assembly 800 comprises a first jaw 802, a second jaw 804, a pivot 806, a release portion 808, and a housing 820. In one embodiment, the first jaw 802 and the second jaw 804 are pivotally connected to the pivot 806. A person skilled in the art should understand that the pivot 806 may be removably attached to or a part of the first jaw 802, the second jaw 804, a release portion 808, or any combination thereof. The housing 820 comprises an internal channel 822. At least a portion of both the first jaw 802 and the second jaw 804 is disposed within the internal channel 822. The first jaw 802 and the second jaw 804 are configured to move along with the internal channel 822 between a fully closed position and a fully opened position. When the driving assembly 900 or a driver of the driving assembly 900 is pushed towards its distal direction, the first jaw 802 and the second jaw 804 open. When the driving assembly 900 or the driver of the driving assembly 900 is pulled towards its proximal direction, the first jaw 802 and the second jaw 804 close. Although both the first and second jaws are described as moving jaws above, a person skilled in the art should readily understand that the first jaw may be a stationary jaw. A person skilled in the art also should understand that the clip assembly 800 may comprise more than two jaws.

In some embodiments, the housing 820 comprises a distal stopper 824. The distal stopper 824 is disposed at or near the distal end 836 of the internal channel 822. In some embodiments, the distal stopper 824 is a pin removably passing through the housing 820. The distal stopper 824 is configured to force the first jaw 802 and the second jaw 804 fully open when the release portion moves to its most distal position. The distal stopper 824 is also configured to prevent the first jaw 802 and the second jaw 804 from completely falling out of the housing 820. The distal stopper 824 is also configured to prevent the first jaw 802 and the second jaw 804 from crossing the center plane bisecting the two arms.

In some embodiments, the housing 820 comprises a proximal stopper 826. The proximal stopper 826 is disposed at or near the proximal end 834 of the internal channel 820. In some embodiments, the proximal stopper 826 is a ring attached to the internal channel 822. The proximal stopper 826 may prevent the release portion 808 from falling out of the housing 820. The proximal stopper 826 may provide a leverage surface other than the jaws to pull against when trying to dislodge the T-tag. Stresses can be balanced between that proximal stopper or the step in the jaws depending on the position of this step. In some embodiments, all force could be on the proximal stopper. In some embodiments, all force could be on the jaws. In some embodiments, all force could be shared between the proximal stopper and the jaws.

At least a portion of the release portion 808 is proximal to the first jaw 802 and the second jaw 804. In some embodiments, the release portion 808 is pivotally connected to the pivot 806. In some embodiments, the release portion 808 is fixed to the pivot 806. In some embodiments, the release portion 808 is fixed to either arm or both arms. In some embodiments, the first jaw 802 and the second jaw 804 are disposed at each side of at least a portion of the release portion 808. The release portion 808 is configured to removably receive the driving assembly 900 so that the driving assembly 900 or the driver of the driving assembly 900 may drive the clip assembly 800 to be opened or closed.

In some embodiments, at the partially or fully closed positions, the first jaw 802 and the second jaw 804 achieve hemostatic effort. In some embodiments, the first jaw 802 and the second jaw 804 bite on the target tissue. The friction between at least one of the first and second jaws 802, 804 and the internal channel 822 cause the first and second jaws 802, 804 to remain closed and achieve the hemostatic effort on the bitten tissue.

Figure 41:
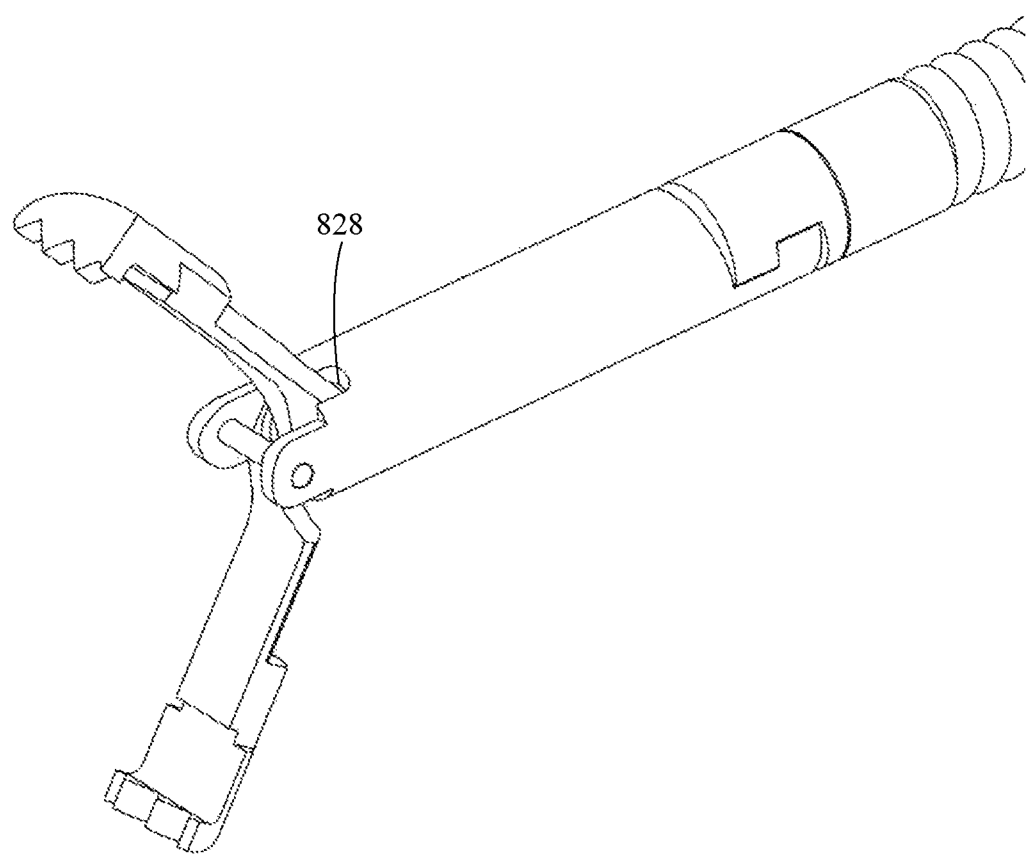
FIG. 41 shows another perspective view of the embodiment shown in the FIG. 36 while the clip assembly is open.
Figure 42:
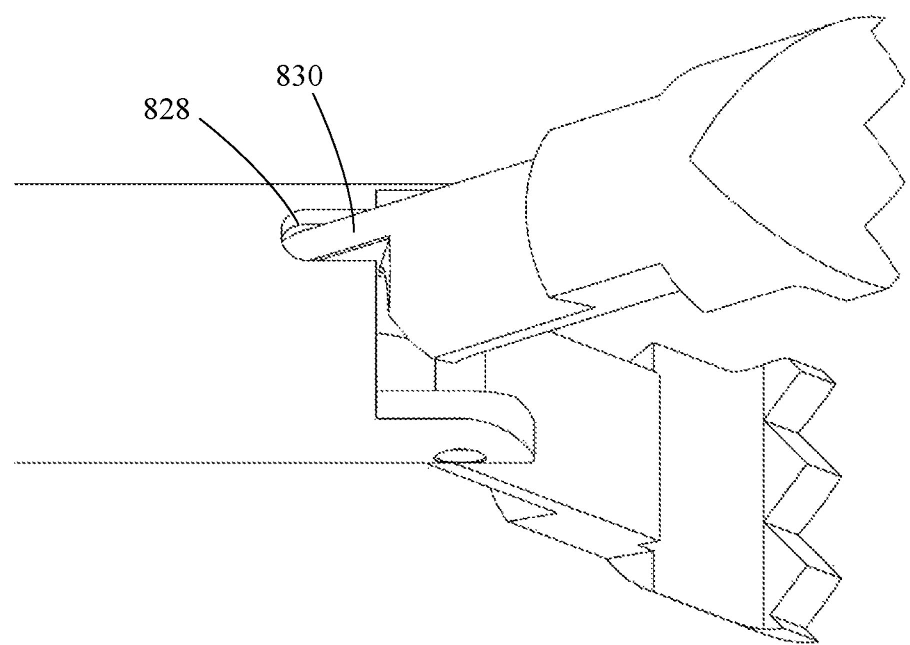
FIG. 42 shows an enlarged view a portion of the embodiment shown in FIG. 41.
Figures 43A, 43B, 43C, 43D:
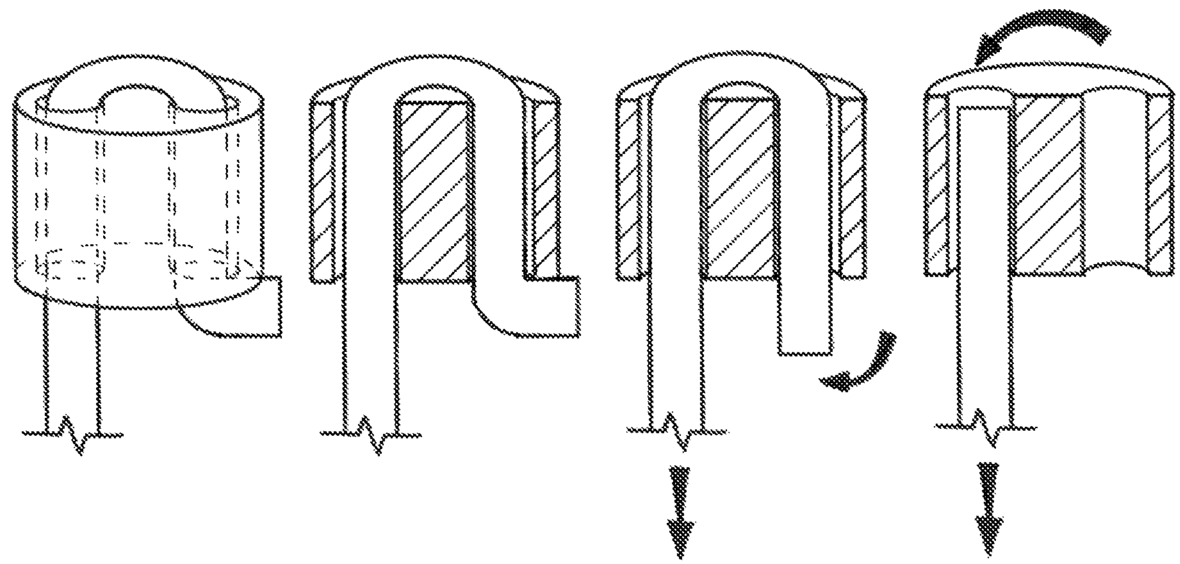
FIGS. 43*a-d* show various views of an embodiment of engagements.

Referring to FIGS. 41-42, when the clip assembly 800 is in the open position, the jaws may be able to rotate, causing misalignment or even binding which would prevent the jaws from retracting. In some embodiments, the housing 820 comprises at least one alignment slot 828. In some embodiments, the housing 820 comprises two alignment slots. The alignment slot 828 is configured to receive at least a portion of the first jaw 802 when the first jaw 802 in a non-closed position. In some embodiments, the alignment slot 828 is configured to receive an alignment rib 830 of the first jaw 802. The alignment slot 828 prevents the first jaw 802 from unintended misalignment or rotation. In some embodiments, the housing 820 comprises two alignment slots 828 for both the first jaw 802 and the second jaw 804.

Referring to FIGS. 63-68, in some embodiments, the alignment slot 828 is disposed at the internal channel 822. The alignment slot 828 is configured to receive at least a portion of the releasing portion 808. The alignment slot 828 prevents the releasing portion 808 from rotating within the internal channel 822, and therefore prevents the first and second jaws from unintended misalignment or rotation. In some embodiments, the internal channel 822 with the alignment slots 828 receives the release portion 808 with alignment ribs 830. In some embodiments, the internal channel 822 and the alignment slots 828 together form a non-cylindrical geometry, which receives a corresponding non-cylindrical geometry of the release portion 808. In some embodiments, the alignment slots 828 are disposed on the housing 820 and receive pins 832 on the release portion 808. In some embodiments, the alignment slots 828 are disposed on the housing 820 and receive the pivot 806. A person skilled in the art should understand that the slot does not need to be visible from the outside of the housing; the slot does not to be on both sides; the pins do not need to be on the both sides; and the ribs do not need to be on the both sides.

A person skilled in the art should understand the shape of the housing 820 (or the internal channel 822) can be cylinder, cuboid, diamond, or other suitable geometries, as long as the releasing portion 808 has a corresponding geometry.

Figure 39:
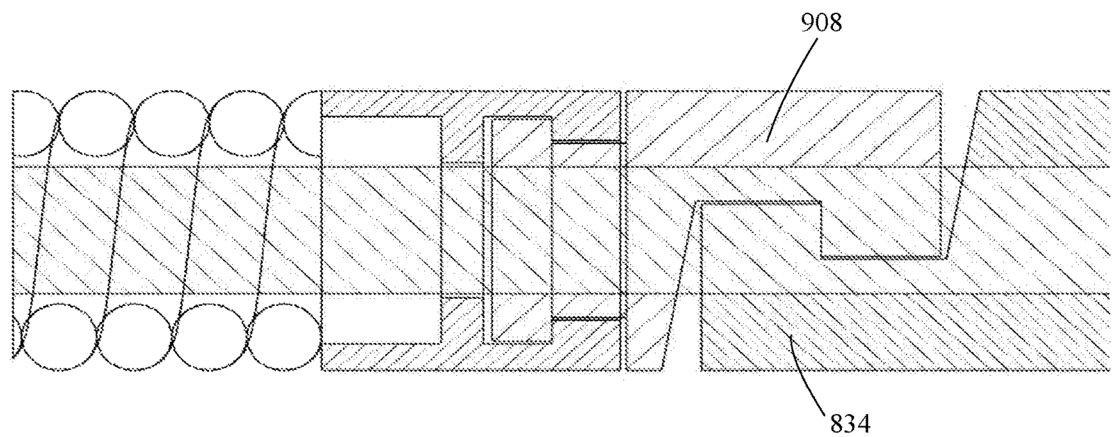
FIG. 39 shows an enlarged view of a portion of the embodiment shown in FIG. 38.

The driving assembly 900 comprises an outer sheath 902, an inner tube 904, and a driver 906. The inner tube 904 is movably disposed within the outer sheath 902. The driver 906 is movably disposed within the inner tube 904. The driver 906 removably connects to the release portion 808 to form a driving engagement. The driver 906 is configured to move between its distal direction and its proximal direction to control the clip assembly 800 between open and closed. In some embodiments of the driving engagement, upon a predetermined pull force, the driver 906 separates from the release portion 808. Such predetermined pull force is larger than the force causing the clip assembly 800 closed and achieving a hemostatic effect. In some embodiments, the distal end 908 of the outer sheath 902 and the inner tube 904 form a housing engagement with the proximal end 834 of the housing 820. A person skilled in the art should understand that only one of the driving and housing engagements is needed in some embodiments of the device. Referring to FIG. 39, in some embodiments, the distal end 908 is configured to fully rotate 360 degrees without separating from the other part of the outer sheath 902. In some embodiments, an interlocking rib and channel design comprised of two opposing ledges keep the distal end from disengaging yet allowing for circular rotation.

Figure 62:
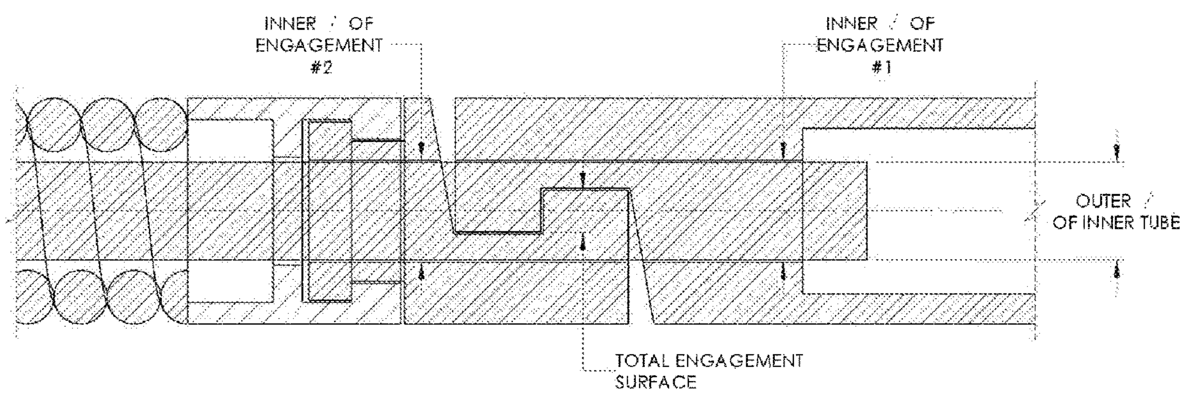
FIG. 62 shows a cross-sectional view of another embodiment of engagements.
Figure 63:
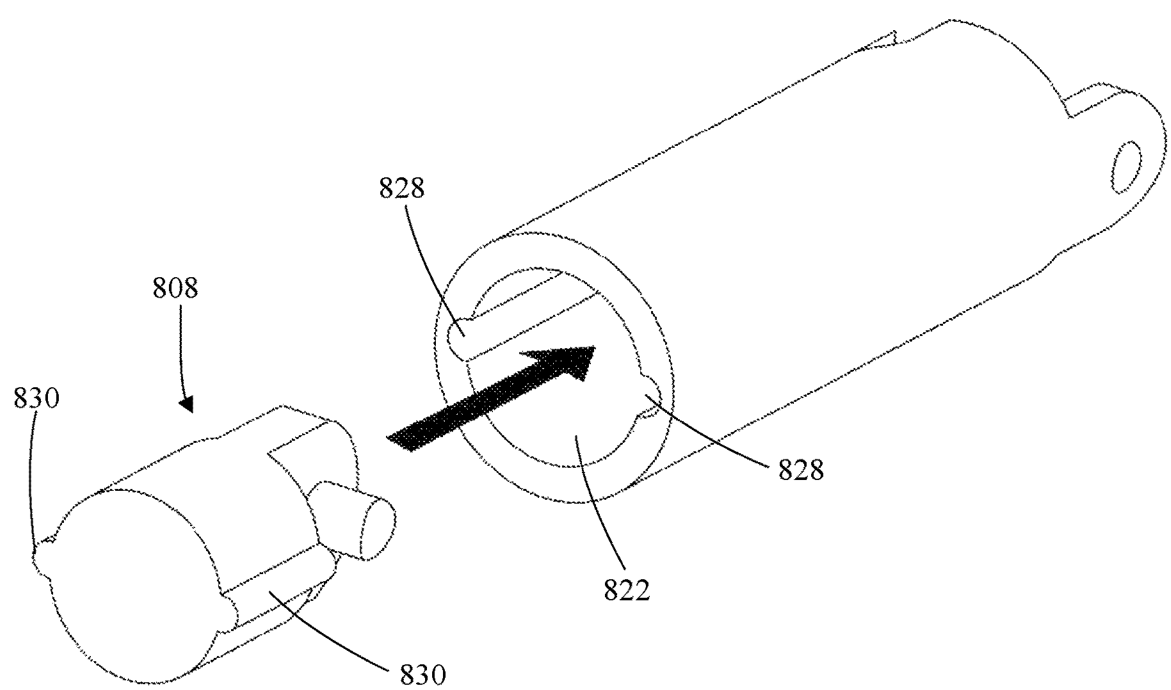
FIG. 63 shows a perspective view of another embodiment of engagements.
Figure 64:
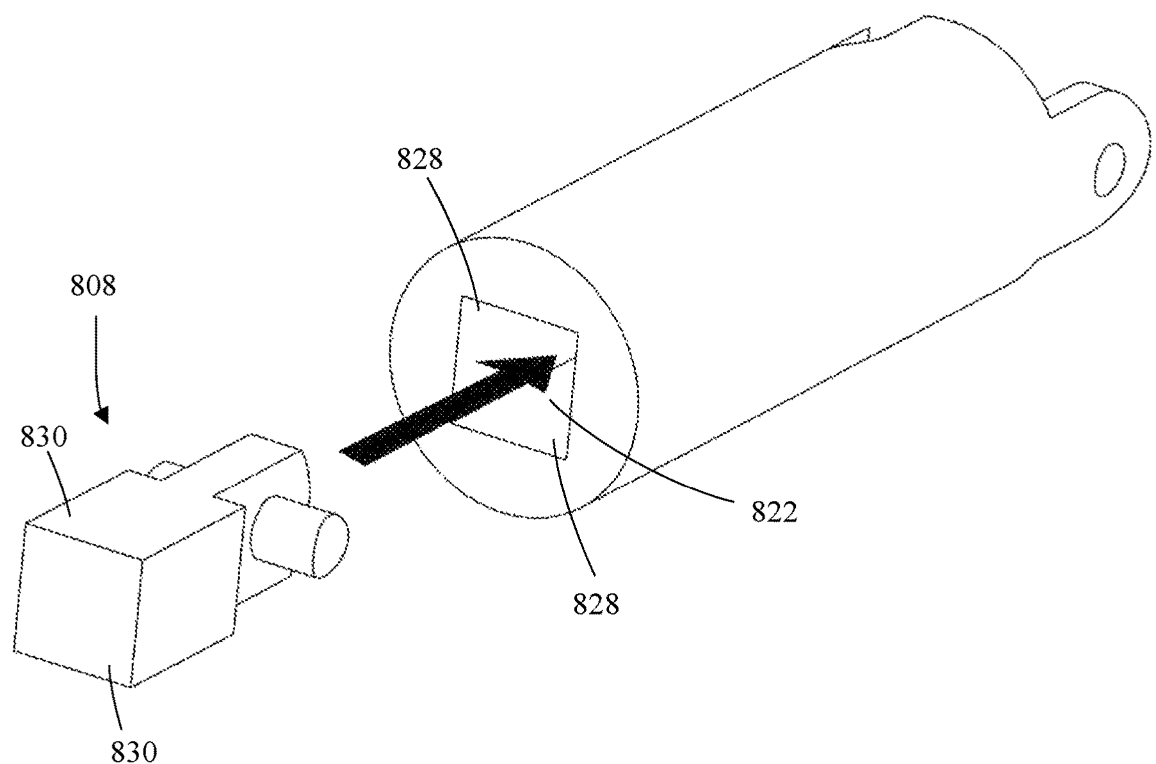
FIG. 64 shows a perspective view of another embodiment of engagements.
Figure 65:
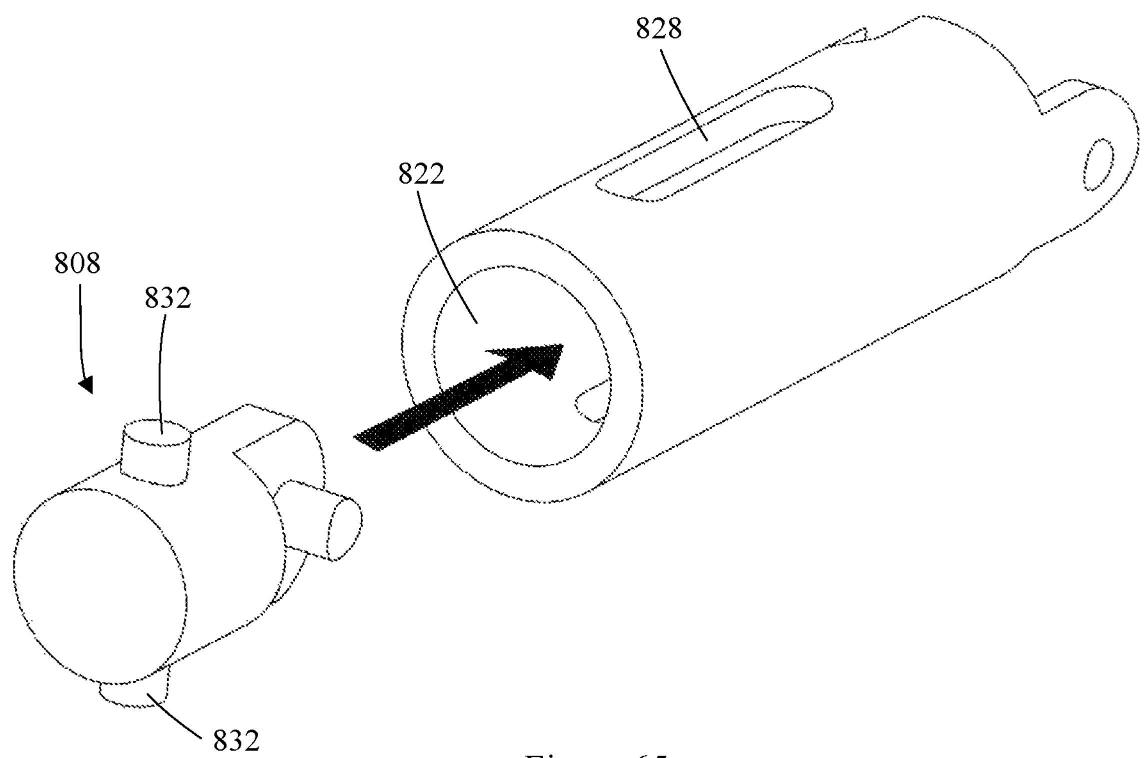
FIG. 65 shows a perspective view of another embodiment of engagements.
Figure 66:
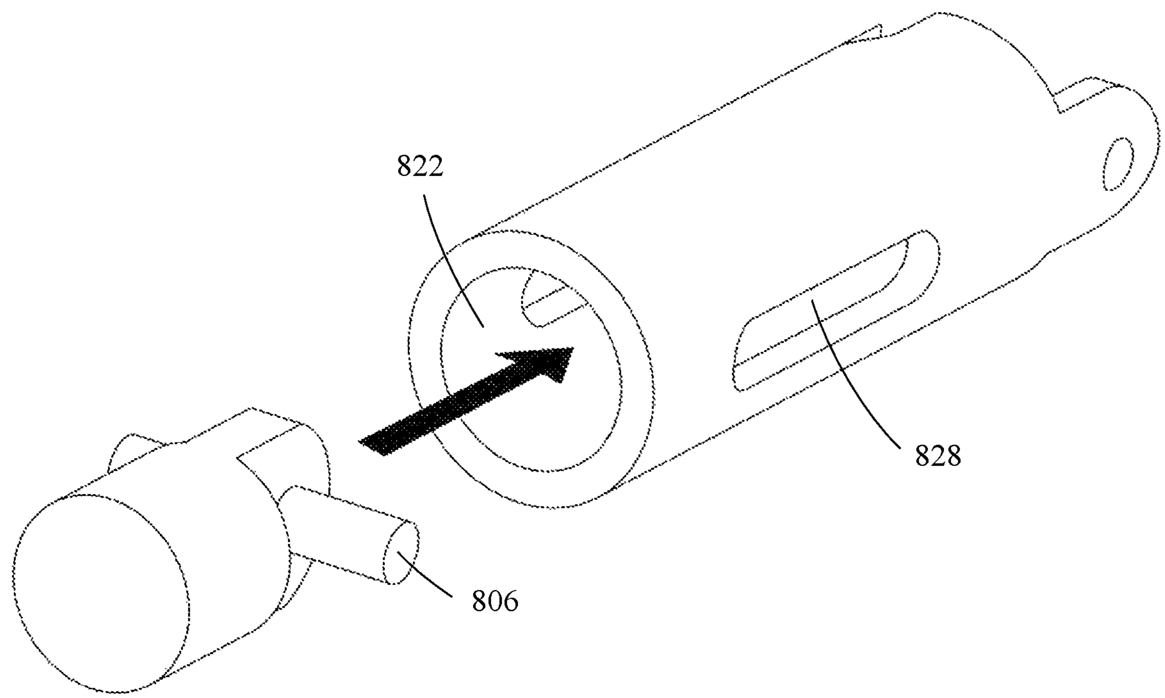
FIG. 66 shows a perspective view of another embodiment of engagements.
Figure 67:
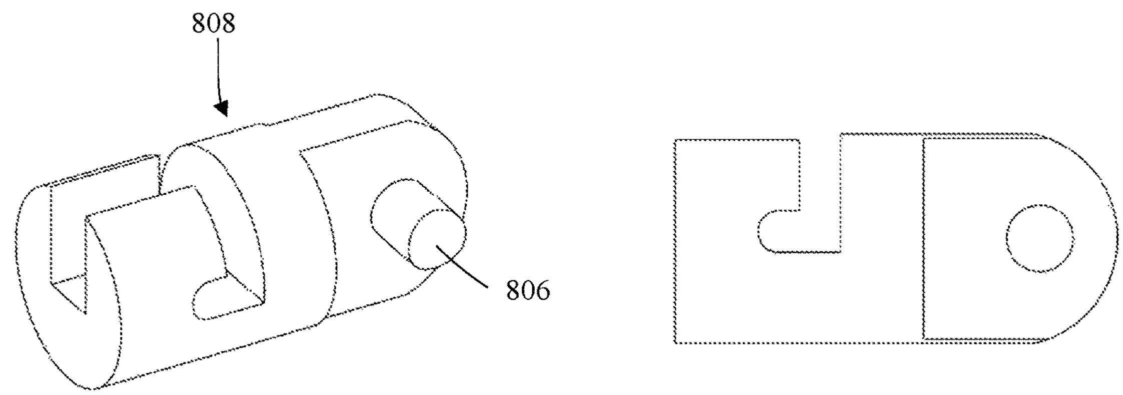
FIG. 67 shows various views of another embodiment of engagements.
Figure 68:
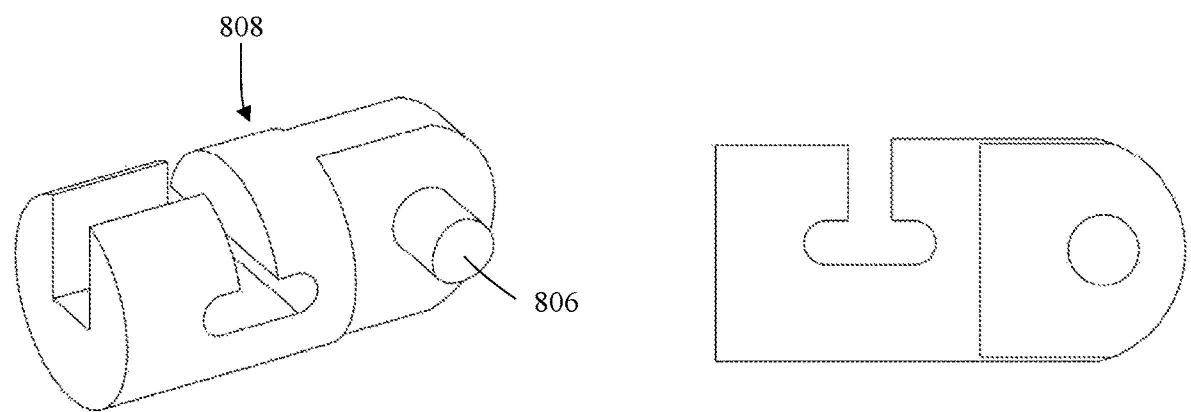
FIG. 68 shows various views of another embodiment of engagements.
Figure 69:
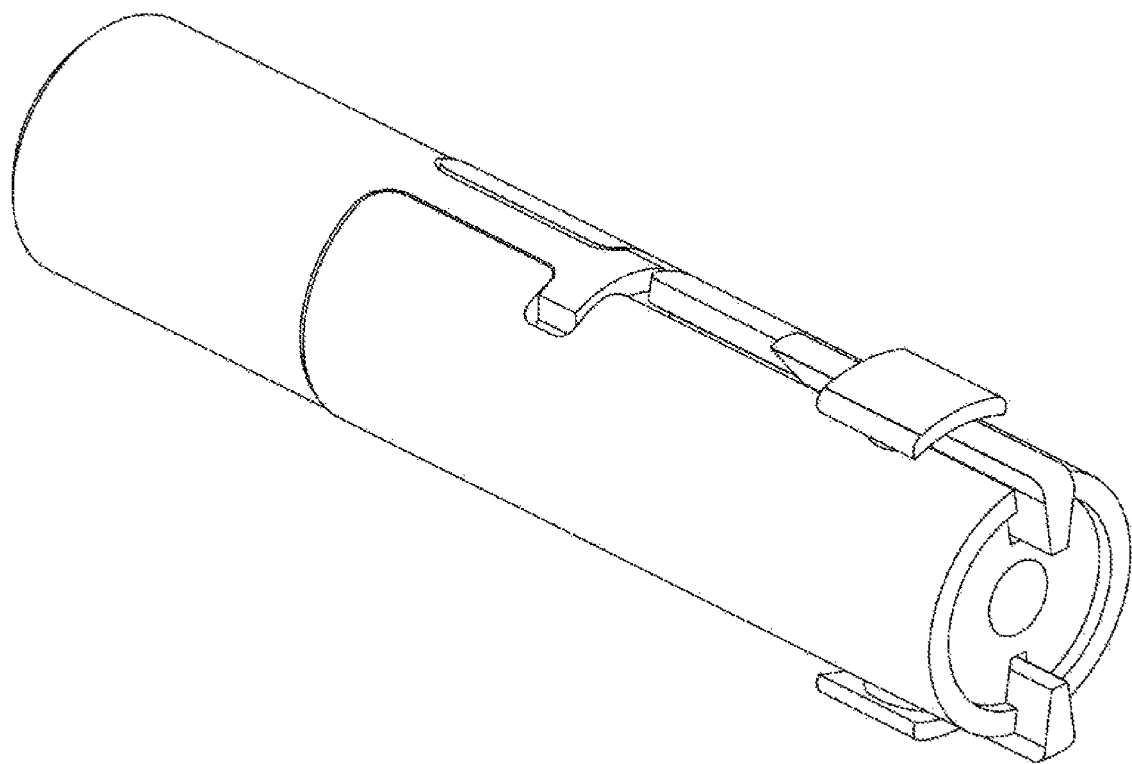
FIG. 69 shows a perspective view of another embodiment of engagement.
Figure 70A:
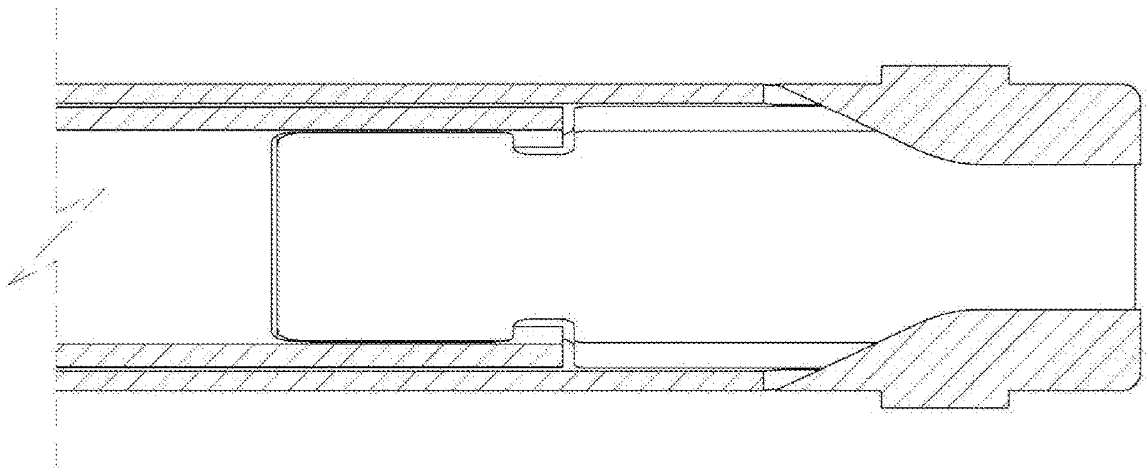
FIGS. 70*a-c* show various views of the engagement shown in FIG. 69.
Figure 70B:
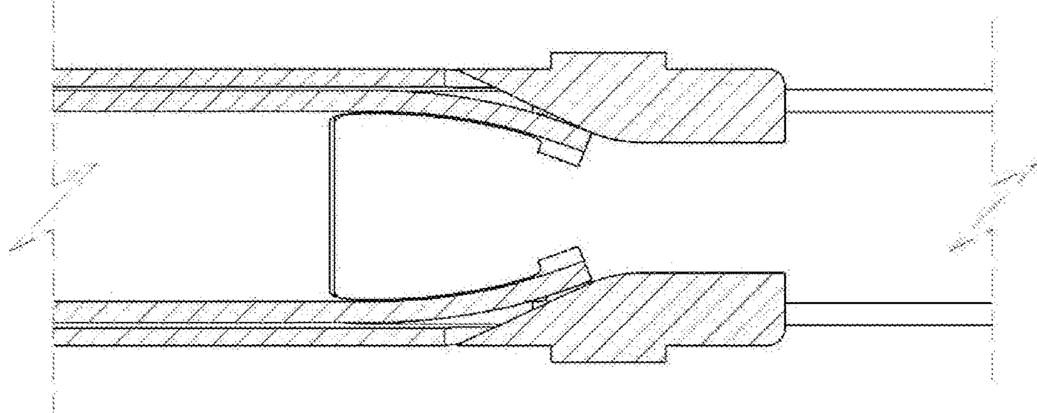
Figure 70C:
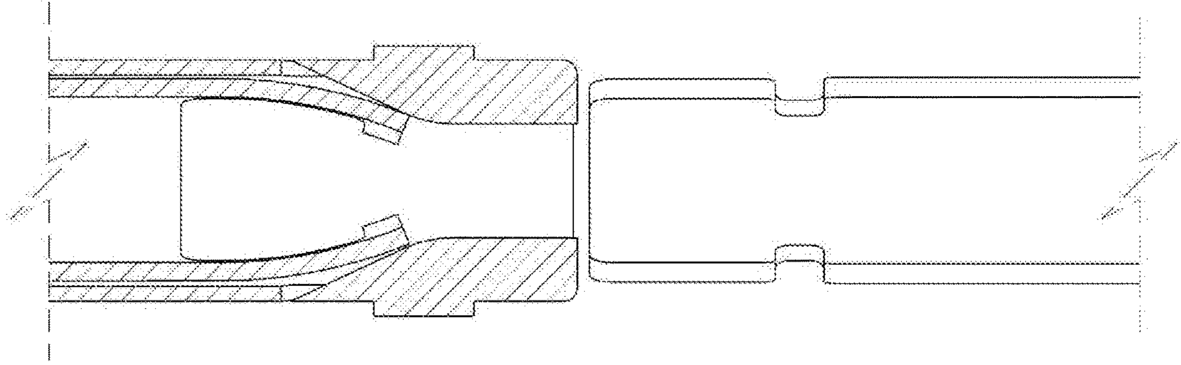
Figure 71A:
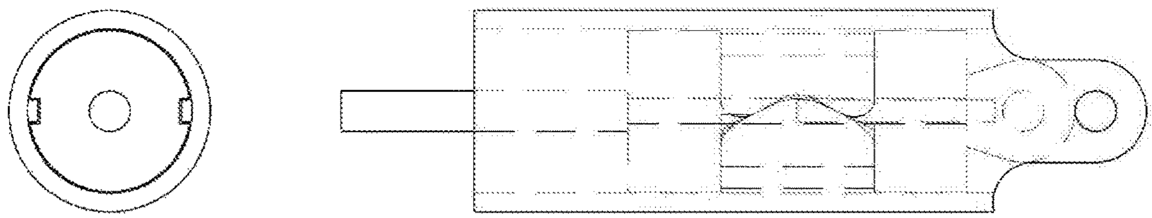
FIGS. 71*a-c* show various views of another embodiment of engagements.
Figure 71B:
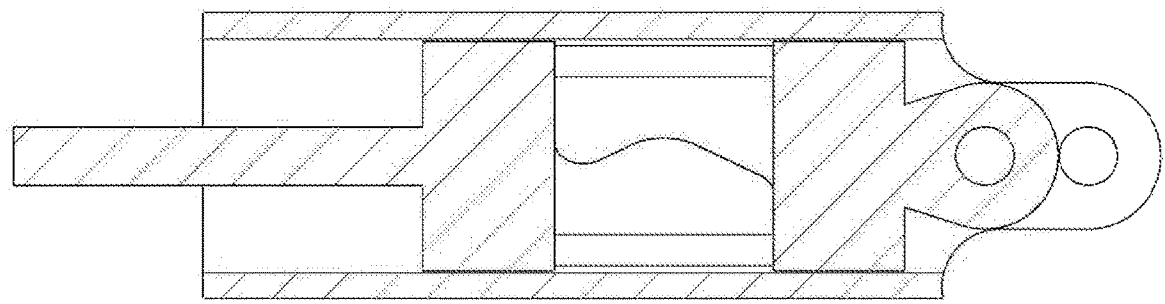
Figure 71C:
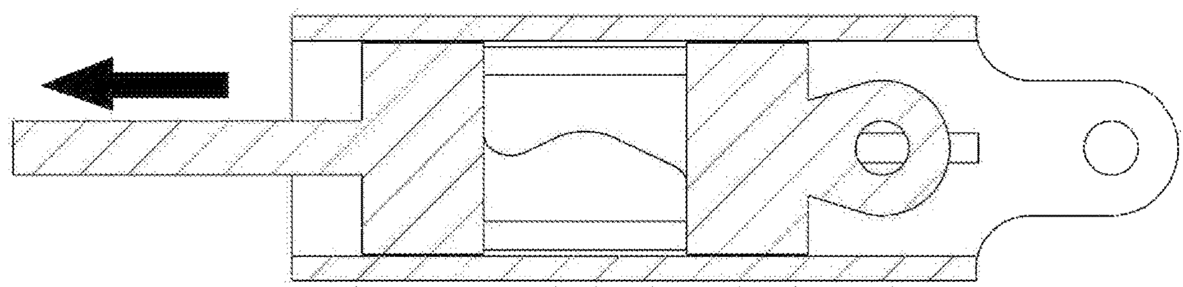
Figure 72A:
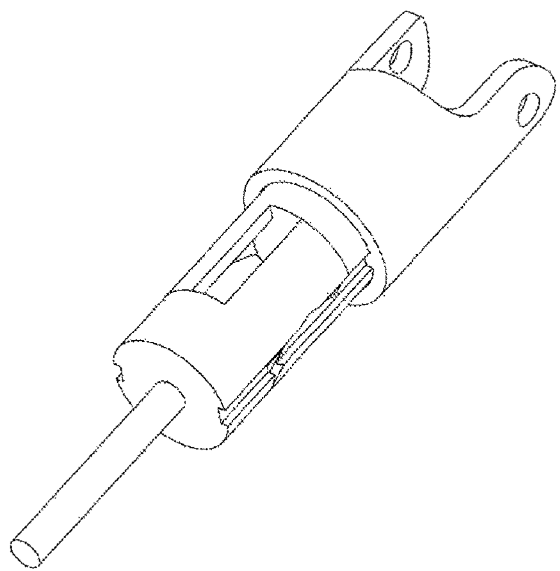
FIGS. 72*a-c* show various views of the engagement without the outer sheath, shown in FIGS. 71*a-c;*
Figure 72B:
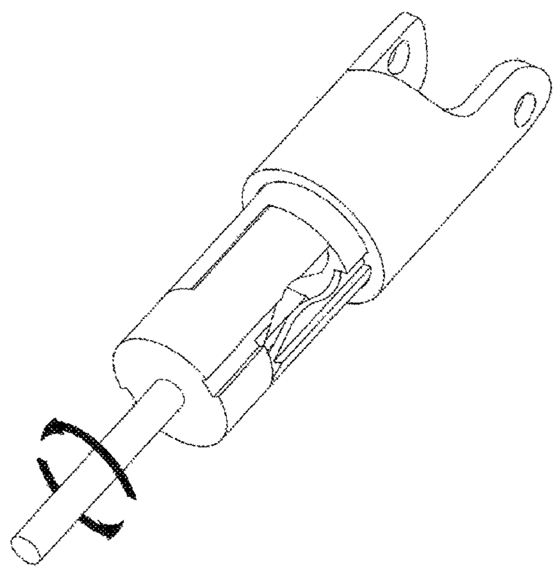
Figure 72C:
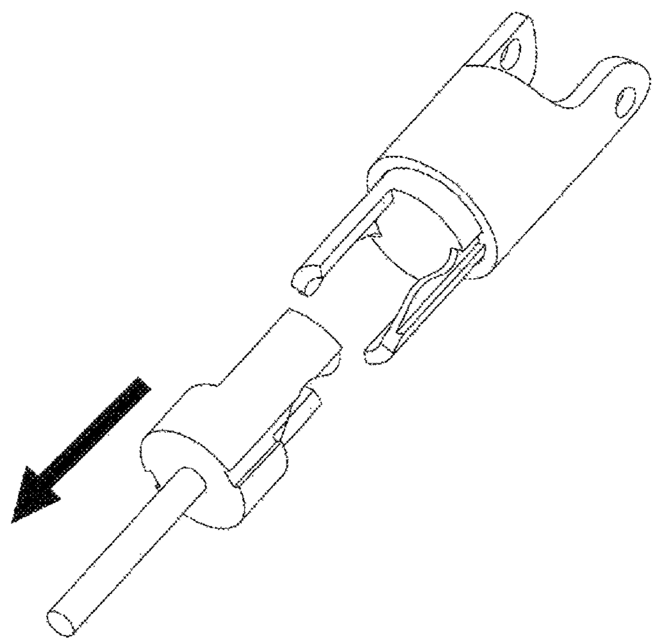
Figure 73A:
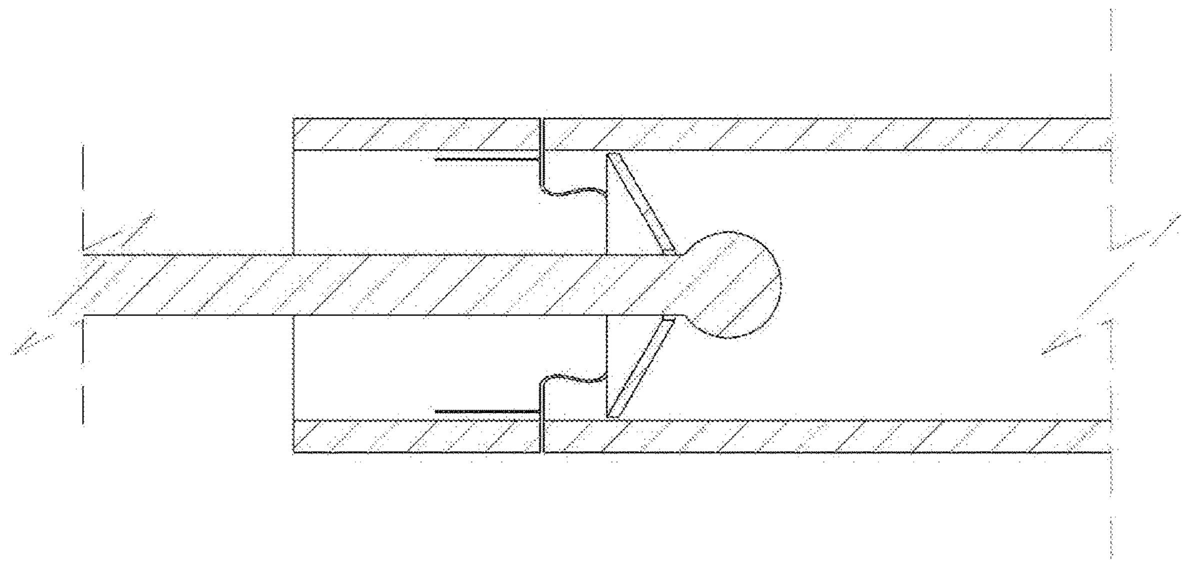
FIGS. 73*a-d* show various views of another embodiment of engagements.
Figure 73B:
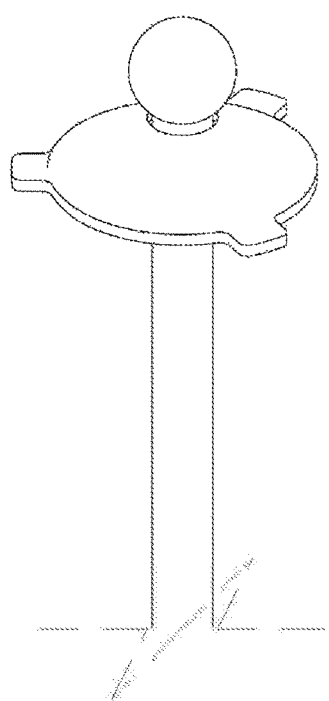
Figure 73C:
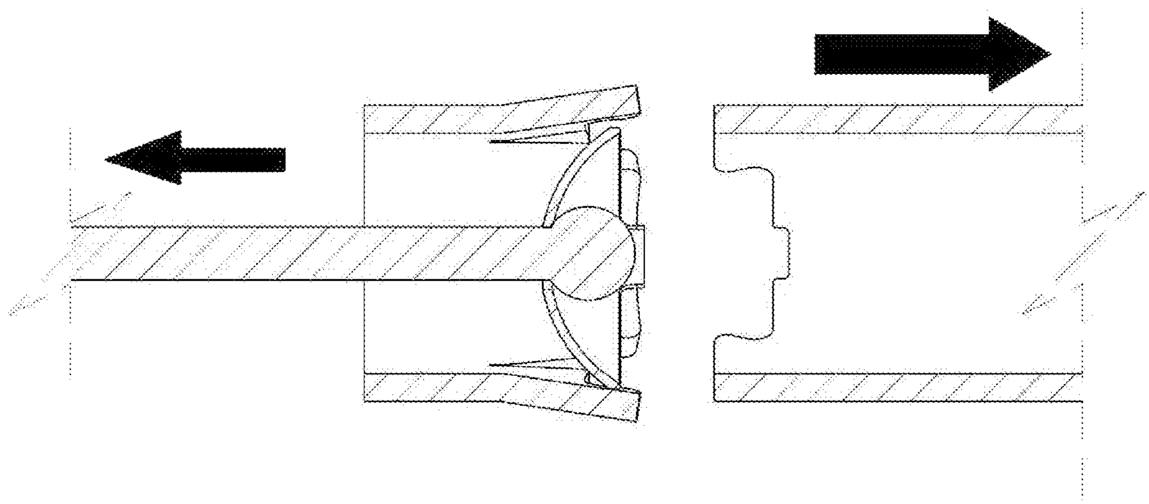
Figure 73D:
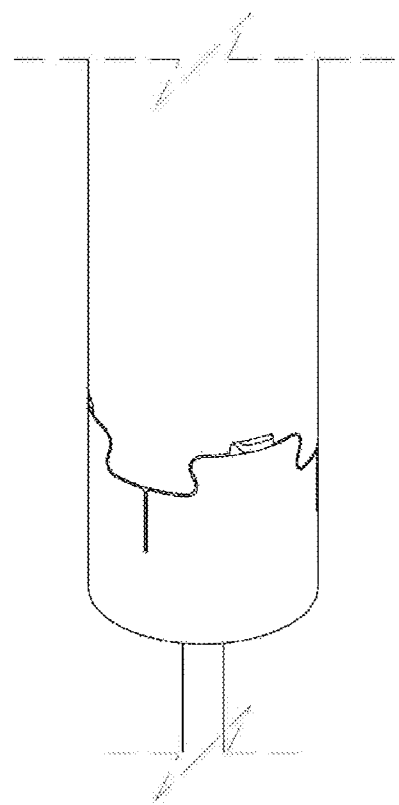
Figure 74A:
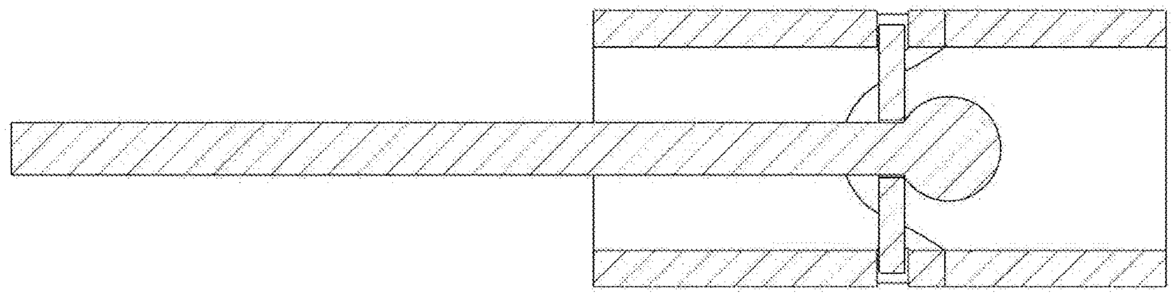
FIGS. 74*a-d* show various views of another embodiment of engagements.
Figure 74B:
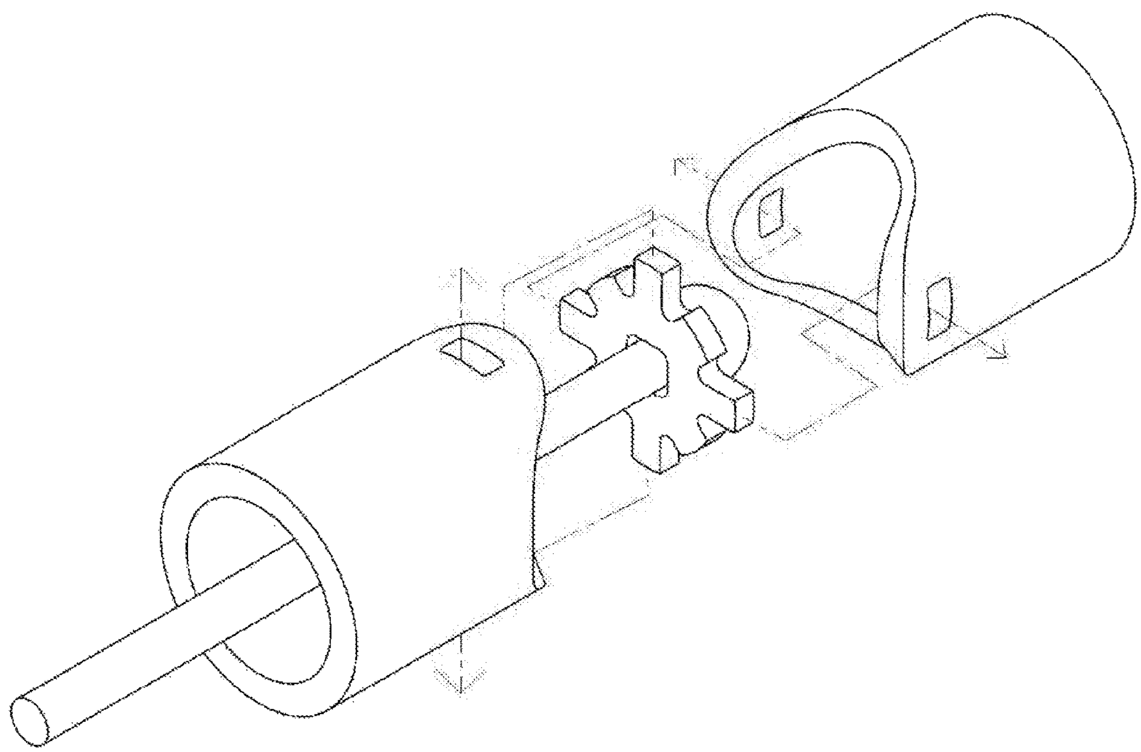
Figure 74C:
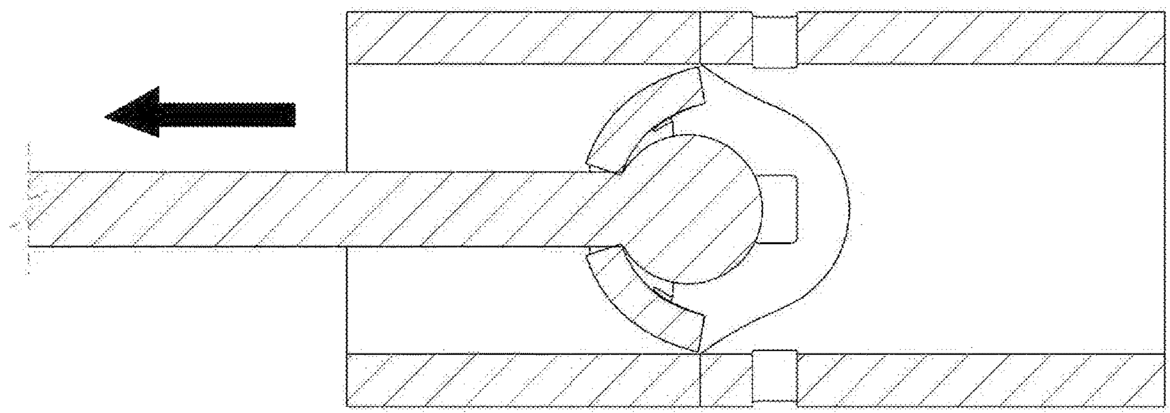
Figure 74D:
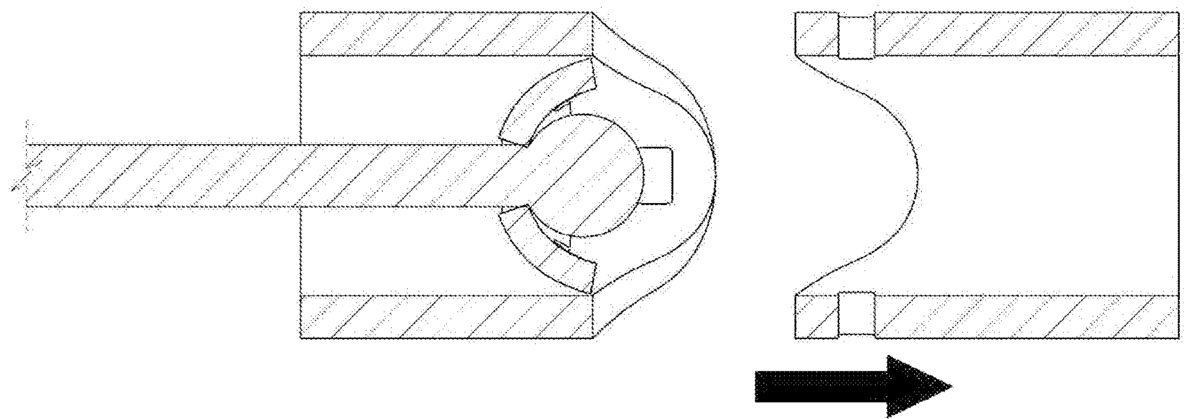
Figure 75A:
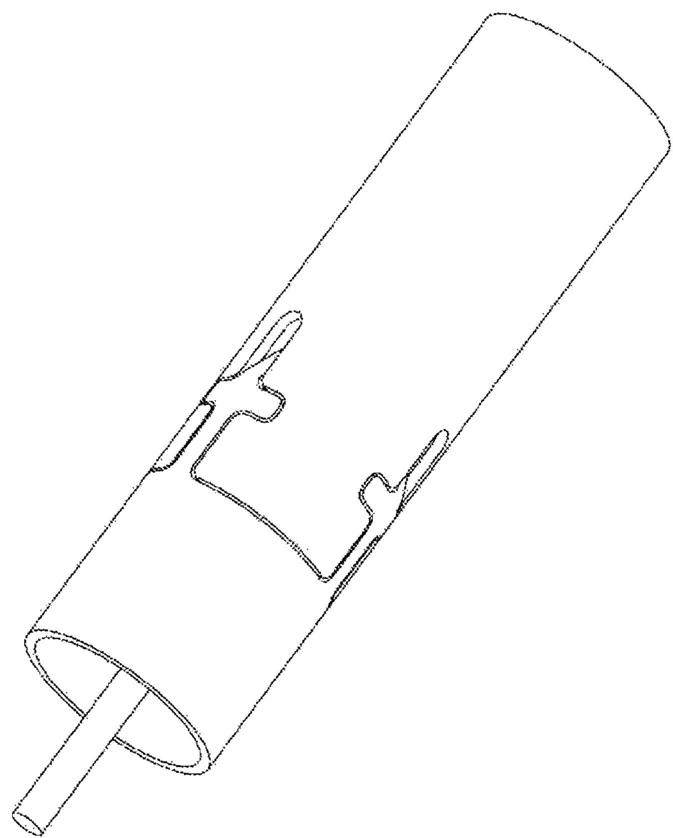
FIGS. 75*a-d* show various views of another embodiment of engagements.
Figure 75B:
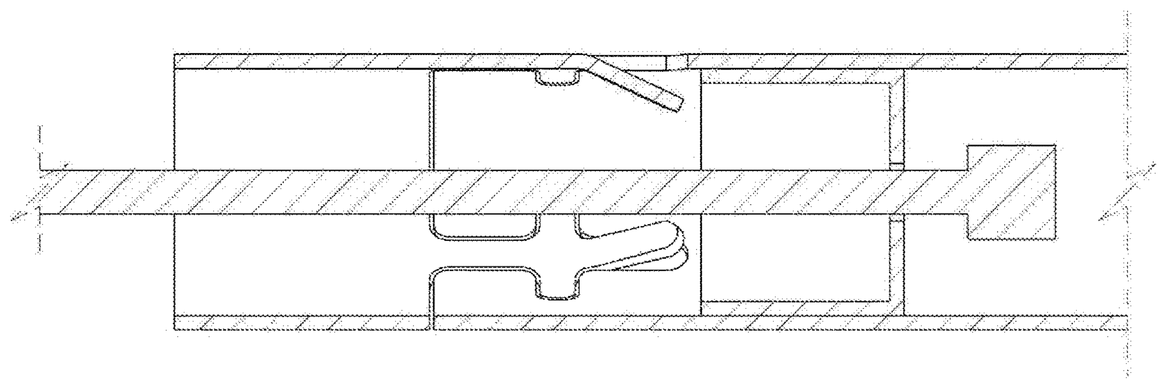
Figure 75C:
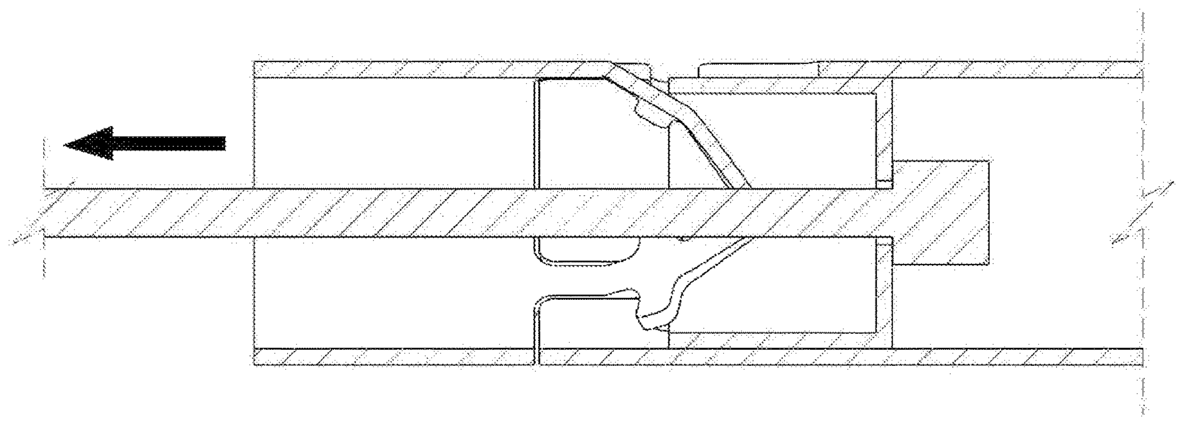
Figure 75D:
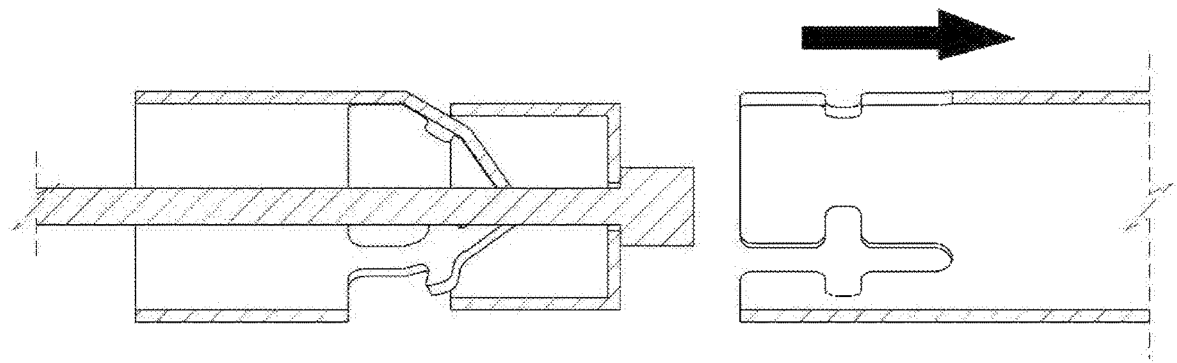

Referring FIG. 62, a person skilled in the art should understand that the driving engagement and/or the housing engagement provide a bidirectional controllable rotation. For bidirectional controllable rotation, there must be interfacing surfaces between the clip assembly and the driving assembly that are not perpendicular to the long axis of the clip assembly. This may be a combination of flat surfaces and/or curved surfaces. This will be known as the total rotational engagement surface. In some embodiments of rotation engagements, each half of the engagement portion must have a feature, or set of features, with at least two opposing rotational engagement surfaces, that are located on either side of a center plane (that is coincidental with the long axis of the clip assembly) to have controllable rotation in two directions. For unidirectional rotation, only one rotational engagement surface may be required. An engaged rotational engagement is configured to rotate and disengage.

A person skilled in the art should understand that, to translate forces distally and proximally (for example, open and close the jaws, move the clip assembly distally or proximally), the driving engagement and/or the housing engagement must provide interfacing surfaces. These interfacing surfaces are not parallel to the long axis of the assemblies. This may be a combination of flat surfaces and/or curved surfaces. This will be known as the total push/pull engagement surface. In some engagements, each half of the engagement portion must have a feature, or set of features, with at least two opposing total push/pull engagement surfaces. An engaged engagement is configured to move translationally and disengage. A person skilled should readily understand that the structures of the driving engagement and the housing engagement are often interchangeable with/without some adaptive modifications. The engagement described in this application should be understood by the person skilled as used for the driving engagement and/or the housing engagement.

Figure 40:
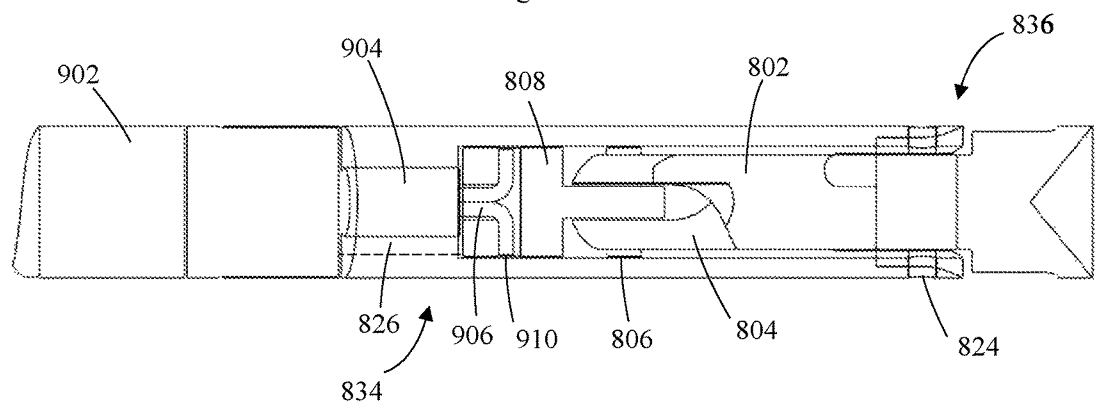
FIG. 40 shows a top view of the embodiment shown in FIG. 36.
Figures 44A, 44B:
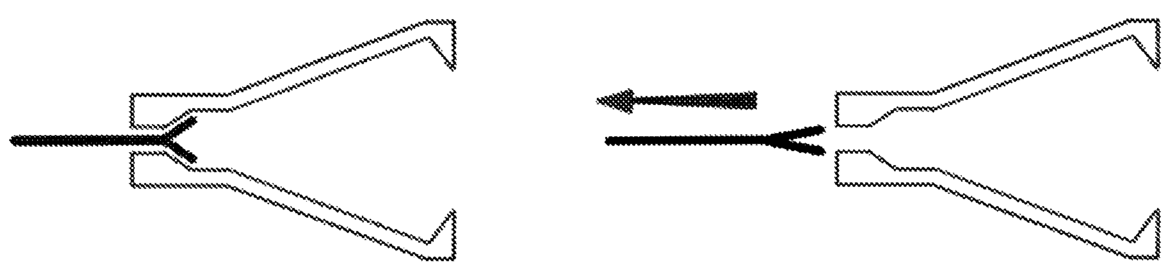
FIGS. 44*a-b* show various views of another embodiment of engagements.

Referring FIGS. 40, 44*a-b,* 46*a-c,* 47*a-d,* in some embodiments, the distal end 910 of the driver 906 comprises a tag 910. In some embodiments, the tag 910 is a T-tag. A person skilled in the art should understand that the hook 910 could also be a Y, one sided L or J bend, an eyelet, or other suitable shapes. The tag 910 is received in the releasing portion 808 to form the driving engagement. The tag 910 promotes a stabilized push and pull motions under normal use. Once disengagement is required, the two t-shaped wires move radially inward, which allows the wires to slip out from the release portion 808, thus full disengagement is achieved. The tag 910 also helps for the rotation control.

Figure 59A:
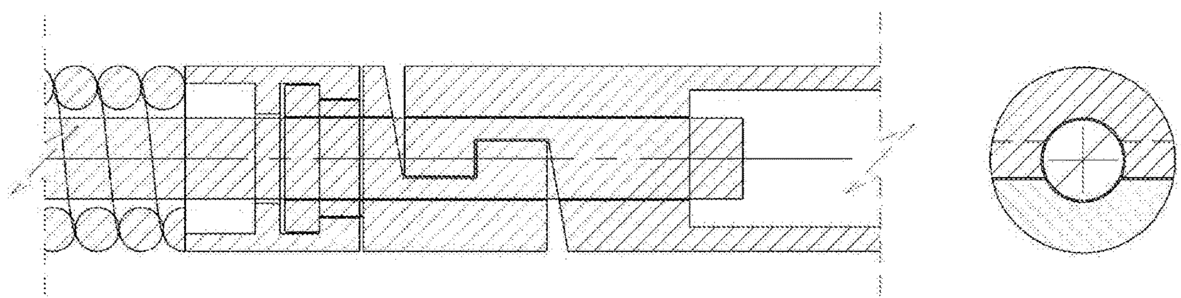
FIGS. 59*a-b* show various views of another embodiment of engagements.
Figure 59B:
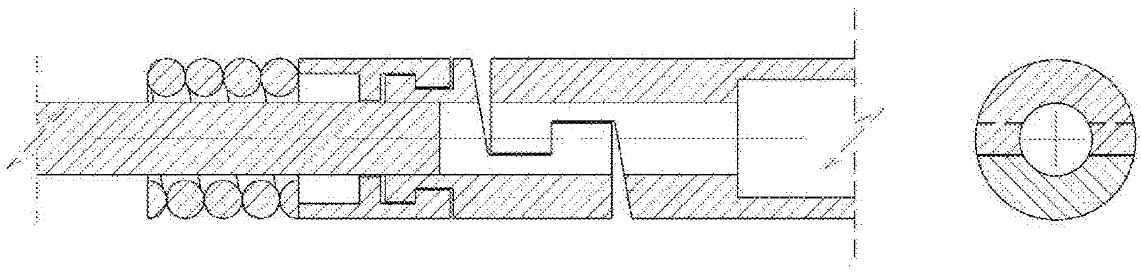
Figure 60A:
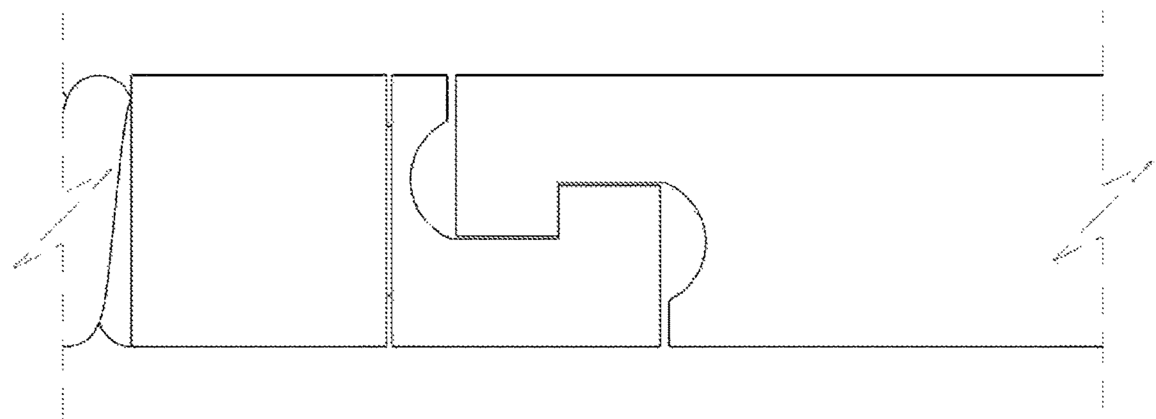
FIGS. 60*a-f* show various embodiments of engagements.
Figure 60B:
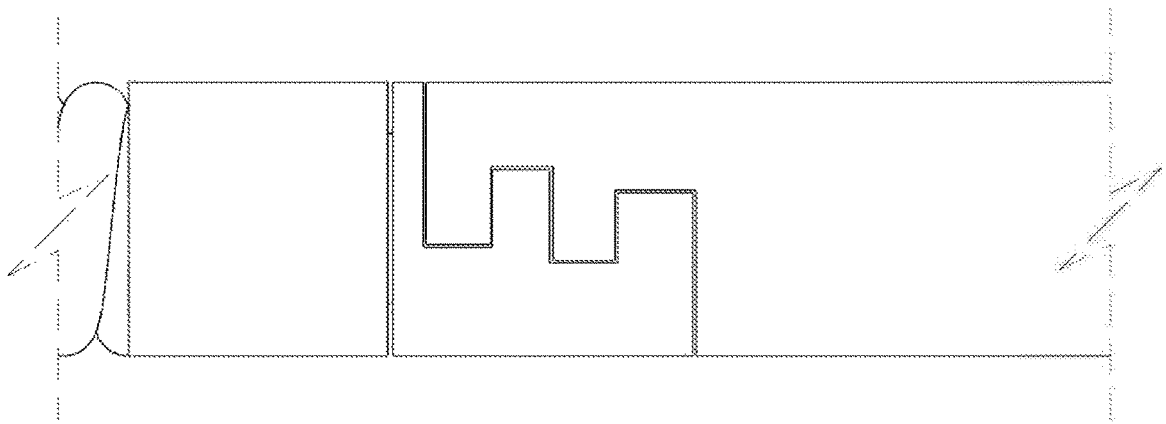
Figure 60C:
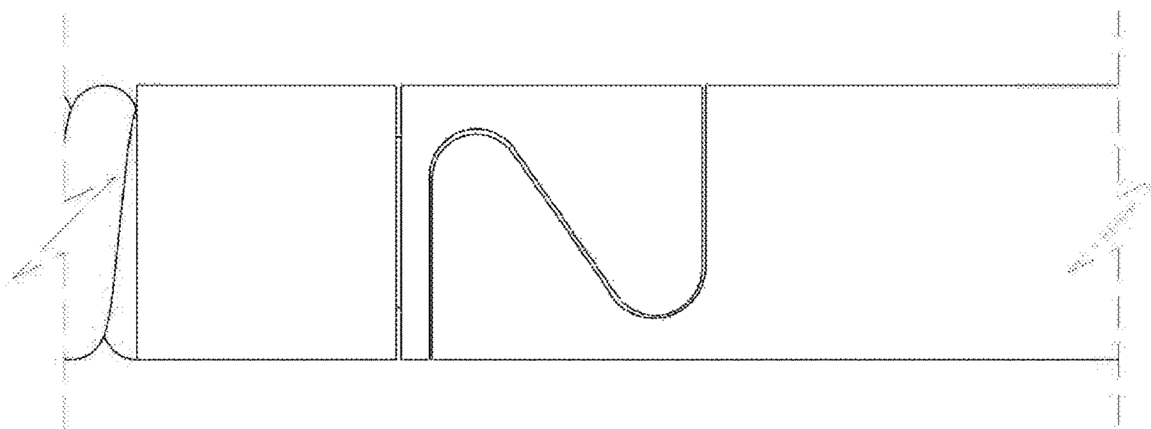
Figure 60D:
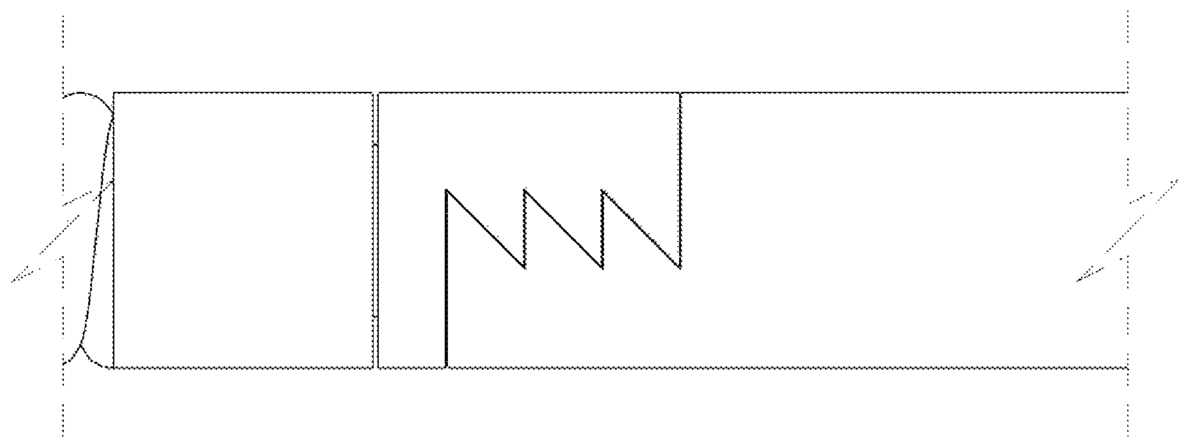
Figure 60E:
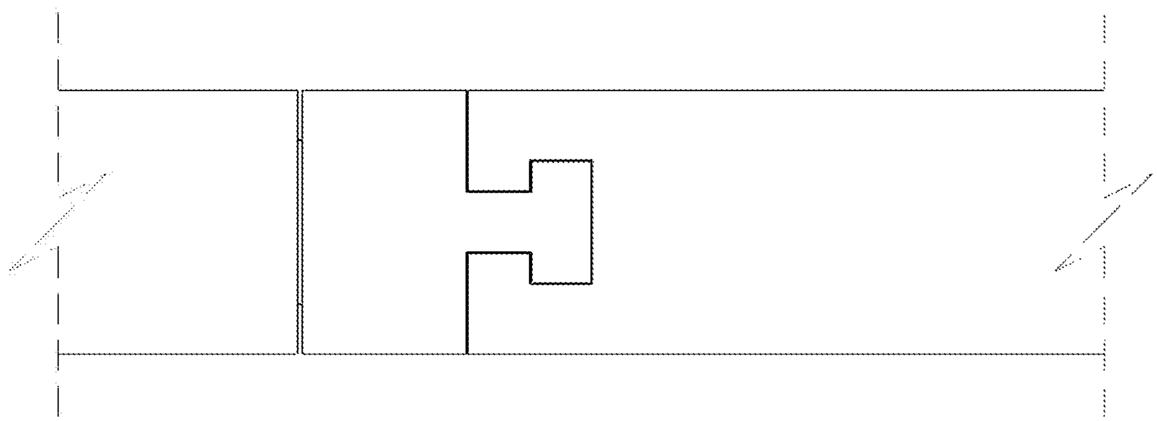
Figure 60F:
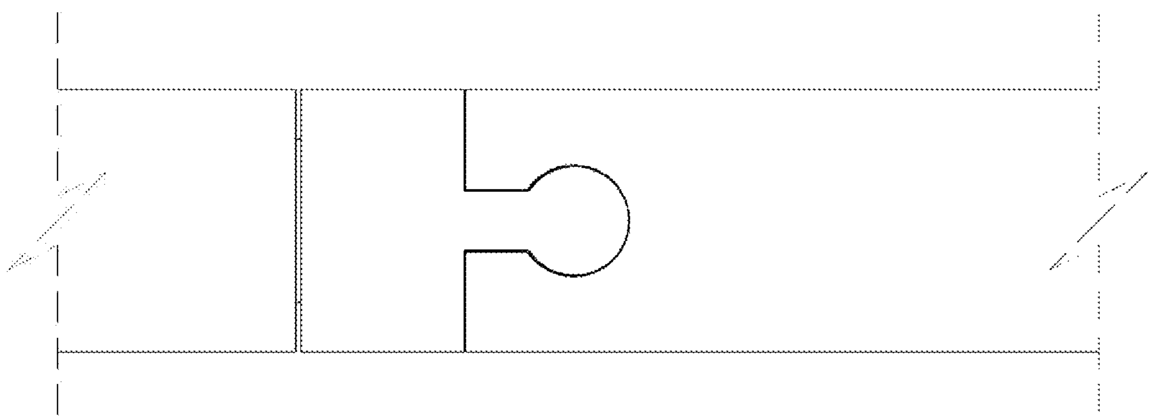
Figure 61:
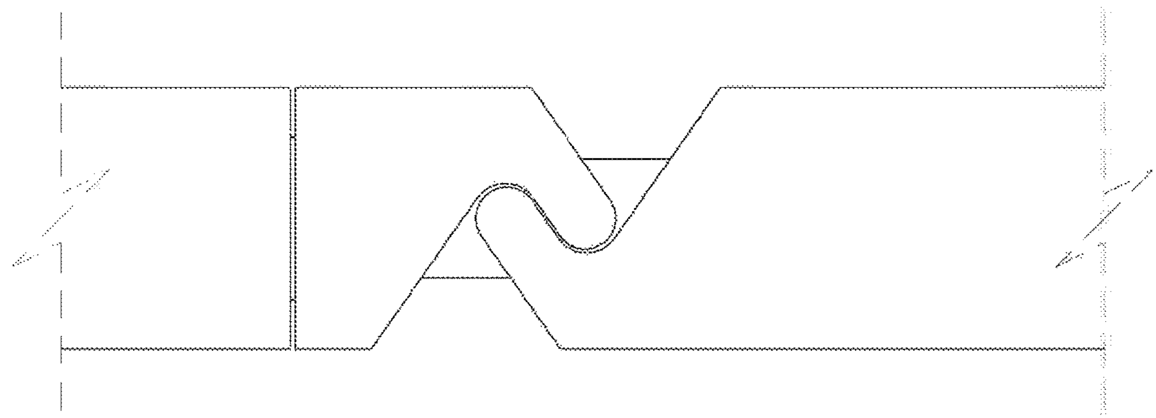
FIG. 61 shows another embodiment of engagements.

Referring to FIGS. 59*a-b,* in some embodiments, the engagement between the distal end 908 and the proximal end 834 is a handshake engagement. The distal end 908 and the proximal end 834 each have a handshake half. Once the distal end 908 and the proximal end 834 engage, the inner tube 904 extends into the proximal end 834 of the housing 820 and prevents the distal end 908 and the proximal end 834 from disengaging. Once the inner tube 904 is retracted out of the proximal end 834, the engaged distal end 908 and the proximal end 834 are able to be separated.

The inner tube 904 that is retracted to allow disengagement must have a diameter such that the distal end 908 and the proximal end 834 remain together until purposefully removed. The combined clearance of both inner diameters ID of the handshake halves with the outer diameter OD of the inner tube 904 must be less than the height H of the total engagement surface when measured perpendicular to the long axis of the clip assembly 800.

Referring FIGS. 60*a-f* and 61, a person skilled in the art should understand that all interactions may have symmetrical geometries for the clip assembly and the driving assembly, or asymmetrical. All geometries on either side may be symmetrical across a center plane, or asymmetrical. Geometry to promote ready disengagement when removing the inner tube may be in the form of back-angles, clearances, or any other suitable geometry for this purpose. Geometries used may or may not be visible from the outside of the clip assembly and the driving assembly and may be within outer material. Interfacing surfaces of the handshake and the inner tube do not need to be cylindrical and do not have to be matching shapes.

A person skilled in the art should understand that the engagements between the clip assembly and the driving assembly are not limited to the above discussed embodiments. Some other exemplary embodiments as follows:

Referring to FIGS. 43*a-d,* another embodiment of the engagement comprises a driving wire wound on the release portion. The driving wire is configured to be pulled with a predetermined force and be straightened to be disengaged.

Figure 45A:
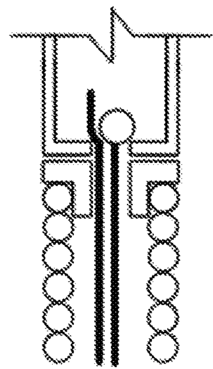
FIGS. 45*a-c* show various views of another embodiment of engagements.
Figure 45B:
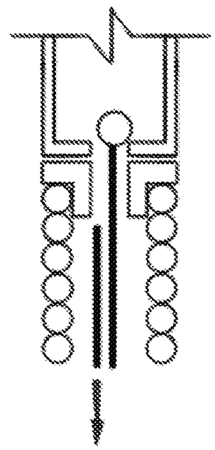
Figure 45C:
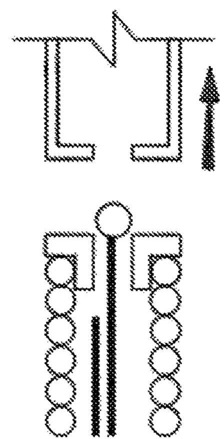
Figure 46A:
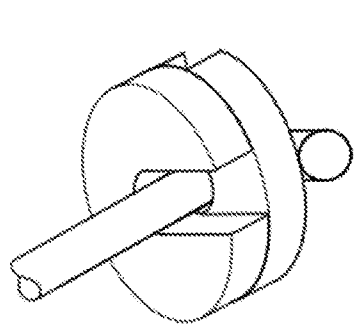
FIGS. 46*a-c* show various views of another embodiment of engagements.
Figure 46B:
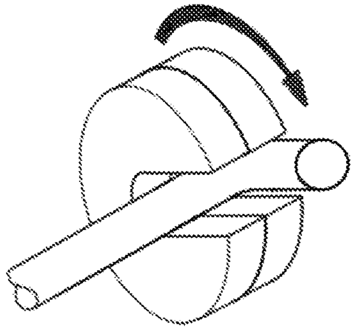
Figure 46C:
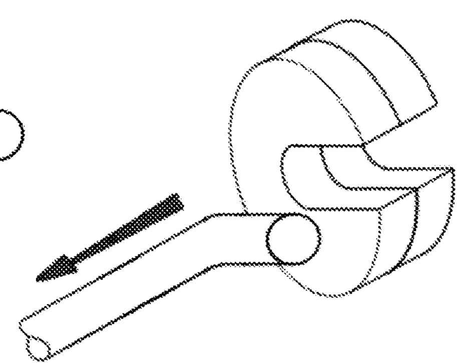
Figure 47A:
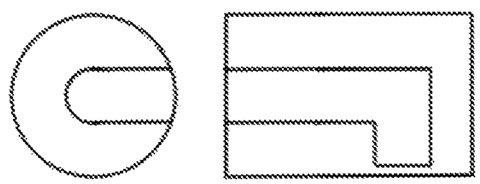
FIGS. 47*a-d* show various views of another embodiment of engagements.
Figure 47B:
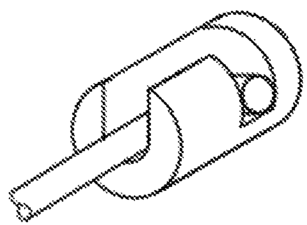
Figure 47C:
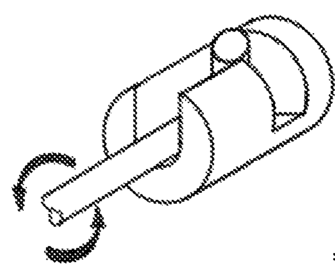
Figure 47D:
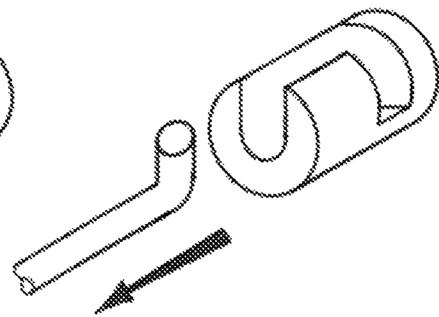

Referring to FIGS. 45*a-c,* another embodiment of the engagement comprises a pull wire and a release portion with a ball. A hole of the outer sheath is configured to receive or release the ball of the release portion. However, the hole cannot release the ball of the release portion with the pull wire inserting through the hole. In another embodiment, the hole is on the release portion and the ball is included in the driving assembly. A person skilled in the art should understand that the ball can be replaced by any other larger geometry that cannot be removed through the hole without the pull wire being removed.

Figure 48A:
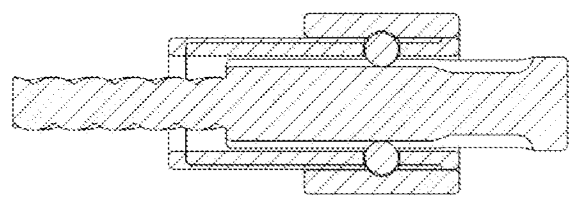
FIGS. 48*a-c* show various views of another embodiment of engagements.
Figure 48B:
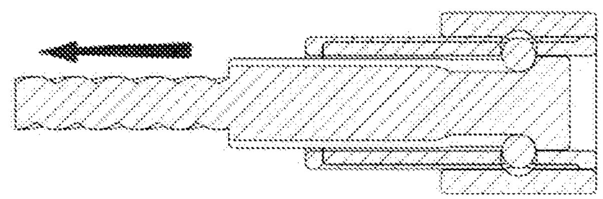
Figure 48C:
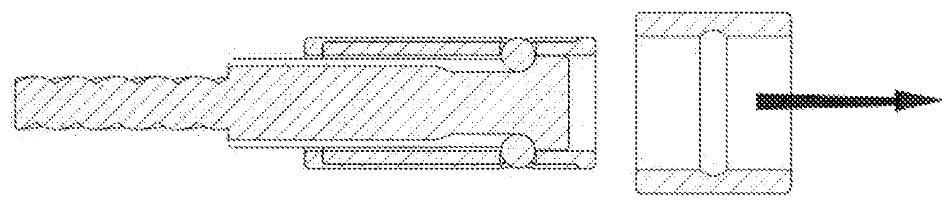

Referring to FIGS. 48*a-c,* another embodiment of the engagement is a ball detent connection.

Figure 49A:
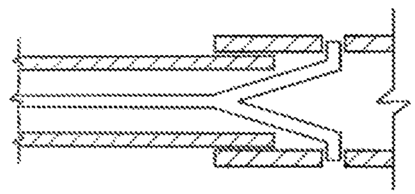
FIGS. 49*a-c* show various views of another embodiment of engagements.
Figure 49B:
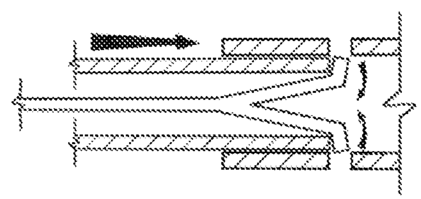
Figure 49C:
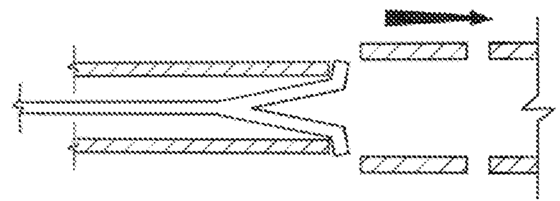

Referring to FIGS. 49*a-c,* another embodiment of the engagement comprises L-arms and the inner tube. The L-arms removably attached to the housing of the clip assembly. The inner tube may move in the distal direction and push on the L-arms and forces the L-arms to move inward and disengage. The L-arms may be attached to the housing by taper, friction, or overmold. The L-arms may also be free floating with a geometry that maintains engagement in the absence of the inner tube.

Figure 50A:
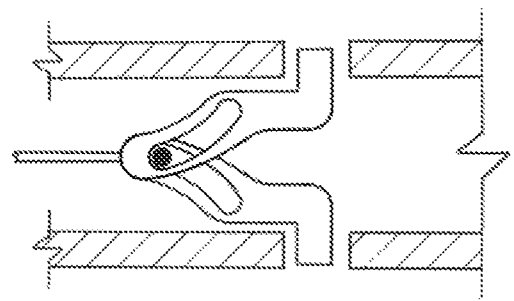
FIGS. 50*a-b* show various views of another embodiment of engagements.
Figure 50B:
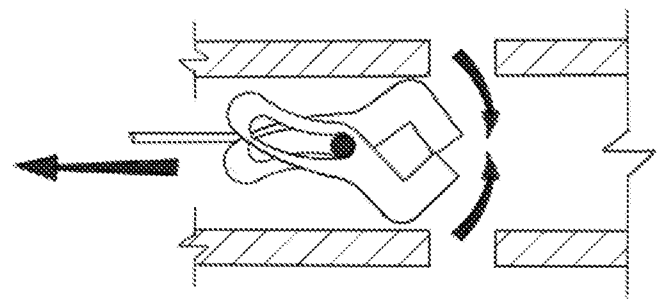

Referring to FIGS. 50*a-b,* another embodiment of the engagement comprises a clip connector traveling on tracks that moves radially inward to disengage from the housing 820.

Figure 51A:
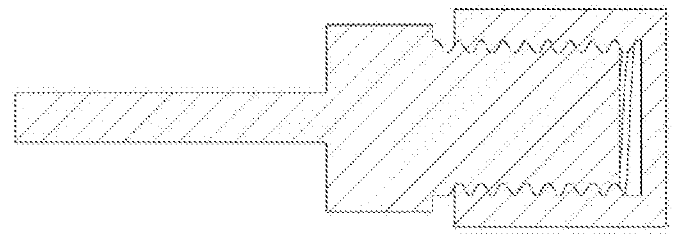
FIGS. 51*a-b* show various views of another embodiment of engagements.
Figure 51B:
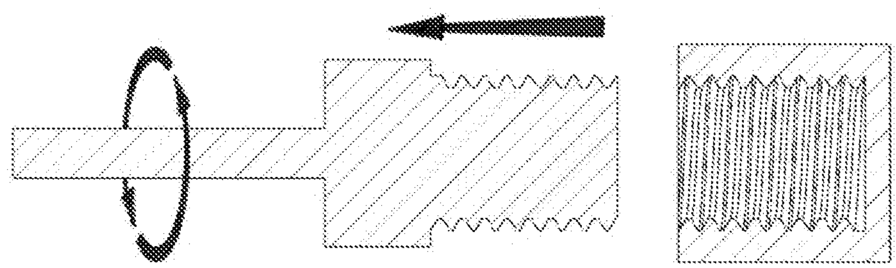

Referring to FIGS. 51*a-b,* another embodiment of the engagement comprises a screw connection between the driver and the release portion. The predetermined force to unscrew this connection must be less than a force that may render the device ineffective.

Figure 52A:
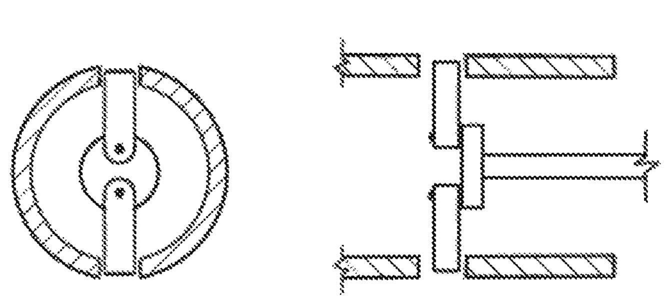
FIGS. 52*a-b* show various views of another embodiment of engagements.
Figure 52B:
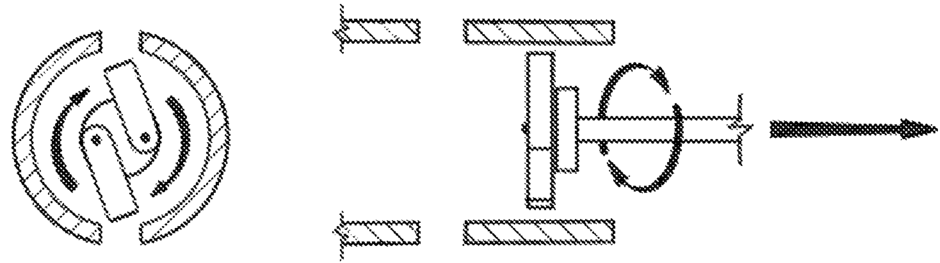

Referring to FIGS. 52*a-b,* in another embodiment of the engagement, the housing comprises two slots or holes. The driver comprises two foldable projects only when the driver rotates clockwise. The projects insert into the slots when rotated counterclockwise, so as to maintain the engagement. When the projects rotate clockwise, the projects retract from the slots, and the driver is able to be disengaged.

Figure 53A:
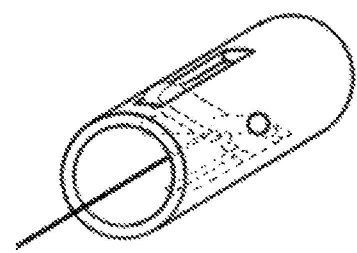
FIGS. 53*a-c* show various views of another embodiment of engagements.
Figure 53B:
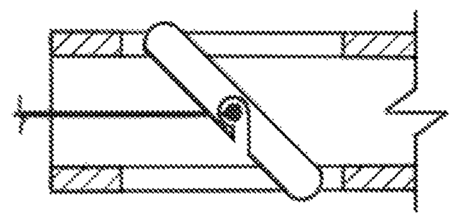
Figure 53C:
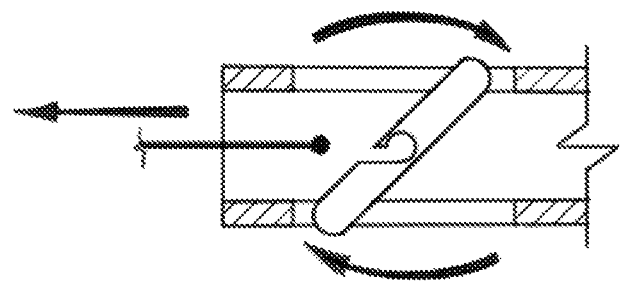

Referring to FIGS. 53*a-c,* in another embodiment of the engagement, a switch bar is configured to rotates in slots disposed on the outer sleeve and to release the driver from the geometry in the middle of the switch bar.

Figure 54A:
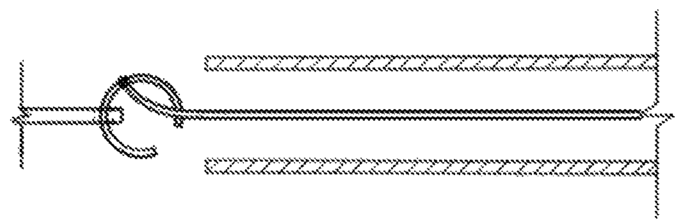
FIGS. 54*a-b* show various views of another embodiment of engagements.
Figure 54B:
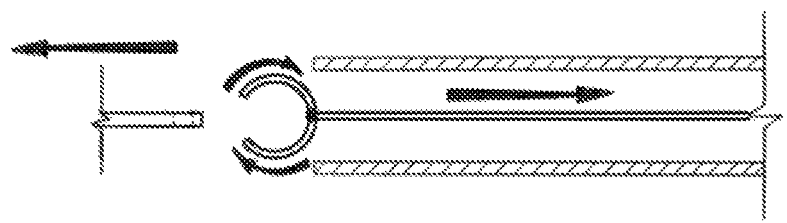

Referring to FIGS. 54*a-b,* in another embodiment of the engagement, the driver comprises a C ring and the release portion comprises a hole. When engaged, the C ring is inserted through the hole of the release portion. The C ring is configured to be pulled until the clip assembly falls off.

Figure 55A:
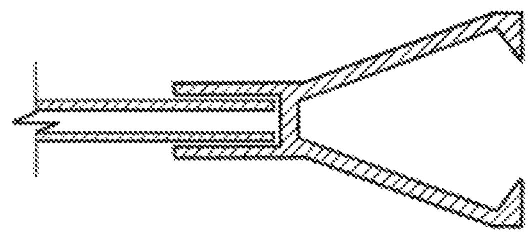
FIGS. 55*a-b* show various views of another embodiment of engagements.
Figure 55B:
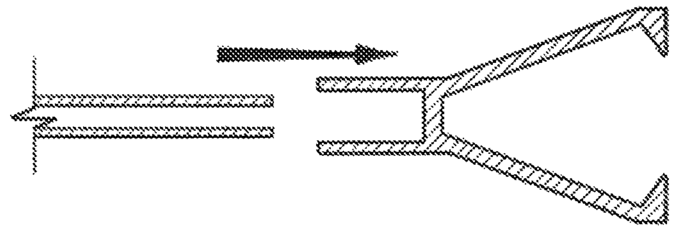
Figure 56A:
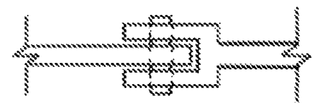
FIGS. 56*a-f* show various views of another embodiment of engagements.
Figure 56B:
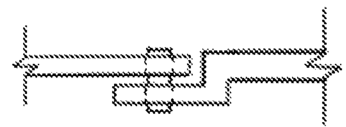
Figure 56C:
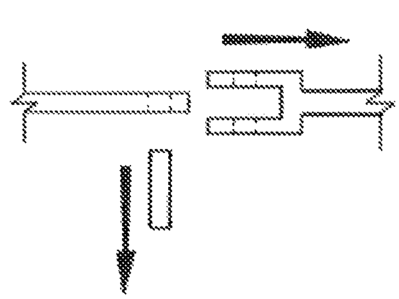
Figure 56D:
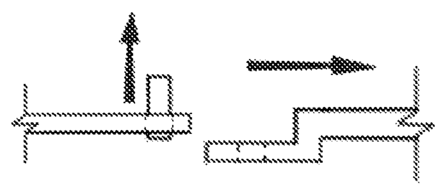
Figure 56E:
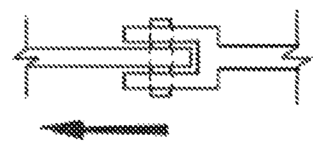
Figure 56F:
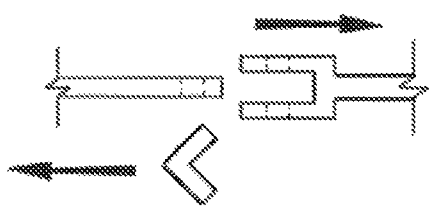

Referring to FIGS. 55*a-b,* in another embodiment of the engagement, the release portion of the clip assembly comprises a hole. The inner tube inserts into the hole and uses constant suction to hold the release portion. Once the suction is turned off, the clip assembly will disengage.

Referring to FIGS. 56*a-f,* in another embodiment of the engagement, a cotter pin is used to tether the driver and the release portion. By removing the cotter pin, the clip assembly would disengage.

Referring to FIGS. 57*a-b,* in another embodiment of the engagement, the release portion is over fit with the outer sheath. A lever is used to eject the release portion. A person skilled in the art should understand that, instead of the lever, the outer tube or a pushing wire may be used to eject the release portion.

Referring to FIGS. 58*a-c,* in another embodiment of the engagement, the release portion comprises a socket. The driver comprises a deflectable balloon. The balloon inserts into the socket and is inflated so that the engagement maintains. The inflated balloon in the socket is deflated to disengage. One skilled in the art should also realize that the balloon could be configured to grasp a feature from the outside or in a manner where inflation, rather than deflation creates the component release.

Referring to FIGS. 69 and 70*a-c,* another embodiment of the engagement comprises at least one angled ramp. The housing comprises at least one flexible tab. The outer sheath comprises retention slots and at least one groove. The flexible tab fits into and locks with the retention slot. The groove is substantially along the center axis of the outer sheath. The angled ramp is configured to move along the groove. When the release of the engagement is required, the angled ramp drives the locking tab toward the center axis to the point where the tab is no longer engaged in the retention slot. Consequently, the engagement is able to separate.

Referring to FIGS. 71*a-c* and 72*a-c,* another embodiment of the engagement comprises two cams in rotational alignment with each other, a retention bar to hold the cams. In one embodiment, the retention bar is a rail that is an integral part of the outer sheath. The retention bar maintains alignment between the two cams and prevents them from rotating. Once the two cams are pull distally (in a direction to close and lock the jaws), the proximal cam will have been pulled into a position, past the retention bar, which allows the proximal cam to rotate with respect to the distal cam and release. The cam angle, in conjunction with force in the proximal direction, causes the rotation and once the proximal cam rotates sufficiently it is free of the lock and releases.

Referring to FIGS. 73*a-d,* in another embodiment of the engagement, the outer sheath and the housing are made with fine cuts which have undercuts which hold them together. The engagement comprises an invertible washer. The washer expands under load and causes the end of the outer sheath to expand to disengage from the housing.

Referring to FIGS. 74*a-d,* in another embodiment of the engagement, the outer sheath and the housing have a match pattern. The interfacing ends allow for a flat and flexible washer to secure the two components together. Once the drive system is pulled through the washer, the components are separated. The washer is then retained with the driving assembly.

Referring to FIGS. 75*a-d,* in another embodiment of the engagement, the housing comprises at least one inset tab. The outer sheath comprises at least one bendable arm. The inset tab and the bendable arm are fit to each other. The inner tube or the driver is pulled in a direction to bend the arm and disengage the tabs. This in turn releases the housing from the outer sheath.

Figure 77A:
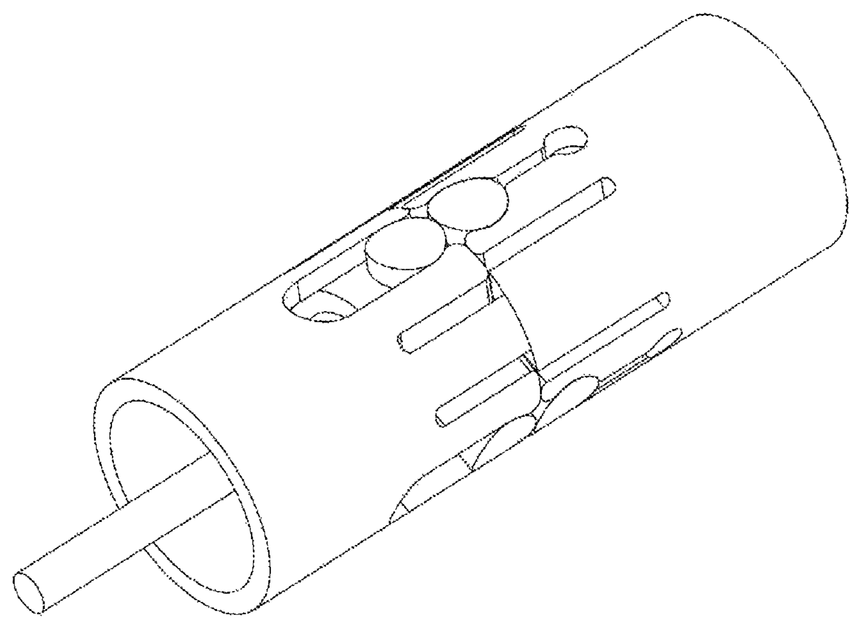
FIGS. 77*a-c* show various view of another embodiment of engagements.
Figure 77B:
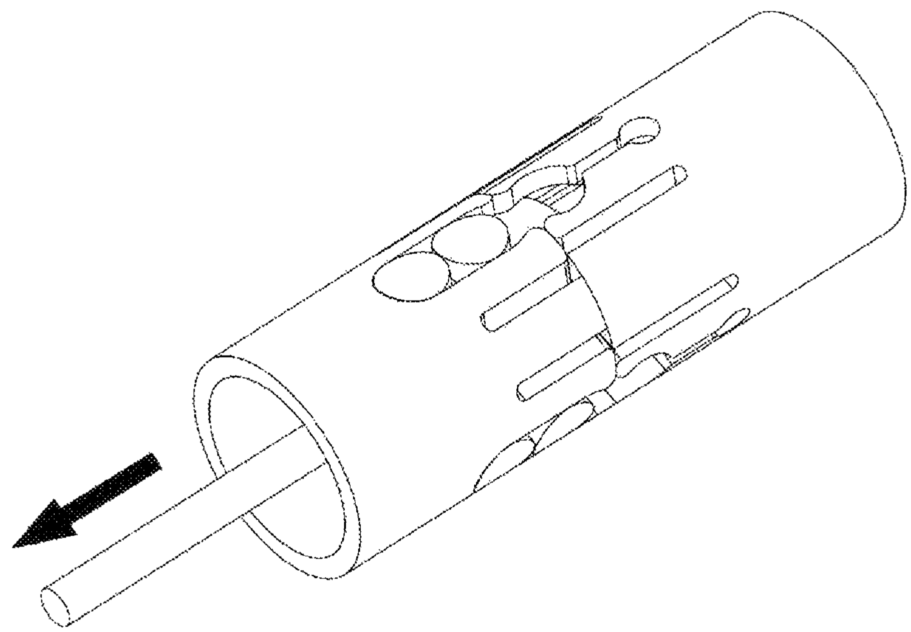
Figure 77C:
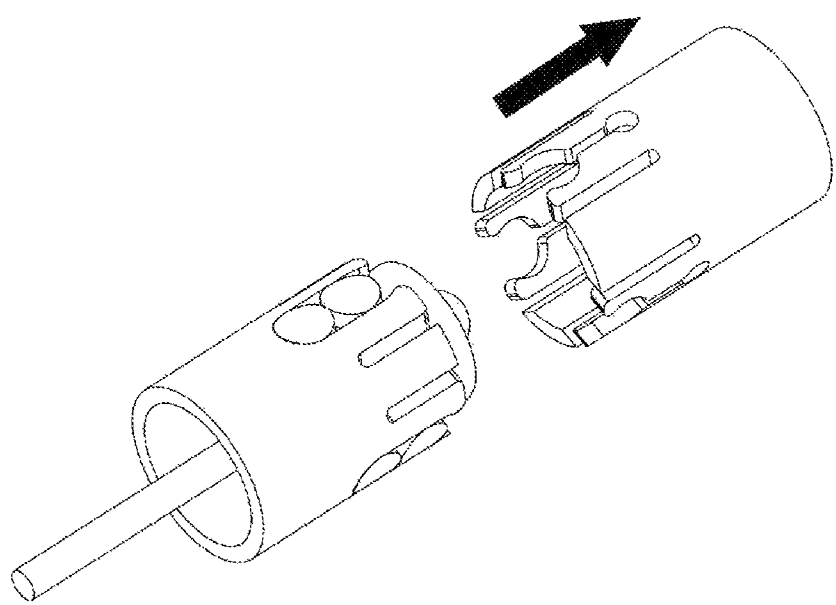

Referring to FIGS. 77*a-c,* in another embodiment of the engagement, the inner tube (or the driver) comprises two aligned bosses. The aligned bosses join the outer sheath and the housing together until the inner tube is pulled out of the housing and into the outer sheath. At this point, the housing is released.

Figure 76A:
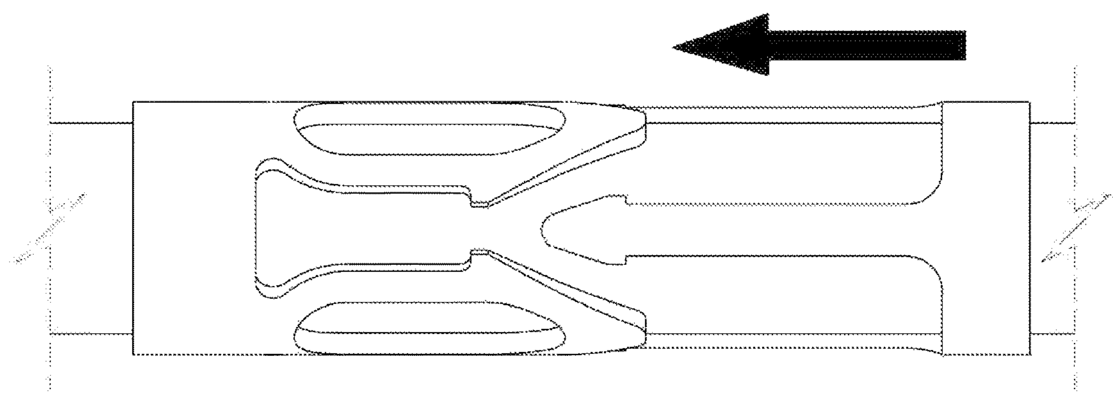
FIGS. 76*a-b* show various view of another embodiment of engagement.
Figure 76B:
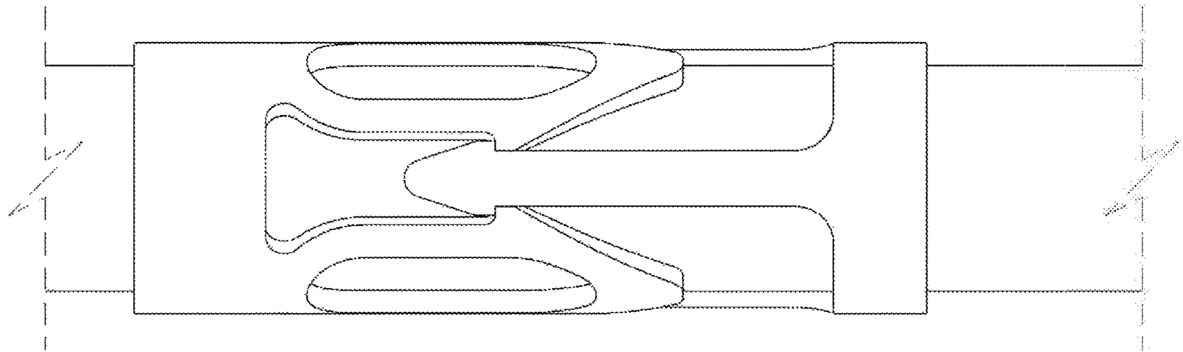

Referring to FIGS. 76*a-b,* a locking mechanism is discussed. This locking mechanism helps to hold the clip assembly in the final and closed position shown as FIG. 76*b*. All actions are axial and radial.

Some embodiments of the clip assembly are disclosed in the U.S. Provisional Application No. 62/586,515, filed on Nov. 15, 2017, titled “END EFFECTORS ACTUATION PLATFORM,” and the U.S. Provisional Application No. 62/586,573, filed on Nov. 15, 2017, titled “AVULSION FORCEPS,” which are specifically and entirely incorporated by reference herein.

A person skilled in the art should reasonably understand that in order to be MR Safe, some embodiments of the clip assembly described above are made of electrically nonconductive or non-magnetic material. The clip assembly has all components that are left in the patient.

A person skilled in the art should reasonably understand that at least one or multiple portions of the device may be constructed of or coated in a radio-opaque or radio-visible material to be identifiable with medical imaging technologies.

A person skilled in the art should reasonably understand that the above designs are readily applied to a metal clip or other metal devices.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

The invention claimed is:

1. An endoscopic device, comprising:

a clip assembly, comprising a first jaw, a second jaw, a housing having an internal channel, wherein at least a portion of the first and second jaws is disposed within the internal channel, the first and second jaws selectively move along with the internal channel between a fully closed position and a fully opened position, and a release portion, connecting to the first and second jaws, wherein at least a portion of the release portion is proximal from the first and second jaws, and wherein a laterally outer portion of at least one jaw includes a retention fin configured to prevent a collar from sliding away from a distal end of the at least one jaw; and a driving assembly interfacing with the clip assembly, wherein the driving assembly includes:

an outer sheath, an inner tube, movably disposed within the outer sheath, and a driver, movably disposed within the inner tube, and removably received within the release portion, wherein the driver is unbrokenly released from the release portion by a predetermined pull force, wherein the housing and the outer sheath form a releasable handshake engagement, and the inner tube extending into the housing prevents the handshake engagement from disengaging, wherein a distal end of the outer sheath and the inner tube form a housing engagement with a proximal end of the housing to provide bidirectional rotation, and wherein the clip assembly is made of electrically nonconductive or non-magnetic material for all components that are left in a patient.

2. The endoscopic device of claim 1, wherein the clip assembly further comprises a distal stopper, disposed at a distal end of the internal channel, and configured to force the first and second jaws fully open when the release portion move to its most distal position.

3. The endoscopic device of claim 1, wherein the driver comprises a T-tag received in the releasing portion, two wires of the T-tag selectively move radially inward and slip out from the release portion when a predetermined force is pulled.

4. The endoscopic device of claim 1, wherein the clip assembly comprises a pivot, wherein the first and second jaws pivotally connect the pivot.

5. The endoscopic device of claim 4, wherein the release portion is pivotally connected to the pivot.

6. The endoscopic device of claim 4, wherein the release portion is fixed to the pivot.

7. The endoscopic device of claim 1, wherein the first and second jaws are disposed at each side of at least a portion of the release portion.

8. The endoscopic device of claim 1, wherein the housing comprises an alignment slot, configured to receive at least a portion of the first jaw when the first jaw in a non-closed position.

9. The endoscopic device of claim 8, wherein the alignment slot is configured to receive an alignment rib of the first jaw.

10. The endoscopic device of claim 1, wherein the housing comprises two alignment slots.

11. The endoscopic device of claim 1, wherein the difference between an inner diameter of a proximal end of the internal channel, or a distal end of the outer sheath, and an outer diameter of the inner tube is less than a height of a total engagement surface when measured perpendicular to a long axis of the endoscopic surgical device.

12. The endoscopic device of claim 1, wherein a distal end of the outer sheath is configured to fully rotate 360 degrees without separating from the other part of the outer sheath.

13. The endoscopic device of claim 1, wherein the handshake engagement is a rotation handshake.

14. The endoscopic device of claim 1, wherein the handshake engagement is a translational handshake.

15. The endoscopic device of claim 1, wherein a geometry of the internal channel is corresponding to a geometry of the release portion.

16. The endoscopic device of claim 1, wherein the first and second arms are made in one-piece and are connected through a fulcrum.

17. The endoscopic device of claim 1, wherein the first arm is longer than the second arm.

18. The endoscopic device of claim 1, wherein interfacing surfaces between the clip assembly and the driving assembly are not perpendicular to a long axis of the clip assembly.

19. The endoscopic device of claim 1, wherein the retention fin is disposed near a distal end of the at least one jaw.

20. The endoscopic device of claim 1, wherein the retention fin includes a negative angle.

* * * * *